US010053714B2

(12) United States Patent
Chu et al.

(10) Patent No.: US 10,053,714 B2
(45) Date of Patent: Aug. 21, 2018

(54) ACID-TOLERANT YEAST CELL, METHOD OF PRODUCING ORGANIC ACID USING THE SAME, AND METHOD OF PRODUCING THE YEAST CELL

(71) Applicant: Samsung Electronics Co., Ltd., Suwon-si, Gyeonggi-do (KR)

(72) Inventors: Hunsu Chu, Seoul (KR); Hwayoung Cho, Hwaseong-si (KR); Jinhwan Park, Suwon-si (KR); Dongsik Yang, Seoul (KR); Hongsoon Rhee, Suwon-si (KR); Kwangmyung Cho, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/222,646

(22) Filed: Jul. 28, 2016

(65) Prior Publication Data

US 2017/0029853 A1    Feb. 2, 2017

(30) Foreign Application Priority Data

Jul. 28, 2015   (KR) .................. 10-2015-0106771

(51) Int. Cl.
| | |
|---|---|
| C12N 1/20 | (2006.01) |
| C12N 1/16 | (2006.01) |
| C12N 9/02 | (2006.01) |
| C12N 9/04 | (2006.01) |
| C12P 7/56 | (2006.01) |
| C07H 21/04 | (2006.01) |
| C12N 9/10 | (2006.01) |
| C12N 9/88 | (2006.01) |
| C12N 15/52 | (2006.01) |

(52) U.S. Cl.
CPC ............ *C12P 7/56* (2013.01); *C12N 9/0006* (2013.01); *C12N 9/0036* (2013.01); *C12N 9/0071* (2013.01); *C12N 9/1029* (2013.01); *C12N 9/88* (2013.01); *C12N 15/52* (2013.01); *C12Y 101/01008* (2013.01); *C12Y 101/01027* (2013.01); *C12Y 101/01028* (2013.01); *C12Y 101/02003* (2013.01); *C12Y 101/02004* (2013.01); *C12Y 106/05003* (2013.01); *C12Y 106/05009* (2013.01); *C12Y 114/19001* (2013.01); *C12Y 203/01022* (2013.01); *C12Y 203/01158* (2013.01)

(58) Field of Classification Search
None
See application file for complete search history.

(56) References Cited

U.S. PATENT DOCUMENTS

| | | | |
|---|---|---|---|
| 6,194,166 B1 | 2/2001 | Okado et al. | |
| 8,637,289 B2 | 1/2014 | Anthony et al. | |
| 8,951,776 B2 | 2/2015 | Stephanopoulos et al. | |
| 2005/0112737 A1 | 5/2005 | Liu et al. | |
| 2014/0295516 A1 | 10/2014 | Argyros et al. | |
| 2014/0329287 A1 | 11/2014 | Blazeck et al. | |
| 2015/0024009 A1 | 1/2015 | Lang et al. | |
| 2015/0064752 A1 | 3/2015 | Lee et al. | |
| 2015/0140625 A1 | 5/2015 | Lee et al. | |
| 2015/0167031 A1 | 6/2015 | Kim et al. | |
| 2015/0225752 A1 | 8/2015 | Lim et al. | |

FOREIGN PATENT DOCUMENTS

| | | |
|---|---|---|
| EP | 1 437 405 A1 | 7/2004 |
| EP | 2 439 271 A1 | 4/2012 |
| EP | 2826857 A1 | 1/2015 |
| JP | 2014-054239 A | 3/2014 |
| WO | WO 2011/023298 A1 | 3/2011 |
| WO | WO 2014/043591 A1 | 3/2014 |

OTHER PUBLICATIONS

Hashida-Okado et al. AUR1, a novel gene conferring auriobasidin resistance on *Saccharomyces cerevisiae*: a study of defective morphologies in Aur1p-depeleted cells., Mol Gen Genet (1996), 251: 236-244.*
Branduardi et al., "Lactate production yield from engineered yeasts is dependent from the host background, the lactate dehydrogenase source and the lactate export", *Microbial Cell Factories*, 5(1): p. 4 (2006).
Dickson et al., "Yeast sphingolipids", *Biochimica et Biophysica Acta*, 1426(2): 347-357 (1999).
Sauer et al., "16 years research on lactic acid production with yeast—ready for the market?", *Biotechnology and Genetic Engineering Reviews*, 27(1): 229-256 (2010).
Yang et al., "Identification of mouse sphingomyelin synthase 1 as a suppressor of Bax-mediated cell death in yeast", *FEMS Yeast Research*, 6(5):751-762 (2006).
European Patent Office, Partial European Search Report for Application No. 16180739.1, dated Dec. 22, 2016, 10 pp.
Horvath et al., Metabolic link between phosphatidylethanolamine and triacylglycerol metabolism in the yeast *Saccharomyces cerevisiae*, *Biochimica et Biophysica Acta*, 1811: 1030-1037 (2011).
Kajiwara et al., Overexpression of the OLE1 gene enhances ethanol fermentation by *Saccharomyces cerevisiae*, *Applied Microbiology and Biotechnology*, 53(5): 568-574 (2000).
Kajiwara et al., Improved ethanol tolerance of *Saccharomyces cerevisiae* strains by increases in fatty acid unsaturation via metabolic engineering, *Biotechnology Letters*, 22: 1839-1843 (2000).
Zhang et al., Three diacylglycerol acyltransferases contribute to oil biosynthesis and normal growth in *Yarrowia lipolytica*, Yeast, 29: 25-38 (2012).

(Continued)

*Primary Examiner* — Iqbal H Chowdhury
(74) *Attorney, Agent, or Firm* — Leydig, Voit & Mayer, Ltd.

(57) ABSTRACT

Provided is an acid-tolerant yeast cell, a method of producing an organic acid by using the yeast cell, and a method of producing the yeast cell resistant to acid.

18 Claims, 9 Drawing Sheets

(56) References Cited

OTHER PUBLICATIONS

European Patent Office, Extended European Search Report for Application No. 16180739.1, dated Mar. 8, 2017, 20 pgs.

Yang et al. "Identification of mouse sphingomyelin synthase 1 as a suppressor of Bax-mediated cell death in yeast," *FEMS Yeast Res*, 6, pp. 751-762 (2006).

Kajiwara et al. "Overexpression of the OLE1 gene enhances ethanol fermentation of *Saccharomyces cerevisiae*," *Appl Microbiol Biotechnol*, 53, pp. 568-574 (2000).

European Office Action issued in EP 16 180 739.1 dated Feb. 13, 2018, 6 pages.

* cited by examiner

__US 10,053,714 B2__

ACID-TOLERANT YEAST CELL, METHOD OF PRODUCING ORGANIC ACID USING THE SAME, AND METHOD OF PRODUCING THE YEAST CELL

CROSS-REFERENCE TO RELATED APPLICATION

This application claims the benefit of Korean Patent Application No. 10-2015-0106771, filed on Jul. 28, 2015, in the Korean Intellectual Property Office, the disclosure of which is incorporated herein in its entirety by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 100,552 Byte ASCII (Text) file named "724478_ST25.txt," created on Jul. 28, 2016.

BACKGROUND

Organic acids are widely used in industrial fields. For example, lactate is an organic acid that is broadly used in various industrial fields such as food, pharmaceutics, chemicals, and electronics. Lactate is a low-volatile material that is colorless, odorless, and water-soluble. Lactate is non-toxic to the human body and thus may be used as a flavoring agent, a taste agent, or a preserving agent. Additionally, lactate is an environment-friendly alternative polymer material and a raw material of a polylactic acid (PLA), which is a biodegradable plastic.

Organic acids may be dissociated into hydronium ions and their own anions at a higher pH than their own dissociation constant (pKa), for example, under a neutral condition (e.g., a pH of about 7). Organic acids (e.g., lactic acid) may be present in the form of a free acid without an electromagnetic force at a pH lower than its own pKa value. The anion of an organic acid may not be permeable with respect to a cell membrane; however, the organic acid may be permeable with respect to the cell membrane when the organic acid is present in the form of a free acid. Thus, an organic acid in a free acid form may flow into the cells from extracellular environments where the concentration of the organic acid is high, thus lowering intercellular pH level.

Therefore, to produce an organic acid present as negative ions requires an additional isolation process involving the addition of a salt. Furthermore, cells lacking acid resistance may become inactive and nonviable under acidic conditions, such as in the case of lactic acid buildup within a cell. Thus, there is a need for microorganisms that are acid tolerant. This invention provides such microorganisms.

SUMMARY

The invention provides an acid-tolerant yeast cell, and a method of producing the acid-tolerant yeast cell. The invention also provides a method of producing an organic acid.

Additional aspects will be set forth in part in the description which follows and, in part, will be apparent from the description, or may be learned by practice of the presented exemplary embodiments.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
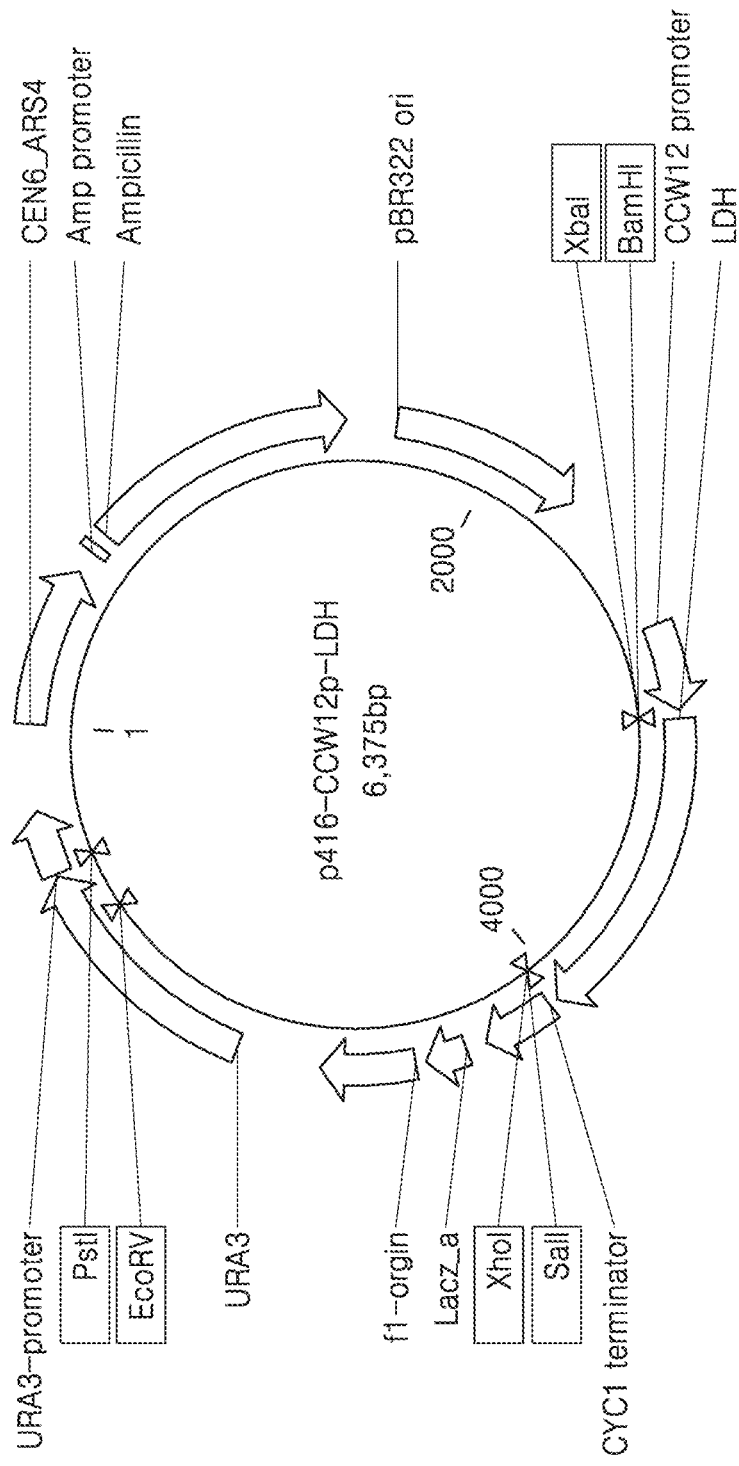
FIG. 1 is a schematic of the p416-CCW12p-LDH vector.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

As used herein, the term "increase in activity" or "increased activity" refers to any increase in activity of a cell, a protein or an enzyme. The term "activity increase" or "increased activity" may also refer to an increased activity level of a modified (e.g., genetically engineered) cell, protein, or enzyme compared to an activity level of a cell, protein, or enzyme of the same type without the given genetic modification (e.g., a comparable parent cell or wild-type cell, protein, or enzyme). The term "activity of cell" may refer to an activity of a particular protein or enzyme of a cell. For example, an activity of the modified or engineered cell, protein, or enzyme may be at least about 5%, at least about 10%, at least about 15%, at least about 20%, at least about 30%, at least about 50%, at least about 60%, at least about 70%, or at least about 100% increased compared to an activity of an unmodified or unengineered cell, protein, or enzyme of the same type, for example, a wild-type cell, protein, or enzyme. An activity of a particular protein or enzyme in a cell may be, for example, at least about 5%, at least about 10%, at least about 15%, at least about 20%, at least about 30%, at least about 50%, at least about 60%, at least about 70%, or at least about 100% increased compared to an activity of the same protein or enzyme in a parent cell, for example, an unmodified or unengineered cell. A cell having increased activity of a protein or enzyme may be confirmed by using any method commonly known in the art.

The increased activity of the enzyme or polypeptide may occur due to an increase in expression or an increase in specific activity. The increased expression may occur by introducing a polynucleotide encoding an enzyme or polypeptide into a cell repeatedly, or mutating a regulatory region of the polynucleotide. A yeast cell to which the gene is to be introduced may include a copy of the gene as an endogenous gene or may not include the gene as an endogenous gene.

The polynucleotide encoding an enzyme or polypeptide (used synonymously with the term "gene") may be operably linked to a control sequence that enables its expression, for example, a promoter, an enhancer, a polyadenylated site, or a combination thereof. A polynucleotide that is introduced or present in an increased copy number may be an exogenous gene. An endogenous gene refers to a gene that exists in a genetic material included in a microorganism. An exogenous gene refers to a gene that is introduced into a host cell, such as a gene that is integrated into a host cell genome, wherein the introduced gene may be homologous or heterologous with respect to the host cell genome. The term "heterologous" may refer that the gene may be foreign, not native.

The expression "increased copy number" may include a copy number increase by an introduction or amplification of the gene. The expression "increased copy number" may also include a copy number increase by genetically manipulating a cell that does not have a gene so as to have the gene in the cell. The introduction of the gene may occur by using a vehicle such as a vector. The introduction may be a transient introduction, in which the gene is not integrated into the genome, or a stable introduction, in which the gene is integrated into the genome. The introduction may, for example, occur by introducing a vector inserted with a polynucleotide encoding a desired polypeptide into the cell and then replicating the vector in the cell or integrating the polynucleotide into the genome of the cell and then replicating the polynucleotide together with the replication of the genome.

Introduction of the gene may be performed by using methods known in the art such as transformation, transfection, and electroporation. The gene may be introduced by a vehicle or may be introduced as itself. As used herein, the term "vehicle" refers to a nucleic acid molecule that may deliver another nucleic acid linked thereto. In terms of a nucleic acid that mediates introduction of a specific gene, it is understood the term "vehicle" used herein may be alternatively used with a vector, a nucleic acid structure, and a cassette. A vector may include, for example, a plasmid or virus-derived vector. Plasmid refers to a circular double stranded DNA circle to which an additional DNA may be linked. A vector may include, for example, a plasmid expression vector or a virus expression vector, or replication-defective retrovirus, adenovirus, and adeno related virus, or a combination thereof. A yeast expression vector may be a vector for expression of Saccaromyces cerevisea, examples of yeast expression vectors include pYepSec1, 2i, pAG-1, Yep6, Yep13, PEMBLYe23, pMFa, pJRY88, or pYES2.

As used herein, the gene manipulation and engineering may be performed by molecular biological methods known in the art (Roslyn M. Bill, Recombinant Protein Production in Yeast: Methods and Protocols (2012), R Daniel Gietz et al., Quick and easy yeast transformation using the LiAc/SS carrier DNA/PEG method: Nature protocols (2007)).

As used herein, an "inactivated" or "decreased" activity of an enzyme or a polypeptide, or an enzyme having an activity that is "inactivated" or "reduced" denotes a cell having an activity that is lower than an activity of an enzyme or polypeptide measured in a cell of the same type of parent cell (e.g., genetically non-engineered). Also, the "inactivated" or "decreased" activity refers to an isolated enzyme or polypeptide that has an activity that is lower than an activity of the original or wild-type enzyme or polypeptide. The "inactivated" or "decreased" activity includes no activity. For example, an enzyme activity of converting a substrate to a product with respect to a modified (e.g., genetically engineered) cell or enzyme may about 20% or more, about 30% or more, about 40% or more, about 50% or more, about 55% or more, about 60% or more, about 70% or more, about 75% or more, about 80% or more, about 85% or more, about 90% or more, about 95% or more, or about 100% reduced compared to the enzyme activity of a cell or enzyme that is not modified, or, for example, a parent cell or wild-type cell or enzyme. The cells having reduced activity of the enzyme may be confirmed by using a commonly known method in the art.

The inactivation or decrease includes the case when a gene-encoding an enzyme is not expressed or has decreased expression compared to a cell expressing the unmodified gene, for example, a parent cell or wild-type cell.

As used herein, the term "parent cell" denotes an original cell that is genetically modified to produce a genetically engineered cell (e.g., a non-genetically engineered cell of the same type as the genetically engineered cell, but without a give genetic modification). In terms of a specific genetic modification, the "parent cell" does not have the specific genetic modification, but the cell may be the same in regard of other conditions. Therefore, the parent cell may be used as a starting material to produce a genetically engineered yeast cell having an inactivated or reduced activity of a given protein (e.g., a protein having at least about 95% sequence identity with DGA1 or LRO1) or a genetically engineered yeast cell having an increased activity of a given protein (e.g., a protein having at least about 95% sequence identity with AUR1 or OLE1). In addition, with respect to the yeast cell having a reduced activity of DGA1 or LRO1 in a cell where a DGA1 or LRO1 encoding gene is modified, the parent cell may be a yeast cell that includes an unmodified, "wild-type" DGA1 or LRO1 gene. The same type of comparison is applied to other genetic modifications.

Activity of the enzyme may be inactivated or reduced due to deletion or disruption of a gene that encodes the enzyme. As used herein, the "deletion" or "disruption" of the gene includes mutation or deletion of the gene or a regulatory region of the gene (e.g., operator, promoter or terminator regions of the gene), or a part thereof, sufficient to disrupt or delete gene function or the expression of a functional gene product compared to the unmodified gene. Mutations include addition, substitution, insertion, deletion, or conversion of one or more nucleotide(s) of the gene. The deletion or disruption of the gene may be accomplished by any suitable genetic engineering technique, such as homologous recombination, directed mutagenesis, or molecular evolution. When a cell includes a plurality of copies of the same gene or at least two different polypeptide paralogs, at least one gene may be deleted or disrupted. For example, inactivation or destruction of the enzyme may be caused by homologous recombination or the inactivation or destruption of the enzyme may be performed by transforming a vector including a partial sequence of the gene in the cell, culturing the cell so that the sequence may homologously recombine with an endogenous gene of the cell to delete or disrupt the gene, and isolating the cell in which the homologous recombination occurred by a selection marker.

As used herein, the term "gene" refers to a nucleic acid fragment expressing a specific protein and may optionally include a regulatory sequence such as a 5'-non-coding sequence and/or a 3'-non-coding sequence.

As used herein, the term "sequence identity" of a nucleic acid or polypeptide with respect to another nucleic acid or polypeptide refers to a degree of sameness in a base or amino acid residue in a specific region of two sequences that are aligned to best match each other for comparison. The sequence identity is a value obtained via optimal alignment and comparison of the two sequences in the specific region for comparison, in which a partial sequence in the specific region for comparison may be added or deleted with respect to a reference sequence. The sequence identity represented in a percentage may be calculated by, for example, comparing two sequences that are aligned to best match each other in the specific region for comparison, determining matched sites with the same amino acid or base in the two sequences to obtain the number of the matched sites, dividing the number of the matched sites in the two sequences by a total number of sites in the compared specific regions (i.e., a size of the compared region), and multiplying a result of the division by 100 to obtain a sequence identity as a percentage. The sequence identity as a percentage may be determined using a known sequence comparison program, for example, BLASTN (NCBI), BLASTP (NCBI), CLC Main Workbench (CLC bio), or MegAlign™ (DNASTAR Inc). For example, the sequence identity as a percentage may be determined using a sequence alignment program BLASTN (NCBI), or BLASTP (NCBI) with the following choice of parameters: Ktuple=2, Gap Penalty=4, and Gap Length Penalty=12.

In some embodiments of the invention, to identify a polypeptide or polynucleotide with the same or similar function the polypeptide or polynucleotide may have an amino acid sequence with a sequence identity of, for example, 50% or greater, 55% or greater, 60% or greater, 65% or greater, 70% or greater, 75% or greater, 80% or greater, 85% or greater, 90% or greater, 95% or greater, 96% or greater, 97% or greater, 98% or greater, 99% or greater, or 100%, with respect to the other polypeptide or polynucleotide compared.

As used herein, the term "genetic modification" includes an artificial change in a component or a structure of a genetic material of a cell.

As used herein, unless described otherwise, an organic acid may be used alternatively with an organic acid in the form of an anion, in which hydronium ion is dissociated, as well as an organic acid in a neutral state. For example, a lactic acid may be alternatively used with a lactate.

According to an embodiment, provided is a yeast cell resistant to acid, wherein the yeast cell includes a genetic modification that increases the activity of an enzyme, which catalyzes conversion of phosphatidylinositol (PI) and ceramide into inositol phosphorylceramide (IPC) and diacylglycerol (DG); a genetic modification that increases activity of an enzyme, which catalyzes introduction of a double bond to a fatty acyl site of a fatty acyl-CoA; or a combination thereof; and/or genetic modification that decreases activity of an enzyme, which catalyzes formation of triacylglycerol (TG) from diacylglycerol (DG).

The enzyme, which catalyzes the conversion of phosphatidylinositol (PI) and ceramide to IPC and DG, may deliver a phosphorylinositol group from PI to a C1 hydroxyl group of ceramide leading to the formation of IPC and DG. The ceramide may be a long-chain or sphingoid base linked to a fatty acid via an amide bond. For example, the sphingoid base may be various di- or tri-hydroxy sphingoid base, and a fatty acid in the sphingoid base may comprise saturated and monoenoic fatty acid with 16 or more carbons, wherein the fatty acid optionally has a hydroxyl group at position 2.

For example, the enzyme, which catalyzes conversion of phosphatidylinositol (PI) and ceramide to IPC and DG, may catalyze the reaction below.

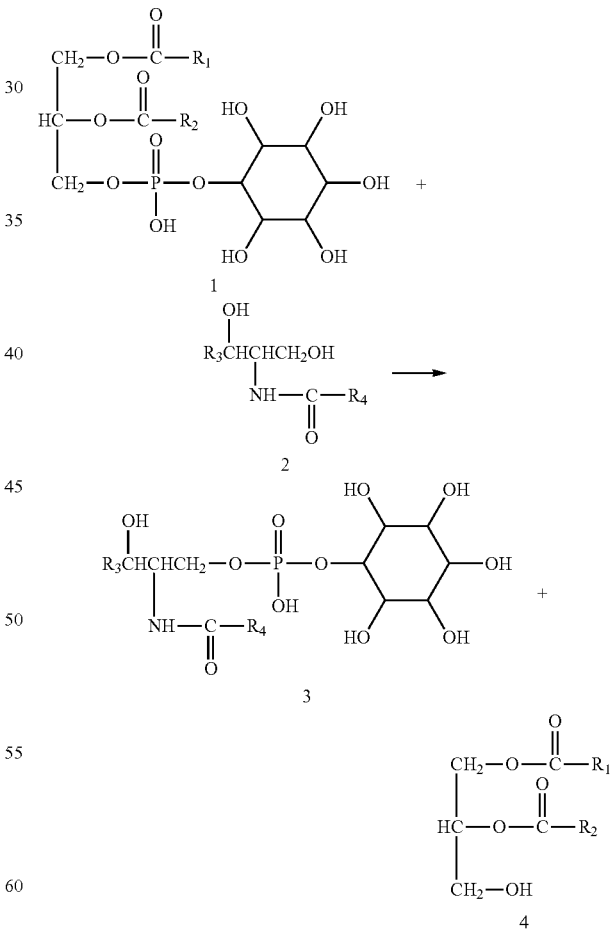

In Scheme 1, $R_1$ and $R_2$ in PI(1) and DG(4) may be parts that are derived from a fatty acid except a carbonyl group of the fatty acid. $R_1$ and $R_2$ may be each independently a linear or branched, saturated or unsaturated, optionally, mono- or polyhydroxylated, C1-C50, or, for example, C5-C50, C5-C35, C13-C33, or C13-C25 hydrocarbon radical. Here, $R_1$ and $R_2$ may each independently have one, two, or three double bonds, and/or may have one, two, three, or four hydroxyl groups. $R_3$ and $R_4$ in ceramide (2) and IPC (3) are each independently a linear or branched, saturated or unsaturated, optionally, mono- or polyhydroxylated, C1-C50, or, for example, C5-C50, C5-C35, C13-C33, or C13-C25 hydrocarbon radical. In some embodiments, $R_3$ and $R_4$ in ceramide (2) and IPC (3) are each independently a linear saturated or unsaturated, optionally, hydroxylated, C13-C25 or C15-C25 alkyl radical. Here, $R_3$ and $R_4$ may each independently have one, two, or three carbon-carbon double bonds, and/or may have one, two, three, or four hydroxyl groups. In some embodiments, in ceramide (2) and IPC (3), $R_3$ is a C13-C15 alkyl radical that has hydroxylated carbon at the position 1 a double bond between carbon at the position 1 and carbon at the position 2 when a carbon participated in linking is considered as at the position 1, and $R_4$ is a C16-C25 alkyl radical in which carbon at the position 1 and/or carbon at the position 2 are optionally hydroxylated when a carbon participated in linking is considered as at the position 1. When a carbon participated in linking is considered as at the position 1, $R_4$ may be a C25 alkyl radical having a hydroxylated carbon at the position 1. The ceramide may be phytoceramide.

The enzyme that catalyzes conversion of phosphatidylinositol (PI) and ceramide to IPC and DG includes an IPC synthase or a subunit thereof. The enzyme may be IPC synthase catalytic subunit AUR1. AUR1 may be a polypeptide including an amino acid sequence having at least 95% of sequence identity with an amino acid sequence of SEQ ID NO: 1. A polynucleotide that encodes AUR1 may include a polynucleotide encoding an amino acid sequence having at least 95% of sequence identity with an amino acid sequence of SEQ ID NO: 1 or a nucleotide sequence of SEQ ID NO: 2. AUR1 may synthesize IPC by transferring a myo-inositol phosphate group to a C1-hydroxyl group of ceramide or phytoceramide from PI while releasing DG. The phytoceramide is a fatty acid which may be a C26 fatty acid having a hydroxyl group at the position 2.

In terms of the enzyme that catalyzes introduction of a double bond to a fatty acyl site of a fatty acyl-CoA, the fatty acyl group may be a fatty acid having any number of carbons found in the body. The number of carbons in the fatty acyl group may be 14 to 50, 14 to 40, 14 to 36, 14 to 30, 14 to 26, 16 to 30, or 16 to 24. The enzyme may belong to an enzyme code (EC) 1.14.19.1. The enzyme may be acyl-CoA desaturase1 (OLE1). OLE1 may be a polypeptide that has an amino acid sequence having at least 95% sequence identity with an amino acid sequence of SEQ ID NO: 3 or 5. A polynucleotide that encodes OLE1 may be a polynucleotide that encodes an amino acid having at least 95% of sequence identity with an amino acid sequence of SEQ ID NO: 3 or 5 or a nucleotide sequence of SEQ ID NO: 4 or 6.

In terms of the enzyme that catalyzes synthesis of triacylglycerol (TG) from diacylglycerol (DG), an acyl group included in DG or TG may have an acyl group having any number of carbons found in the body. The number of carbons in the acyl group may be 14 to 50, 14 to 40, 14 to 36, 14 to 30, 14 to 26, 16 to 30, or 16 to 24. DG may be sn1,2 or sn1,3 DG. The enzyme may be selected from the group consisting of enzymes that belong to EC 2.3.1.22 and EC 2.3.1.158. The enzyme may be diacylglycerol O-acyltransferase 1 (DGA1) or phospholipid:diacylglycerol acyltransferase (LRO1). DGA1 may catalyze a reaction represented by acyl-CoA+1,2-diacylglycerol->CoA+triacylglycerol. LRO1 produces TG via an acyl-CoA independent pathway. LRO1 may synthesize sn-1-lysophospholipid and triacylglycerol by specifically transferring an acyl group to diacylglycerol from the position sn-2 of phospholipid. LRO1 may catalyze a reaction represented by phospholipid+1,2-diacylglycerol->lysophospholipid+triacylglycerol.

DGA1 and LRO1 may be each independently a polypeptide that has an amino acid sequence having at least 95% of sequence identity with an amino acid sequence of SEQ ID NO: 7 or 9. A polynucleotide that encodes DGA1 or LRO1 may be a polynucleotide that encodes an amino acid sequence having at least 95% of sequence identity with an amino acid sequence of SEQ ID NO: 7 or 9 or may have a nucleotide sequence of SEQ ID NO: 8 or 10.

In the yeast cell, the genetic modification increases expression of a gene that encodes an enzyme, which catalyzes synthesis of IPC, a gene that encodes an enzyme, which catalyzes introduction of a double bond to a fatty acyl site of a fatty acyl-CoA, or a combination thereof, or a gene that encodes an enzyme, which catalyzes synthesis of triacylglycerol TG from diacylglycerol DG may be removed or disrupted.

In the yeast cell, the genetic modification increases the copy number of a gene that encodes a polypeptide having at least 95% of sequence identity with an amino acid sequence of SEQ ID NO: 1, 3, or 5, or a gene that encodes a polypeptide having at least 95% of sequence identity with an amino acid sequence of SEQ ID NO: 7 or 9 may be removed or disrupted.

The yeast cell may be acid tolerant. As used herein, the term "acid tolerant" refers to an organism that have an increased cell growth under an acid conditions compared to a cell growth of a cell that is not genetically engineered. The acid conditions may include an organic acid, an inorganic acid, or a combination thereof. The organic acid may include C1 to C20, for example, C1 to C18, C1 to C16, C1 to C14, C1 to C12, C1 to C10, C1 to C8, C1 to C6, C2 to C18, C3 to C16, C2 to C14, C3 to C12, C2 to C10, C2 to C8, or C2 to C6. The organic acid may be acetic acid, lactic acid, propionic acid, butyric acid, 4-hydroxybutyric acid, succinic acid, fumaric acid, malic acid, oxalic acid, or a combination thereof. Growth of the yeast cell may be increased under a condition of pH 2.0 to 7.0, for example, pH 2.0 to 5.0, pH 2.0 to 4.0, pH 2.0 to 3.8, pH 2.5 to 3.8, pH 3.0 to 3.8, pH 2.0 to 3.0, pH 2.0 to 2.5, or pH 2.5 to 3.0 compared to the cell growth of a yeast cell that is not genetically engineered.

Also, the term "acid tolerant" used herein may refer to organisms that have a higher survival rate under an acidic condition compared to a survival rate of a cell that is not genetically engineered. The acidic condition may include an organic acid, an inorganic acid, or a combination thereof. The organic acid may include C1 to C20, for example, C1 to C18, C1 to C16, C1 to C14, C1 to C12, C1 to C10, C1 to C8, C1 to C6, C2 to C18, C3 to C16, C2 to C14, C3 to C12, C2 to C10, C2 to C8, or C2 to C6. The organic acid may be acetic acid, lactic acid, propionic acid, butyric acid, 4-hydroxybutyric acid, succinic acid, fumaric acid, malic acid, oxalic acid, or a combination thereof. The yeast cell may better survive under a condition of pH 2.0 to 7.0, for example, pH 2.0 to 5.0, pH 2.0 to 4.0, pH 2.0 to 3.8, pH 2.5 to 3.8, pH 3.0 to 3.8, pH 2.0 to 3.0, pH 2.0 to 2.5, or pH 2.5 to 3.0 compared to the survival of a yeast cell that is not genetically engineered.

Also, the term "acid tolerant" used herein may refer to organisms that have a better metabolic process under an acidic condition compared to that of a cell that is not genetically engineered. The acidic condition may include an organic acid, an inorganic acid, or a combination thereof. The organic acid may include 01 to 020, for example, C1 to C18, C1 to C16, C1 to C14, C1 to C12, C1 to C10, C1 to C8, C1 to C6, C2 to C18, C3 to C16, C2 to C14, C3 to C12, C2 to C10, C2 to C8, or 02 to C6. The organic acid may be acetic acid, lactic acid, propionic acid, butyric acid, 4-hydroxybutyric acid, succinic acid, fumaric acid, malic acid, oxalic acid, or a combination thereof. Metabolizm of the yeast cell may better under a condition of pH 2.0 to 7.0, for example, pH 2.0 to 5.0, pH 2.0 to 4.0, pH 2.0 to 3.8, pH 2.5 to 3.8, pH 3.0 to 3.8, pH 2.0 to 3.0, pH 2.0 to 2.5, or pH 2.5 to 3.0 compared to that of a yeast cell that is not genetically engineered. Here, a degree of "metabolism" may be measured by a nutrition absorbing rate per cell, or, for example, a glucose absorbing rate per cell. Also, a degree of "metabolism" may be measured by a product yield rate per cell, or, for example, a carbon dioxide release rate per cell.

The yeast cell may be a modified yeast cell having increased productivity of a product, for example, an organic acid, such as lactate, as well as a naturally occurring yeast cell. In the modified yeast cell, activity of a protein involved in the synthesis of, for example, the product (e.g., an organic acid) may be increased. For example, in the modified yeast cell, a gene that encodes a protein involved in the synthesis of the product may be introduced, an internal gene may be amplified to increase expression of the gene, or the internal gene or the regulatory sequence may be modified. Also, the modified yeast may have an inactivated or reduced gene that encodes a protein related to decomposition of the product.

The product may be an organic acid, a protein, a fat, or a sugar. The product may be present as a free compound without charges, for example, negative charges, at a specific level of acidity or less. Accordingly, it may be unnecessary to convert the product into the form of a salt by using counter ions in order to isolate the product. The product may be an organic acid. The organic acid may be a C1 to C20 organic acid, for example, a C1 to C18, C1 to C16, C1 to C14, C1 to C12, C1 to C10, C1 to C8, C1 to C6, C2 to C18, C3 to C16, C2 to C14, C3 to C12, C2 to C10, C2 to C8, or C2 to C6 organic acid. The organic acid may be acetic acid, lactic acid, propionic acid, butyric acid, 4-hydroxybutyric acid, succinic acid, fumaric acid, malic acid, citric acid, oxalic acid, or a combination thereof. The organic acid may not have an unsaturated bond, for example, a double bond or a triple bond, between carbons in a molecule.

The yeast cell may have an ability to produce lactate. In the yeast cell, activity of a protein involved in the synthesis of lactic acid may be increased. The increase may be caused by an increase in expression of a gene that encodes a protein related to the lactate synthesis. The increase may be, for example, due to introduction of a gene encoding a protein related to the lactate synthesis, amplification of an internal gene to increase expression of the gene, or modification of the internal gene or its regulatory sequence. The increase may be about 5% or more, about 10% or more, about 15% or more, about 20% or more, about 30% or more, about 50% or more, about 60% or more, about 70% or more, or about 100% or more increased than lactate synthesis of the control group.

The protein related to lacate synthesis may be involved in activity of converting pyruvate to lactate, that is, the protein may be a lactate dehydrogenase. The increase in activity of lactate dehydrogenase may be sufficient enough to produce lactate.

As used herein, the term "lactate dehydrogenase (LDH)" may be an enzyme that catalyzes conversion of pyruvate to lactate. The lactate dehydrogenase may be a NAD(P)-dependent enzyme and may act on L-lactate or D-lactate. The NAD(P)-dependent enzyme may be an enzyme that may be classified as EC 1.1.1.27 which acts on L-lactate or as EC 1.1.1.28 which acts on D-lactate. The lactate dehydrogenase may have an amino acid sequence of SEQ ID NO: 11. A gene that encodes the lactate dehydrogenase may have a nucleotide sequence of SEQ ID NO: 12. A lactate dehydrogenase of SEQ ID NO: 11 and a polynucleotide of SEQ ID NO: 12 that encodes the lactate dehydrogenase are derived from *Sordaria macrospora*. The lactate dehydrogenase may have an amino acid sequence of SEQ ID NO: 13. A gene that encodes the lactate dehydrogenase may have a nucleotide sequence of SEQ ID NO: 14. A lactate dehydrogenase of SEQ ID NO: 13 and a polynucleotide of SEQ ID NO: 14 that encodes the lactate dehydrogenase are derived from *Pelodiscus sinensis japonicus*.

The yeast cell may include a polynucleotide that encodes a single LDH and a polynucleotide that encodes a plurality of LDHs, for example, 2 to 10 copies of LDHs. The yeast cell may include, for example, 1 to 10, 1 to 8, 1 to 7, 1 to 6, 1 to 5, 1 to 4, 1 to 3, 2 to 10, 2 to 8, 2 to 7, 2 to 6, 2 to 5, 2 to 4, or 2 to 3 copies of LDH genes. When the yeast cell includes a polynucleotide that encodes a plurality of LDHs, the polynucleotide may be a copy of the same polynucleotide or may include copies of a polynucleotide that encodes at least two different LDHs. A plurality of copies of a polynucleotide that encodes an exogenous LDH may be included in the same locus or several loci in genome of the host cell.

Also, in the yeast, an activity of a protein related to decomposition of lactate may be removed or reduced. The removal or reduction may denote inactivation or attenuation of a gene that encodes a protein related to decomposition of lactate. The protein related to decomposition of lactate may be a polypeptide having activity of converting pyruvate to acetaldehyde, for example, pyruvate decarboxylase (PDC), a polypeptide having a activity of converting lactate to pyruvate, for example, a lactate cytochrome-c oxidoreductase (CYB2), a polypeptide that converts dihydroxyacetone phosphate (DHAP) to glycerol-3-phosphate, for example, cytosolic glycerol-3-phosphate dehydrogenase (GPD1), or a combination thereof. The reduction of activity may be about 10% or more, about 20% or more, about 30% or more, about 40% or more, about 50% or more, about 55% or more, about 60% or more, about 70% or more, about 75% or more, about 80% or more, about 85% or more, about 90% or more, about 95% or more, or about 100% or more reduced compared to an activity of the control group.

A polypeptide having an activity of converting pyruvate to acetaldehyde may be an enzyme classified into EC 4.1.1.1. The polypeptide converting pyruvate to acetaldehyde may have an amino acid sequence of SEQ ID NO: 15. A gene that encodes a polypeptide converting pyruvate to acetaldehyde may have a nucleotide sequence of SEQ ID NO: 16. The gene may be pdc1 or pdc2 that encodes a pyruvate decarboxylase (PDC). PDC of SEQ ID NO: 15 and a polynucleotide of SEQ ID NO: 16, which encodes PDC are derived from *Saccharomyces cerevisea*.

The polypeptide having activity of converting lactate to pyruvate may be a cytochrome c-dependent enzyme. The polypeptide having activity of converting lactate to pyruvate may be a lactate cytochrome-c oxidoreductase (CYB2). The lactate cytochrome-c oxydoreductase may be an enzyme that is classified into EC 1.1.2.4, which acts on D-lactase, or EC 1.1.2.3, which acts on L-lactase. The polypeptide converting lactate to pyruvate may have an amino acid sequence of SEQ ID NO: 17. A gene that encodes the polypeptide converting lactate to pyruvate may have a nucleotide sequence of SEQ ID NO: 18. CYB2 of SEQ ID NO: 17 and a polynucleotide of SEQ ID NO: 18, which encodes CYB2 are derived from *Saccharomyces cerevisea*.

The polypeptide having an activity of converting dihydroxyacetone phosphate to glycerol-3-phosphate may be an enzyme that catalyzes reduction of DHAP to glycerol-3-phosphate by using oxidation of NADH to NAD+. The enzyme may be classified into EC 1.1.1.8. The polypeptide may be a cytosolic glycerol-3-phosphate dehydrogenase (GPD1). The polypeptide converting dihydroxyacetone phosphate to glycerol-3-phosphate may have an amino acid sequence of SEQ ID NO: 19. A gene that encodes the polypeptide converting dihydroxyacetone phosphate to glycerol-3-phosphate may have a nucleotide sequence of SEQ ID NO: 20. The gene may be gdp1 encoding glycerol-3-phosphate dehydrogenase.

In the yeast cell, an activity of an external mitochondrial NADH dehydrogenase may be inactivated or reduced to a degree that is sufficient to produce an organic acid, such as lactate or improve an organic acid, such as lactate productivity of the yeast cell that produces an organic acid, such as lactate.

The external mitochondrial NADH dehydrogenase may be an enzyme classified into EC 1.6.5.9 or EC 1.6.5.3. The NADH dehydrogenase may be a type II NADH:ubiquinone oxidoreductase. The NADH dehydrogenase may be located on a superficial surface of an interal mitochondria membrane facing cytoplasm. The NADH dehydrogenase may be an enzyme that catalyzes oxidation of cytosolic NADH to NAD+. The NADH dehydrogenase may reoxidize cytosolic NADH formed by the corresponding process. The NADH dehydrogenase may provide cytosolic NADH to a mitochondrial respiratory chain. The NADH dehydrogenase may be NDE1, NDE2, or a combination thereof. The NADH dehydrogenase may be different from an internal mitochondrial NADH dehydrogenase (NDI1) that is located and functions in the mitochondria. NDE1 and NDE2 may each independently have at least about 75%, at least about 80%, at least about 85%, at least about 90%, at least about 95%, at least about 96%, at least about 97%, at least about 98%, at least about 99%, or about 100% of sequence identity with amino acid sequences of SEQ ID NOS: 21 and 22. A gene encoding NDE1 and a gene encoding NDE2 may each independently have at least about 75%, at least about 80%, at least about 85%, at least about 90%, at least about 95%, at least about 96%, at least about 97%, at least about 98%, at least about 99%, or about 100% of sequence identity with nucleotide sequences of SEQ ID NOS: 23 and 24.

The yeast cell may include genetic modification that increases an activity of an enzyme, which catalyzes conversion of phosphatidylinositol (PI) and ceramide to inositol phosphorylceramide (IPC) and diacylglycerol (DG) in a yeast cell, which is Accession No. KCTC 12415 BP; genetic modification that increases an activity of an enzyme, which catalyzes introduction of a double bond to a fatty acyl site of fatty acyl-CoA; or a combination thereof; and/or genetic modification that decreases an activity of an enzyme, which catalyzes synthesis of triacylglycerol (TG) from diacylglycerol (DG); and a genetic modification that reduces activity of external mitochondrial NADH dehydrogenase NDE1 and/or NDE2.

According to another embodiment, provided is a method of producing an organic acid, wherein the method includes producing a culture by culturing the genetically engineered yeast cell in a medium; and collecting an organic acid from the culture, wherein the yeast cell further has a genetic modification that increases an activity of an enzyme, which catalyzes synthesis of the organic acid.

The method includes culturing the acid-tolerant yeast cell in a medium. The acid-tolerant yeast cell is the same as defined in the description above.

The culturing may be performed in a medium containing a carbon source, for example, glucose. The medium used in culture of a yeast cell may be a common medium suitable for growth of a host cell such as a minimal or composite medium containing appropriate supplements. A suitable medium may be purchased from commercial suppliers or may be prepared according to a known preparation method.

The medium used in the culturing may be a medium that satisfies particular conditions for growing a yeast cell. The medium may be one selected from the group consisting of a carbon source, a nitrogen source, a salt, trace elements, and a combination thereof.

The culturing condition for obtaining lactate from the genetically engineered yeast cell may be appropriately controlled. The culturing may be performed in an aerobic or anaerobic condition. For example, the yeast cell is cultured under an aerobic condition for its proliferation, and then, the yeast cell is cultured under an anaerobic condition or a microaerobic condition to produce an organic acid such as lactate. The anaerobic condition may include a microaerobic condition having a dissolved oxygen (DO) concentration of 0% to 10%, for example, 0 to 8%, 0 to 6%, 0 to 4%, 0 to 2%, 0.1% to 10%, 1% to 10%, 2% to 10%, 3% to 10%, 4% to 10%, 5% to 10%, 6% to 10%, 7% to 10%, 8% to 10%, 9% to 10%, 1% to 8%, 2% to 8%, 3% to 8%, 4% to 8%, 5% to 8%, 6% to 8%, 7% to 8%, 1% to 6%, 2% to 6%, 3% to 6%, 4% to 6%, 5% to 6%, 1% to 5%, 2% to 5%, 2% to 4%, or 2% to 5%.

The term "culture condition" indicates a condition for culturing a yeast cell. Such culture condition may be, for example, a carbon source, a nitrogen source, or an oxygen condition for the yeast cell to use. The carbon source used by the yeast cell includes monosaccharides, disaccharides, or polysaccharides. In particular, the carbon source may be glucose, fructose, mannose, or galactose. The nitrogen source used by the yeast cell may include an organic nitrogen compound or an inorganic nitrogen compound. In particular, the nitrogen source may be an amino acid, amide, amine, a nitrate, or an ammonium salt. The oxygen condition for culturing the yeast cell includes an aerobic condition of a normal oxygen partial pressure, a low-oxygen condition including 0.1% to 10% of oxygen in the atmosphere, or an anaerobic condition without oxygen. A metabolic pathway may be modified in accordance with the carbon source or the nitrogen source that may be practically used by the yeast cell.

The culturing may be performed under an acidic condition for the entire time period of culturing or part of the time period of culturing. The acidic condition may be in a pH range of about 2.0 to about 7.0, or, for example, about 2.0 to about 5.0, about 2.0 to about 4.0, about 2.0 to about 3.8, about 2.5 to about 3.8, about 3.0 to about 3.8, about 2.0 to about 3.0, about 2.0 to about 2.5, or about 2.5 to about 3.0.

The product may be an organic acid, a protein, a fat, or a sugar. The product may be present as a free compound without charges, for example, negative charges, at a specific level of acidity or less. Accordingly, it may be unnecessary to convert the product into the form of a salt by using counter ions in order to isolate the product. The product may be an organic acid. The organic acid may be a C1 to C20 organic acid, for example, a C1 to C18, C1 to C16, C1 to C14, C1 to C12, C1 to C10, C1 to C8, C1 to C6, C2 to C18, C3 to C16, C2 to C14, C3 to C12, C2 to C10, C2 to C8, or C2 to C6 organic acid. The organic acid may be acetic acid, lactic acid, propionic acid, butyric acid, 4-hydroxybutyric acid, succinic acid, fumaric acid, malic acid, citric acid, oxalic acid, or a combination thereof. The organic acid may not have an unsaturated bond, for example, a double bond or a triple bond, between carbons in a molecule.

The method of producing an organic acid includes isolating the product from the culture. The isolating of the product may be performed using a suitable method selected depending on the product. The isolating of the product may include isolating the product in the form of a free compound, such as a free acid, but not a salt form, from the culture.

In the method of producing an organic acid, the yeast cell may be a yeast cell with Accession No. KCTC 12415 BP including a genetic modification of increasing an activity of an enzyme, which catalyzes conversion of PI and ceramide to IPC and DG, genetic modification of increasing an activity of an enzyme, which catalyzes introduction of a double bond to a fatty acyl site of fatty acyl-CoA, or a combination thereof, and/or genetic modification of decreasing an activity of an enzyme, which catalyzes synthesis of TG from DG, and may optionally further including a genetic modification that reduces activity of external mitochondrial NADH dehydrogenase NDE1 and/or NDE2, wherein the yeast cell is capable of producing lactic acid.

According to another embodiment, a method of producing an acid-tolerant yeast cell includes introducing a genetic modification that increases activity of an enzyme which catalyzes conversion of phosphatidylinositol (PI) and ceramide to inositol phosphorylceramide (IPC) and diacylglycerol (DG), a genetic modification that increases activity of an enzyme which catalyzes introduction of a double bond into a fatty acyl site of fatty acyl Co-A, or a combination thereof, and/or a genetic modification that decreases activity of an enzyme which catalyzes synthesis of triacylglycerol (TG) from diacylglycerol (DG).

The yeast cell may belong to phylum Ascomycota. The phylum Ascomycota may include family Saccharomycetaceae. The Saccharomycetaceae may be, for example, genus *Saccharomyces*, genus *Kluyveromyces*, genus *Candida*, genus *Pichia*, genus *Issatchenkia*, genus *Debaryomyces*, genus *Zygosaccharomyces*, or genus *Saccharomycopsis*. The genus *Saccharomyces* may be, for example, *S. cerevisiae*, *S. bayanus*, *S. boulardii*, *S. bulderi*, *S. cariocanus*, *S. cariocus*, *S. chevalieri*, *S. dairenensis*, *S. ellipsoideus*, *S. eubayanus*, *S. exiguus*, *S. florentinus*, *S. kluyveri*, *S. martiniae*, *S. monacensis*, *S. norbensis*, *S. paradoxus*, *S. pastorianus*, *S. spencerorum*, *S. turicensis*, *S. unisporus*, *S. uvarum*, or *S. zonatus*. The genus *Kluyveromyces* may be, for example, *K. thermotolerans*. The genus *Candida* may be, for example, *C. glabrata*. The genus *Zygosaccharomyces* may be, for example, *Z. bailli* or *Z. rouxii*. In some embodiments, the yeast cell may be *Saccharomyces cerevisiae*. The yeast cell may be a yeast cell with Accession No. KCTC12415 BP.

The method of producing an acid-tolerant yeast cell may further include introducing a genetic modification that reduces activity of external mitochondrial NADH dehydrogenase NDE1 and/or NDE2 into the yeast cell.

In the method of producing an acid-tolerant yeast cell, the genetic modification may include amplifying the gene, manipulating a regulatory sequence of the gene, or manipulating a sequence of the gene itself. The genetic modification may include inserting, substituting, converting, or adding a nucleotide.

The method of producing an acid-tolerant yeast cell may further include introducing a genetic modification that enables a starting yeast cell to have a capability of producing a product, for example, an organic acid such as lactate. For example, the methods may include introducing a genetic modification that increases activity of a protein involved in the synthesis of the product (e.g., an organic acid) to the starting yeast cell. For example, the genetic modification may be performed by introducing a gene that encodes a protein involved in the synthesis of the product, amplifying an internal gene to increase expression of the gene, or mutating the internal gene or its regulatory sequence. Also, the method may further include introducing a genetic modification that inactivates or decreases activity of a gene encoding a protein involved in decomposition of the product to the starting yeast cell.

Hereinafter, example embodiments will be described in detail with reference to the examples below. The examples have been provided for purposes of illustration only and are not to be construed to limit example embodiments.

EXAMPLE 1

Preparation of Strain for Highly Efficient Production of Lactate

In order to block a production pathway of ethanol and glycerol as main byproducts by using *Saccharomyces cerevisiae* CEN.PK2-1D (MATα ura3-52; trp1-289; leu2-3, 112; his3Δ1; MAL2-8$^c$; SUC2, EUROSCARF accession number: 30000B) as a lactate production strain, the following genes were inactivated by homologous recombination: a pyruvate decarboxylase (pdc1) gene, which is a main enzyme of alcohol fermentation; a NAD-dependent glycerol-3-phosphate dehydrogenase (gpd1) gene, which is a main enzyme of glycerol biosynthesis; and a L-lactate cytochrome-c oxidoreductase 2 (cyb2) gene, which is a lactate degrading enzyme. Also, an ldh gene was introduced to a trp1 site, and nde1 and nde2 genes were inactivated.

1. Preparation of Strain with Overexpressed L-LDH and Inactivated Pdc1, Gpd1, and Cyb2 Genes (1) Preparation of a L-LDH Overexpression Vector A CCW12 promoter polymerase chain reaction (PCR) fragment obtained by performing PCR with a genomic DNA of *Saccharomyces cerevisiae* CEN.PK2-1D as a template and using primers of SEQ ID NO: 25 and SEQ ID NO: 26 was digested with SacI and XbaI, and the resultant polynucleotide was inserted into a p416-GPD vector (ATCC 87360™) digested with SacI and XbaI, thereby producing a p416-CCW12p vector suitable for overexpression of L-ldh.

The L-Idh gene (SEQ ID NO: 14) was amplified from *Pelodiscus sinensis japonicus* genomic DNA by PCR using primers of SEQ ID NO: 32 and SEQ ID NO: 33. The resulting L-Idh PCR fragment and p416-CCW12p obtained above were digested with BamHI and SalI, and linked to each other, to produce p416-CCW12p-LDH, which is a L-Idh expression vector.

Also, the L-Idh expression vector includes a yeast autoreplication sequence (ARS)/yeast centromeric sequence (CEN) of SEQ ID NO: 29, a CYC1 terminator of SEQ ID NO: 30, and a L-Idh gene of SEQ ID NO: 13 derived from *Pelodiscus sinensis* japonicas. Also, the CCW12 promoter may be substituted with a CYC promoter of SEQ ID NO: 31, a GPD promoter of SEQ ID NO: 32, and an ADH promoter of SEQ ID NO: 33.

FIG. 1 is a view illustrating a p416-CCW12p-LDH vector. As shown in FIG. 1, LDH derived from *Pelodiscus sinensis japonicas* is inserted in the vector.

(2) Preparation of Gene Exchange Vector

Figure 2:
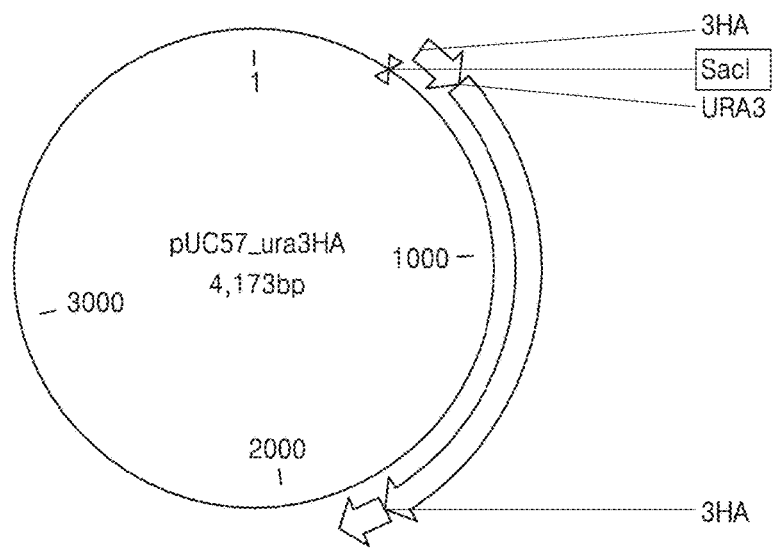
FIG. 2 is a schematic of the pUC57-ura3HA vector.

In order to insert an L-ldh gene at the same time deleting PDC1, CYB2, and GPD1 genes by homologous recombination, a gene exchange vector was prepared as follows. FIG. 2 is a view illustrating a pUC57-ura3HA vector (SEQ ID NO: 34). 3HA is three repeated units of HA (where, "HA" denotes hemagglutinin).

Figure 3:
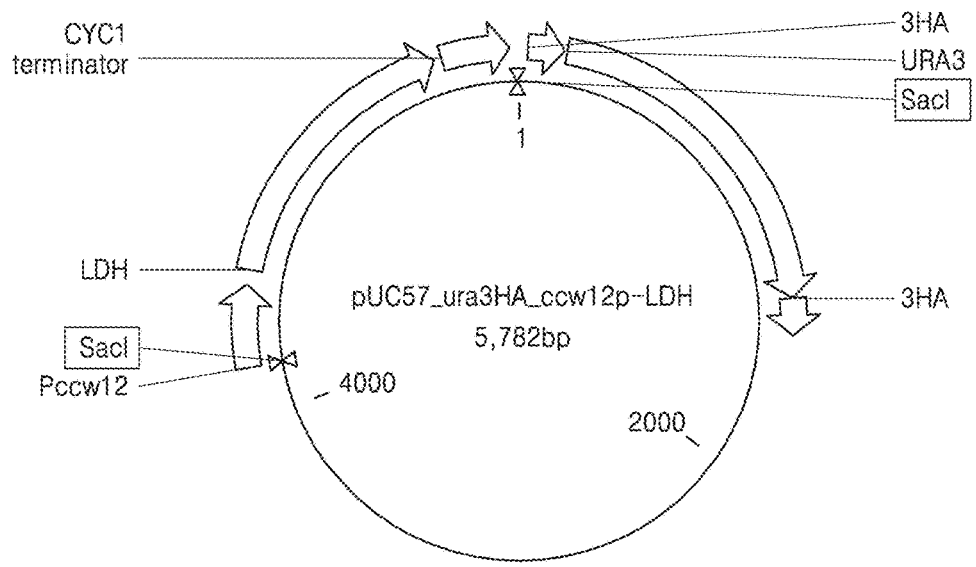
FIG. 3 is a schematic of the pUC57-ura3HA-CCW12p-LDH vector.

PCR was performed by using the p416-CCW12p-LDH thus prepared as a template and primers of SEQ ID NO: 35 and SEQ ID NO: 36, and the PCR fragment thus obtained and the pUC57-ura3HA vector were digested with SacI and linked to each other to prepare a pUC57-ura3HA-CCW12p-LDH vector. FIG. 3 is a view illustrating a pUC57-ura3HA-CCW12p-LDH vector.

In order to prepare a PDC1 gene deletion cassette, PCR was performed by using the pUC57-ura3HA-CCW12p-LDH thus prepared as a template and primers of SEQ ID NO: 37 and SEQ ID NO: 38.

In order to prepare a CYB2 gene deletion cassette, PCR was performed by using the pUC57-ura3HA-CCW12p-LDH thus prepared as a template and primers of SEQ ID NO: 39 and SEQ ID NO: 40.

In order to prepare a GPD1 gene deletion cassette, PCR was performed by using the pUC57-ura3HA-CCW12p-LDH thus prepared as a template and primers of SEQ ID NO: 41 and SEQ ID NO: 42.

(3) Inactivation of Pdc1, Gpd1, and Cyb2 Genes

A mutant strain prepared by deleting pdc1 from *S. cerevisiae* CEN.PK2-1D was obtained as follows. *S. cerevisiae* CEN.PK2-1D was spread on a YPD agar (including 10 g of yeast extract, 20 g/L of peptone, 20 g/L of glucose, and 20 g/L of agar) plate and cultured for about 24 hours at about 30° C., and colonies obtained therefrom were inoculated in about 10 ml of a YPD liquid medium and cultured for about 18 hours at about 30° C. The culture solution was inoculated in about 50 ml of a YPD liquid medium contained in a 250 ml-flask at a concentration of about 1% (v/v) and in an incubator vortexing at a rate of about 230 rpm at about 30° C. After about 4 to 5 hours, when the $OD_{600}$ reached about 0.5, the cells were centrifuged at a rate of about 4,500 rpm for about 10 minutes to harvest cells, and the cells were resuspended in a lithium acetate solution at a concentration of about 100 mM. Then, the suspended cells were centrifuged at a rate of about 4,500 rpm for about 10 minutes to harvest cells, and the harvested cells were re-suspended in a lithium acetate solution at a concentration of about 1 M including about 15% of glycerol. Then, the solution was divided into samples, each with a volume of about 100 ul.

In order to delete a pdc1 gene, the PDC1 deletion cassette prepared in Example 1(2) was mixed with 50% polyethyleneglycol and a single stranded carrier DNA, and reacted in a water bath at 42° C. for about 1 hour. Then, the culture solution was spread on a uracil (ura)-free minimal agar plate (YSD, which stands for yeast synthetic drop-out including 6.7 g/L of yeast nitrogen base without amino acids (Sigma-Aldrich: Cat. no. Y0626), 1.4 g/L of yeast synthetic drop-out without uracil (Sigma-Aldrich: Cat. no. Y1501), 20 g/L of glucose, and 20 g/L of agar), and the cells therein were grown at 30° C. for 24 hours or more. Ten colonies (i.e., mutant strains) grown on the ura-free minimal agar plate were selected, spread onto a fresh YSD (−his) agar plate, and at the same time, inoculated into a YSD (−ura) liquid medium to isolate the genomic DNA from the mutant strains above by using a commonly used kit (Gentra Puregene Cell kit, Qiagen, USA). In order to confirm deletion of the pdc1 gene, a PCR was performed using the isolated genomic DNA of the mutant strain as a template with primers of SEQ ID NO: 43 and SEQ ID NO: 44, and then, electrophoresis was performed on the obtained PCR product to confirm pdc1 deletion. As a result, the obtained strain was *S. cerevisiae* CEN.PK2-1D (Δ pdc1::ldh+ura3).

Also, for additional gene deletion using the gene exchange vector, a selection marker URA3, which was introduced for preparation of the CEN.PK2-1D (Δ pdc1::ldh+ura3) strain, was deleted from the strain as follows. *S. cerevisiae* CEN.PK2-1D (Δ pdc1::ldh+ura3) was inoculated in about 10 ml of a YPD liquid medium (including 10 g/L of yeast extract, 20 g/L of peptone, and 20 g/L of glucose), cultured for about 18 hours at 30° C., spread on a 5-FOA containing YSD agar plate (including 6.7 g/L of yeast nitrogen base without amino acids, 1.4 g/L of yeast synthetic drop-out, 20 g/L of glucose, 1 µg/L of 5-fluoroorotic acid (5-FOA), and 20 g/L of agar), and cultured for about 24 hours at 30° C. Ten colonies (URA3 pop-out strain) grown on the 5-FOA agar plate were selected, spread onto the fresh 5-FOA agar plate, and at the same time, cultured in a YPD liquid medium to isolate genomic DNA from the selected strain by using a commonly used kit (Gentra Puregene Cell kit, Qiagen, USA). In order to confirm deletion of the URA3 gene, a PCR was performed by using the genomic DNA of the isolated URA3 pop-out strain as a template and primers of SEQ ID NO: 43 and SEQ ID NO: 44, and then electrophoresis was performed on the obtained PCR product to confirm URA3 gene deletion. As a result, *S. cerevisiae* CEN.PK2-1D (Δ pdc1::ldh) was obtained.

A mutant strain prepared by deleting cyb2 from *S. cerevisiae* CEN.PK2-1D (Δpdc1::ldh) was obtained as follows. *S. cerevisiae* CEN.PK2-1D (Δpdc1::ldh) was spread on a YPD agar (including 10 g of yeast extract, 20 g/L of peptone, 20 g/L of glucose, and 20 g/L of agar) plate and cultured for about 24 hours at about 30° C., and colonies obtained therefrom were inoculated in about 10 ml of a YPD liquid medium and cultured for about 18 hours at about 30° C. The sufficiently grown culture solution was inoculated in about 50 ml of a YPD liquid medium contained in a 250 ml-flask at a concentration of about 1% (v/v) and in an incubator vortexing at a rate of about 230 rpm at about 30° C. After about 4 to 5 hours, when the $OD_{600}$ reached about 0.5, the cells were centrifuged at a rate of about 4,500 rpm for about 10 minutes to harvest cells, and the cells were resuspended in a lithium acetate solution at a concentration of about 100 mM. Then, the suspended cells were centrifuged at a rate of about 4,500 rpm for about 10 minutes to harvest cells, and the harvested cells were re-suspended in a lithium acetate solution at a concentration of about 1 M including about 15% of glycerol. Then, the solution was divided into samples, each with a volume of about 100 ul.

In order to delete a cyb2 gene, the CYB2 deletion cassette prepared in Example 1(2) was mixed with 50% polyethyleneglycol and a single stranded carrier DNA, and reacted in a water bath at 42° C. for about 1 hour. Then, the culture solution was spread on a uracil (ura)-free minimal agar plate (YSD, which stands for yeast synthetic drop-out including 6.7 g/L of yeast nitrogen base without amino acids, 1.4 g/L of yeast synthetic drop-out without uracil, 20 g/L of glucose, and 20 g/L of agar), and the cells therein were grown at 30° C. for 24 hours or more. Ten colonies (i.e., mutant strains) grown on the ura-free minimal agar plate were selected, spread onto a fresh YSD (−his) agar plate, and at the same time, inoculated into a YSD (−ura) liquid medium to isolate the genomic DNA from the mutant strains above by using a commonly used kit (Gentra Puregene Cell kit, Qiagen, USA). In order to confirm deletion of the cyb2 gene, a PCR was performed using the isolated genomic DNA of the mutant strain as a template with primers of SEQ ID NO: 45 and SEQ ID NO: 46, and then, electrophoresis was performed on the obtained PCR product to confirm cyb2 deletion. As a result, the obtained strain was *S. cerevisiae* CEN.PK2-1D (Δ pdc1::ldh Δ cyb2::ldh+ura3).

Also, for additional gene deletion using the gene exchange vector, a selection marker URA3, which was used in cyb2 deletion, was deleted from the strain by using a URA3 pop-out method as described above. *S. cerevisiae* CEN.PK2-1D (Δpdc1::ldh Δ cyb2::ldh+ura3) was inoculated in about 10 ml of a YPD liquid medium (including 10 g/L of yeast extract, 20 g/L of peptone, and 20 g/L of glucose), cultured for about 18 hours at 30° C., spread on a 5-FOA containing YSD agar plate (including 6.7 g/L of yeast nitrogen base without amino acids, 1.4 g/L of yeast synthetic drop-out, 20 g/L of glucose, 1 μg/L of 5-fluoroorotic acid (5-FOA), and 20 g/L of agar), and cultured for about 24 hours at 30° C. Ten colonies (URA3 pop-out strain) grown on the 5-FOA agar plate were selected, spread onto the fresh 5-FOA agar plate, and at the same time, cultured in a YPD liquid medium to isolate genomic DNA from the selected strain by using a commonly used kit (Gentra Puregene Cell kit, Qiagen, USA). In order to confirm deletion of the URA3 gene, a PCR was performed by using the genomic DNA of the isolated URA3 pop-out strain as a template and primers of SEQ ID NO: 36 and SEQ ID NO: 37, and then electrophoresis was performed on the obtained PCR product to confirm URA3 gene deletion. As a result, *S. cerevisiae* CEN.PK2-1D (Δpdc1::ldh Δcyb2::ldh) was obtained.

A mutant strain prepared by deleting gpd1 from *S. cerevisiae* CEN.PK2-1D (Δ pdc1::ldhΔcyb2::ldh) was obtained as follows. *S. cerevisiae* CEN.PK2-1D (Δpdc1::ldhΔcyb2::ldh) was spread on a YPD agar (including 10 g of yeast extract, 20 g/L of peptone, 20 g/L of glucose, and 20 g/L of agar) plate and cultured for about 24 hours at about 30° C., and colonies obtained therefrom were inoculated in about 10 ml of a YPD liquid medium and cultured for about 18 hours at about 30° C. The sufficiently grown culture solution was inoculated in about 50 ml of a YPD liquid medium contained in a 250 ml-flask at a concentration of about 1% (v/v) and in an incubator vortexing at a rate of about 230 rpm at about 30° C. After about 4 to 5 hours, when the OD$_{600}$ reached about 0.5, the cells were centrifuged at a rate of about 4,500 rpm for about 10 minutes to harvest cells, and the cells were resuspended in a lithium acetate solution at a concentration of about 100 mM. Then, the suspended cells were centrifuged at a rate of about 4,500 rpm for about 10 minutes to harvest cells, and the harvested cells were re-suspended in a lithium acetate solution at a concentration of about 1 M including about 15% of glycerol. Then, the solution was divided into samples, each with a volume of about 100 ul.

In order to delete a gpd1 gene, the gpd1 deletion cassette prepared in Example 1(2) was mixed with 50% polyethyleneglycol, a single stranded carrier DNA, and *S. cerevisiae* CEN.PK2-1D (Δ pdc1::ldhΔcyb2::ldh), and reacted in a water bath at 42° C. for about 1 hour, in the same manner used in deletion of pdc1 and cyb2 genes as described above. Then, the culture solution was spread on a uracil (ura)-free minimal agar plate (YSD, which stands for yeast synthetic drop-out including 6.7 g/L of yeast nitrogen base without amino acids, 1.4 g/L of yeast synthetic drop-out without uracil, 20 g/L of glucose, and 20 g/L of agar), and the cells therein were grown at 30° C. for 24 hours or more. Ten colonies (i.e., mutant strains) grown on the ura-free minimal agar plate were selected, spread onto a fresh YSD (–his) agar plate, and at the same time, inoculated into a YSD (–ura) liquid medium to isolate the genomic DNA from the mutant strains above by using a commonly used kit (Gentra Puregene Cell kit, Qiagen, USA). In order to confirm deletion of the gpd1 gene, a PCR was performed using the isolated genomic DNA of the mutant strain as a template with primers of SEQ ID NO: 47 and SEQ ID NO: 48, and then, electrophoresis was performed on the obtained PCR product to confirm gpd1 deletion. As a result, the obtained strain was *S. cerevisiae* CEN.PK2-1D (Δ pdc1::ldh Δ cyb2::ldh Δ gpd1::ldh+ura3).

Also, for additional gene deletion using the gene exchange vector, a selection marker URA3, which was used in gpd1 deletion, was deleted from the strain by using a URA3 pop-out method as described above. *S. cerevisiae* CEN.PK2-1D (Δ pdc1::ldh Δ cyb2::ldh Δ gpd1::ldh+ura3) was inoculated in about 10 ml of a YPD liquid medium (including 10 g/L of yeast extract, 20 g/L of peptone, and 20 g/L of glucose), cultured for about 18 hours at 30° C., spread on a 5-FOA containing YSD agar plate (including 6.7 g/L of yeast nitrogen base without amino acids, 1.4 g/L of yeast synthetic drop-out, 20 g/L of glucose, 1 μg/L of 5-fluoroorotic acid (5-FOA), and 20 g/L of agar), and cultured for about 24 hours at 30° C. Ten colonies (URA3 pop-out strain) grown on the 5-FOA agar plate were selected, spread onto the fresh 5-FOA agar plate, and at the same time, cultured in a YPD liquid medium to isolate genomic DNA from the selected strain by using a commonly used kit (Gentra Puregene Cell kit, Qiagen, USA). In order to confirm deletion of the URA3 gene, a PCR was performed by using the genomic DNA of the isolated URA3 pop-out strain as a template and primers of SEQ ID NO: 47 and SEQ ID NO: 48, and then electrophoresis was performed on the obtained PCR product to confirm URA3 gene deletion. As a result, *S. cerevisiae* CEN.PK2-1D (Δ pdc1::ldh Δcyb2::ldh Δ gpd1:: ldh) was obtained.

*S. cerevisiae* CEN.PK2-1D (Δ pdc1::ldh Δ cyb2:: ldhΔgpd1::ldh) was deposited with the Korean Collection for Type Cultures (KCTC) on May 30, 2013 under Accession No. KCTC 12415BP.

2. Additional Introduction of LDH gene

In order to additionally modify and/or enhance lactate production pathways to increase lactate production by redox balance, an L-ldh gene may be additionally introduced to a genome of a KCTC12415BP strain, and a method of additionally introducing an L-ldh gene to a genome may be as follows.

Figure 4:
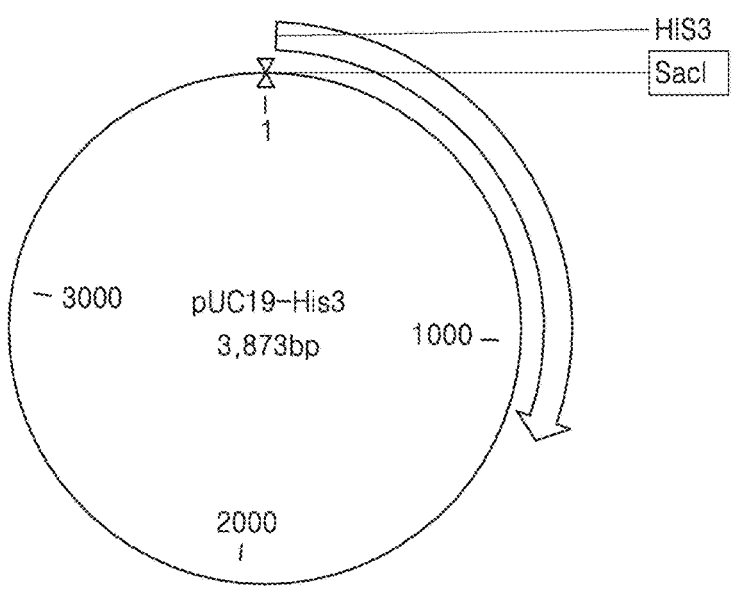
FIG. 4 is a schematic of the pUC19-HIS3 vector.

A gene introduction vector for additional introduction of an L-ldh gene was prepared as follows. FIG. 4 is a view illustrating a pUC19-HIS3 vector (SEQ ID NO: 49). A HIS3 PCR fragment obtained by performing a PCR with a pRS413 (ATCC8758) vector as a template and using primers of SEQ ID NO: 50 and SEQ ID NO: 51 was digested with SalI, and the resultant was inserted into a pUC19 vector (NEB, N3041) digested with SalI, thereby producing a pUC19-HIS3 vector that may be used as a selection marker for a HIS3 gene.

Figure 5:
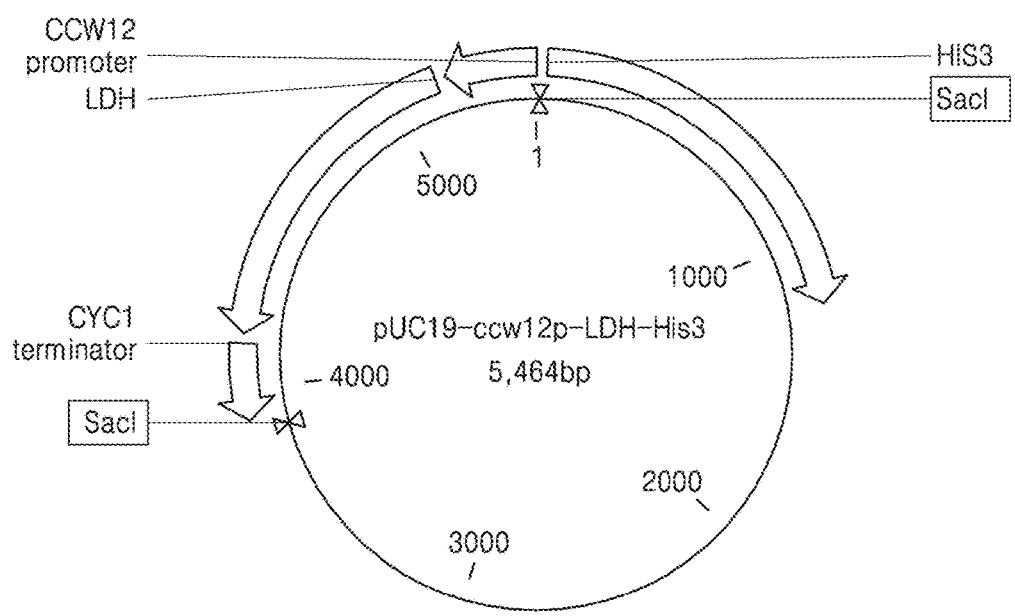
FIG. 5 is a schematic of the pUC19-CCW12p-LDH-HIS3 vector.

A pUC19-CCW12p-LDH-HIS3 was prepared as follows: a PCR was performed using the p416-CCW12p-LDH of section 1 of Example 1 as a template with primers of SEQ ID NO: 35 and SEQ ID NO: 36. The resulting PCR fragment and the prepared pUC19-HIS3 vector were digested with SacI and ligated, thereby producing pUC19-CCW12p-LDH-HIS3. FIG. 5 is a view illustrating a pUC19-CCW12p-LDH-HIS3 vector.

Also, in order to additionally introduce L-Idh into the genome of KCTC12415BP strain, a PCR was performed by using the pUC19-CCW12p-LDH-HIS3 thus prepared as a template and primers of SEQ ID NO: 52 and SEQ ID NO: 53 to prepare a L-Idh expression cassette for inserting the L-Idh into a location of a TRP1 (phosphoribosyl-anthranilate isomerase) gene.

The cassette including L-Idh may be inserted into a genetic locus of TRP1, and in this case, the L-Idh may be inserted as a TRP1 gene is deleted. The L-Idh insertion mutant strain was prepared as follows.

The prepared KCTC12415BP strain was spread on a YPD agar (including 10 g of yeast extract, 20 g/L of peptone, 20 g/L of glucose, and 20 g/L of agar) plate and cultured for about 24 hours at about 30° C., and colonies obtained therefrom were inoculated in about 10 ml of a YPD liquid medium and cultured for about 18 hours at about 30° C. The sufficiently grown culture solution was inoculated in about 50 ml of a YPD liquid medium contained in a 250 ml-flask at a concentration of about 1% (v/v) and in an incubator vortexing at a rate of about 230 rpm at about 30° C.

After about 4 to 5 hours, when the $OD_{600}$ reached about 0.5, the cells were centrifuged at a rate of about 4,500 rpm for about 10 minutes to harvest cells, and the cells were resuspended in a lithium acetate solution at a concentration of about 100 mM. Then, the suspended cells were centrifuged at a rate of about 4,500 rpm for about 10 minutes to harvest cells, and the harvested cells were re-suspended in a lithium acetate solution at a concentration of about 1 M including about 15% of glycerol. Then, the solution was divided into samples, each with a volume of about 100 ul.

In order to delete a TRP1 gene and express L-Idh at the same time, a L-Idh expression cassette including the HIS3 gene prepared above was mixed with 50% of polyethylene glycol and a single stranded carrier DNA, and reacted in a water bath at 42° C. for 1 hour. Then, the culture solution was spread on a histidine (his)-free minimal agar plate (including 6.7 g/L of yeast nitrogen base without amino acids, 1.4 g/L of yeast synthetic drop-out without histidine (Sigma-Aldrich: Cat. no. Y1751), 20 g/L glucose, and 20 g/L of agar) and grown at 30° C. for 24 hours or more. Ten colonies (i.e., mutant strains) grown on the his-free minimal agar plate were selected, spread onto a fresh YSD (–his) agar plate, and at the same time, inoculated into a YSD (–his) liquid medium to isolate the genomic DNA from the mutant strains above by using a commonly used kit (Gentra Puregene Cell kit, Qiagen, USA). In order to confirm deletion of the TRP1 gene, a PCR was performed using the isolated genomic DNA of the mutant strain as a template with primers of SEQ ID NOs: 54 and 55, and then, electrophoresis was performed on the obtained PCR product to confirm insertion of the L-Idh expression cassette. As a result, the obtained strain was referred to as CEN.PK2-1D KCTC12415BP Δ trp1::Idh.

3. Preparation of *S. cerevisiae* Strain from which nde1 is Deleted (3.1) Preparation of nde1 gene Deletion Cassette In order to delete a nde1 gene by homologous recombination, a vector for inactivating the nde1 gene pUC57-ura3HA was prepared in Example 1.1.2. In order to prepare a nde1 gene deletion cassette, a PCR was performed using the prepared pUC57-ura3HA as a template and primers of SEQ ID NO: 56 and SEQ ID NO: 57.

(3.2) Preparation of *S. cerevisiae* from which nde1 is Deleted

A mutant strain of the Δtrp1::Idh strain (KCTC12415BPΔtrp1::Idh), in which nde1 is deleted, was prepared in the same manner as follows. The *S. cerevisiae* CEN.PK2-1D (KCTC12415BP Δ trp1::Idh) was spread onto a YPD agar plate (including 10 g of yeast extract, 20 g of peptone, 20 g of glucose, and 20 g/L of agar) and incubated for 24 hours at 30° C., and then, colonies obtained therefrom were inoculated in about 10 ml of a YPD liquid medium and cultured for 18 hours at 30° C. The sufficiently grown culture solution was inoculated in about 50 ml of a YPD liquid medium contained in a 250 ml-flask at a concentration of 1% (v/v) and in an incubator vortexing at a rate of about 230 rpm and at 30° C. After about 4 to 5 hours, when the $OD_{600}$ reached about 0.5, the culture was centrifuged at a rate of about 4,500 rpm for about 10 minutes to harvest cells, and the cells were resuspended in a lithium acetate solution at a concentration of about 100 mM. Then, the suspended cells were centrifuged at a rate of about 4,500 rpm for about 10 minutes to harvest cells, and the harvested cells were re-suspended in a lithium acetate solution at a concentration of about 1 M including about 15% of glycerol. Then, the solution was divided into samples, each with a volume of about 100 ul.

In order to delete an nde1 gene, the nde 1 deletion cassette was mixed with 50% of polyethylene glycol and single stranded carrier DNA, 100 μl of the re-suspension solution containing the water-soluble competent cells was added thereto, and reacted in a water bath for about 1 hour at 42° C., in the same manner used in deletion of pdc1, cyb2, and gpd1 genes as described above. Then, the culture solution was spread on a uracil-free minimal agar plate (including 6.7 g/L of yeast nitrogen base without amino acids, 1.4 g/L of yeast synthetic drop-out without uracil, 20 g/L glucose, and 20 g/L of agar) and grown for about 24 hours or more at 30° C. Ten colonies grown on the plate were selected, spread onto the fresh uracil-free minimal agar plate, and at the same time, inoculated into a liquid medium including the same components contained in the uracil-free minimal agar plate to isolate the genomic DNA from the above mutant strains by using a commonly used kit (Gentra Puregene Cell kit, Qiagen, USA). In order to confirm deletion of the nde 1 gene, a PCR was performed using the isolated genomic DNA of the mutant strain as a template with primers of SEQ ID NO: 58 and SEQ ID NO: 59, and then, electrophoresis was performed on the obtained PCR product to confirm nde1 deletion. As a result, the obtained strain was *S. cerevisiae* CEN.PK2-1D (KCTC12415BP Δ trp1::Idh Δ nde1+ura3).

Also, for additional gene deletion using the gene deletion vector, a selection marker URA3 gene, which was used for the deletion of the nde1 gene, was removed by using a URA3 pop-out method. That is, *S. cerevisiae* CEN.PK2-1D (KCTC12415BP Δ trp1::Idh Δ nde1+ura3) was inoculated in about 10 ml of a YPD liquid medium, cultured for about 18 hours at 30° C., spread on a 5-FOA agar plate (YSD, including 6.7 g/L of yeast nitrogen base without amino acids, 1.4 g/L of yeast synthetic drop-out, 20 g/L glucose, 1 ug/L of 5-fluoroorotic acid, and 20 g/L agar), and cultured for about 24 hours at 30° C. Ten colonies (URA3 pop-out strains) grown on the 5-FOA agar plate were selected, spread onto the fresh 5-FOA agar plate, and at the same time, cultured in a YPD liquid medium to isolate genomic DNA from the selected strain by using a commonly used kit (Gentra Puregene Cell kit, Qiagen, USA). In order to confirm deletion of the URA3 gene, a PCR was performed by using the genomic DNA of the isolated URA3 pop-out strain as a template and primers of SEQ ID NO: 58 and SEQ ID NO: 59, and then electrophoresis was performed on the obtained PCR product to confirm URA3 gene deletion. As a result, *S. cerevisiae* CEN.PK2-1D (KCTC12415BP Δ trp1:: Idh Δ nde1) was obtained.

4. Preparation of *S. cerevisiae* Strain from which nde2 is Deleted (4.1) Preparation of nde2 gene Deletion Cassette In order to delete a nde2 gene by homologous recombination, a vector for inactivating the nde2 gene pUC57-ura3HA was prepared in Example 1.1.2. In order to prepare a nde2 gene deletion cassette, a PCR was performed using the prepared pUC57-ura3HA as a template and primers of SEQ ID NO: 60 and SEQ ID NO: 61.

(4.2) Preparation of *S. cerevisiae* from which nde1 and nde2 are Deleted

The *S. cerevisiae* CEN.PK2-1D (KCTC12415BP Δ trp1:: Idh Δ nde1) was spread onto a YPD agar plate (including 10 g of yeast extract, 20 g of peptone, 20 g of glucose, and 20 g/L of agar) and incubated for 24 hours at 30° C., and then, colonies obtained therefrom were inoculated in about 10 ml of a YPD liquid medium and cultured for 18 hours at 30° C. The sufficiently grown culture solution was inoculated in about 50 ml of a YPD liquid medium contained in a 250 ml-flask at a concentration of 1% (v/v) and in an incubator vortexing at a rate of about 230 rpm and at 30° C. After about 4 to 5 hours, when the $OD_{600}$ reached about 0.5, the culture was centrifuged at a rate of about 4,500 rpm for about 10 minutes to harvest cells, and the cells were resuspended in a lithium acetate solution at a concentration of about 100 mM. Then, the suspended cells were centrifuged at a rate of about 4,500 rpm for about 10 minutes to harvest cells, and the harvested cells were re-suspended in a lithium acetate solution at a concentration of about 1 M including about 15% of glycerol. Then, the solution was divided into samples, each with a volume of about 100 ul.

In order to delete an nde2 gene, the nde 2 deletion cassette prepared in above section 4.1 was mixed with 50% of polyethylene glycol and single stranded carrier DNA, 100 μl of the re-suspension solution containing the water-soluble competent cells was added thereto, and reacted in a water bath for about 1 hour at 42° C., in the same manner used in deletion of pdc1, cyb2, gpd1, and nde1 genes as described above. Then, the culture solution was spread on a uracil-free minimal agar plate (including 6.7 g/L of yeast nitrogen base without amino acids, 1.4 g/L of yeast synthetic drop-out without uracil, 20 g/L glucose, and 20 g/L of agar) and grown for about 24 hours or more at 30° C. Ten colonies grown on the plate were selected, spread onto the fresh uracil-free minimal agar plate, and at the same time, inoculated into a liquid medium including the same components contained in the uracil-free minimal agar plate to isolate the genomic DNA from the above mutant strains by using a commonly used kit (Gentra Puregene Cell kit, Qiagen, USA). In order to confirm deletion of the nde 2 gene, a PCR was performed using the isolated genomic DNA of the mutant strain as a template with primers of SEQ ID NO: 60 and SEQ ID NO: 61, and then, electrophoresis was performed on the obtained PCR product to confirm nde2 deletion. As a result, the obtained strain was *S. cerevisiae* CEN.PK2-1D (KCTC12415BP Δ trp1::Idh Δ nde1Δnde2+ ura3).

Also, for additional gene deletion using the gene deletion vector, a selection marker URA3 gene, which was used for the deletion of the nde2 gene, was removed by using a URA3 pop-out method. That is, *S. cerevisiae* CEN.PK2-1D (KCTC12415BP Δ trp1:P:Idh Δ nde1Δnde2+ura3) was inoculated in about 10 ml of a YPD liquid medium, cultured for about 18 hours at 30° C., spread on a 5-FOA agar plate (YSD, containing 6.7 g/L of yeast nitrogen base without amino acids, 1.4 g/L of yeast synthetic drop-out, 20 g/L glucose, 1 ug/L of 5-fluoroorotic acid, and 20 g/L of agar), and cultured for about 24 hours at 30° C. Ten colonies (URA3 pop-out strains) grown on the 5-FOA agar plate were selected, spread onto the fresh 5-FOA agar plate, and at the same time, cultured in a YPD liquid medium to isolate genomic DNA from the selected strain by using a commonly used kit (Gentra Puregene Cell kit, Qiagen, USA). In order to confirm deletion of the URA3 gene, a PCR was performed by using the genomic DNA of the isolated URA3 pop-out strain as a template and primers of SEQ ID NO: 60 and SEQ ID NO: 61, and then electrophoresis was performed on the obtained PCR product to confirm URA3 gene deletion. As a result, *S. cerevisiae* CEN.PK2-1D (KCTC12415BP Δ trp1:: Idh Δ nde1Δnde2) was obtained. Hereinafter, the strain is referred to as "SAIT1".

EXAMPLE 2

Preparation of *S. cerevisiae* from which DGA1 and/or LRO1 are Deleted

1. Preparation of DGA1 and/or LRO1 gene Deletion Cassette

In order to delete a DGA1 gene and a LRO1 gene by homologous recombination, a vector for inactivating the DGA1 gene and the LRO1 gene pUC57-ura3HA was prepared in Example 1.1.2. In order to prepare a DGA1 and/or LRO1 gene deletion cassette, a PCR was performed using the prepared pUC57-ura3HA as a template and primers of SEQ ID NO: 37 and SEQ ID NO: 38, and primers of SEQ ID NO: 39 and SEQ ID NO: 40, respectively.

2. Preparation of *S. cerevisiae* Strain from which DGA1 and LRO1 genes are Deleted SAIT1 ΔDGA1 strain was prepared in the same manner as used in Example 1.4.(4.2), except that SAIT1 strain was used as a starting strain, and primers of SEQ ID NO: 62 and SEQ ID NO: 63 were used to confirm DGA1 deletion.

Also, SAIT1 ΔDGA1ΔLRO1 strain, that is, SIAT2 strain was prepared in the same manner as used in Example 14.(4.2), except that SAIT1ΔDGA1 strain was used as a starting strain and primers of SEQ ID NO: 64 and SEQ ID NO: 65 were used to confirm LRO1 deletion.

EXAMPLE 3

Preparation of SAIT1 Strain to which AUR1 and/or OLE1 Genes are Introduced

An AUR1 gene and an OLE1 gene were introduced to a SAIT1 strain.

1. Preparation of Vector for Introducing AUR1 and/or OLE1 Genes

A vector for introducing an AUR1 gene and an OLE1 gene was prepared as follows.

In particular, p416-TEFp-AUR1 and p416-TEFp-OLE1, which are, each respectively, AUR1 and OLE1 expression vectors were respectively prepared, in the same manner as used in Example 1.1.(1), except that primers of SEQ ID NOS: 66 and 67 were used instead of primers of SEQ ID NOS: 25 and 26 as used Example 1.1.(1) to amplify a TEF promoter, ultimately prepared a p416-TEF vector, and primers of SEQ ID NOS: 68 and 68, and SEQ ID NOS 70 and 71 are used to amplify the AUR1 gene of *S. cerevisiae* and the OLE1 gene of *Pichia kudriavzevii* M12, respectively.

2. Preparation of *S. cerevisiae* Strain to which AUR1 Gene and OLE1 Gene are Introduced A SAIT1 strain was used as a starting strain, and a PCR was performed by using a p416-TEFp-AUR1 vector for introducing an AUR1 gene as prepared in above section 1 after performing double digestion with XbaI and XhoI, and primers of SEQ ID NO: 72 and SEQ ID NO: 73. The fragment thus obtained was introduced by homologous recombination with a genome of the SAIT1 strain by performing the process described in Example 1.1.(3), and the introduction of the AUR1 gene was confirmed by performing a PCR using primers of SEQ ID NO: 74 and SEQ ID NO: 75, thereby preparing a SAIT1(+AUR1) strain (hereinafter, also referred to as "SAIT3"), which is an AUR1 overexpression strain.

A SAIT1 strain was usd as a starting strain, and a PCR was performed by using a p416-TEFp-AUR1 vector for introducing an OLE1 gene as prepared in Example 1 after performing double digestion with XbaI and XhoI, and primers of SEQ ID NO: 76 and SEQ ID NO: 77. The fragment thus obtained was introduced by homologous recombination with a genome of the SAIT1 strain by performing the process described in Example 1.1.(3), and the introduction of the OLE1 gene was confirmed by performing a PCR using primers of SEQ ID NO: 78 and SEQ ID NO: 79, thereby preparing a SAIT1(+OLE1) strain (hereinafter, also referred to as "SAIT4"). Here, the OLE1 gene was derived from *Pichia kudriavzevii* M12. An amino acid sequence of the OLE1 of *Pichia kudriavzevii* M12 has a sequence of SEQ ID NO: 5 and a nucleotide sequence encoding the amino acid sequence has a sequence of SEQ ID NO: 6.

EXAMPLE 4

Confirmation of Acid-tolerance and Capability of Producing Lactate of SAIT1, SAIT1 ΔDGA1, SAIT2, SAIT3, and SAIT4

The SAIT1, SAIT1 ΔDGA1, SAIT2, SAIT3, and SAIT4 strains prepared in Examples 1 to 3 were each spread on a YPD agar plate and cultured at 30° C. for 24 hours or more, and then a colony obtained therefrom was inoculated in 100 ml of a YPD liquid medium including 80 g/L of glucose and cultured at 30° C. for 16 hours under aerobic conditions. Here, fermentation was performed on 100 ml of the strain culture solution that was separately inoculated in a bioreactor containing 1 L of a synthetic medium (including 60 g/L of glucose, 20 g/L of a yeast extract, 50 g/L of $K_2HPO_4$, 10 g/L of $MgSO_4$, 0.1 g/L of tryptophane, and 0.1 g/L of histidine) and cultured.

The fermentation or culture was performed with initial concentrations of 60 g/L of glucose and 20 g/L of a yeast extract at 30° C. During the culture, pH was maintained at about pH 5 for up to 16 hours, at about pH 4.5 for up to 24 hours, and at about pH 3.0 for up to 60 hours by using 5N $Ca(OH)_2$, and a concentration of the glucose was maintained at 20 g/L. Additional synthetic medium compositions include 50 g/L of $K_2HPO_4$, 10 g/L of $MgSO_4$, 0.1 g/L of tryptophan, and 0.1 g/L of histidine in addition to the glucose. Here, 2%, 3%, 4%, and 5% of lactate based on the total volume of the medium were added to the medium at an initial stage to confirm tolerant property of the strains with respect to acid.

A cell concentration in the culture solution was measured by using a spectrophotometer. During the culture, samples were periodically obtained from a bioreactor, and the obtained samples were centrifuged at a rate of 13,000 rpm for 10 minutes. Then, concentrations of metabolites of the supernatant, lactate, and glucose were analyzed by using HPLC. Also, various lipid molecules in the supernatant were analyzed by using an ultra-performance liquid chromatography quadrupole time of flight mass spectrometer (UPLC-qTOF-MS/MS).

Figure 6:
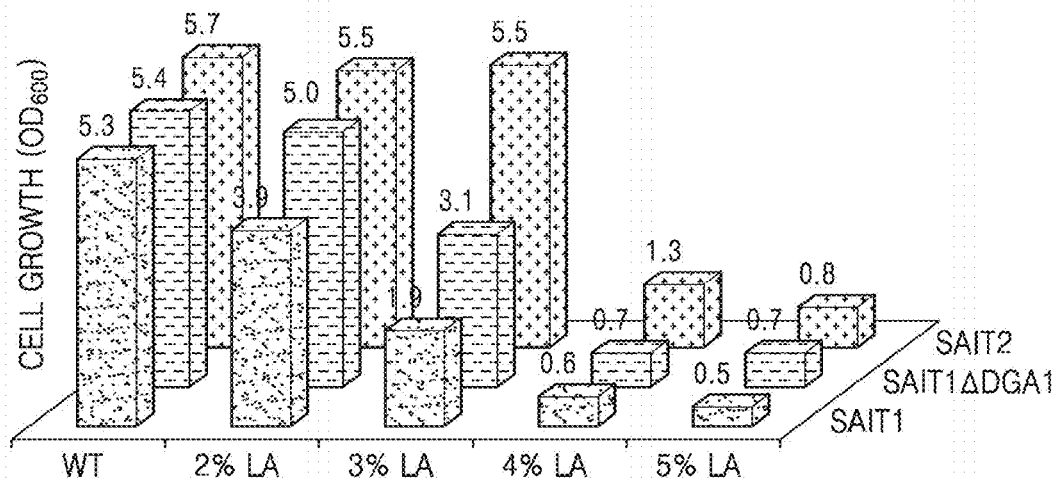
FIG. 6 is a graph of experimental data illustrating the effect of deletion of DGA1 and LRO1 genes in S. cerevisiae on cell growth under acidic conditions.

As shown in FIG. 6, cell growth in SAIT1 ΔDGA1 and SAIT2 was higher than that of SAIT1, particularly, under acidic conditions. The horizontal axis shows concentrations of lactate included in a medium used for the culture. Also, WT refers to "wild-type strain", that is, SAIT1, and lactate was not included, that is a concentration of lactate added was 0. The vertical axis denotes an $OD_{600}$ value.

Figure 7:
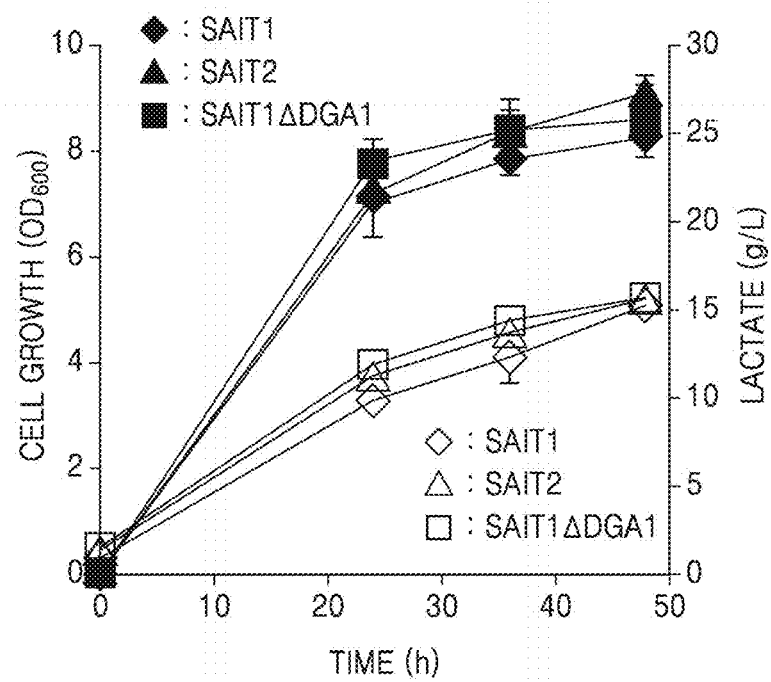
FIG. 7 is a graph of experimental data illustrating the effect of deletion of DGA1 and LRO1 genes in S. cerevisiae on cell growth and lactate production under acidic conditions.

As shown in FIG. 7, lactate production (filled out markers), as well as cell growth (empty markers), in SAIT1ΔDGA1 and SAIT2 increased than that of SAIT1. In particular, lactate production of SAIT1 was 24.6 g/L, SAIT1ΔDGA1 was 25.9 g/L, and SAIT2 was 27.25 g/L at the culturing time of 50 hours, and thus lactate produced from SAIT2 was 10.8% higher than that of SAIT1. At the culturing time of 50 hours, regarding cell growth, SAIT1 was 5.05, SAIT1ΔDGA1 was 5.2, and SAIT2 was 5.205. The horizontal axis shows a period of culturing time, and a vertical axis denotes an $OD_{600}$ value and lactate concentration (g/L). The lactate concentration indicates a concentration of a supernatant, not cells.

Figure 8:
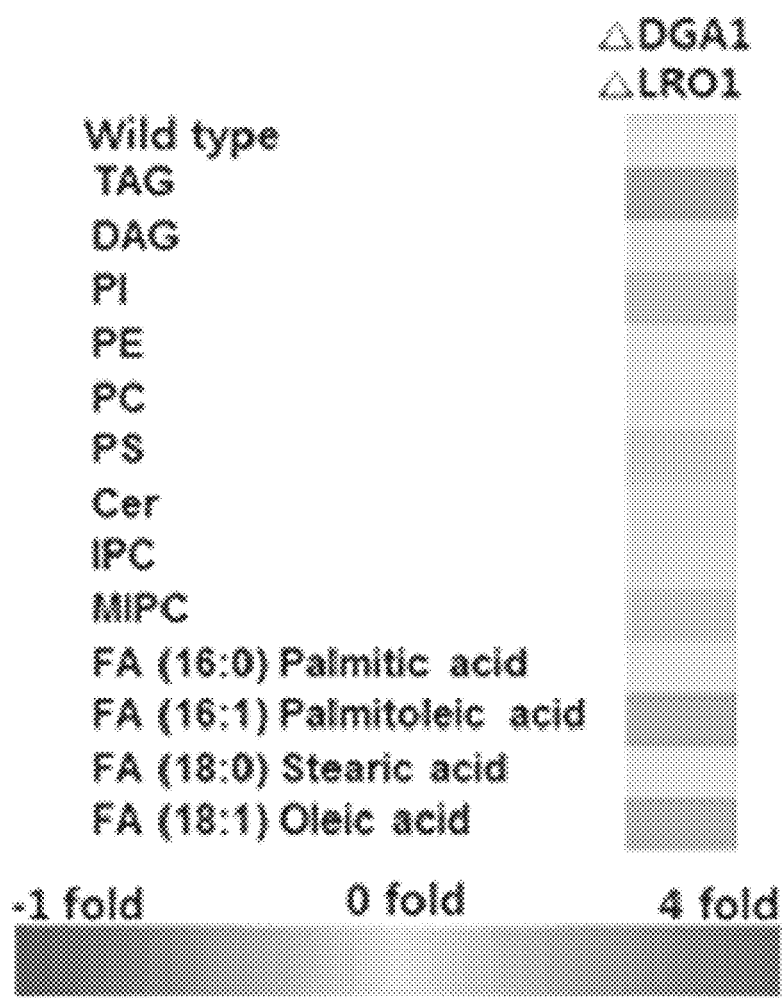
FIG. 8 depicts experimental data illustrating the effect of deletion of DGA1 and LRO1 genes in S. cerevisiae on an amount of lipid components in cells grown under acidic conditions.

As shown in FIG. 8, compared to SAIT1, TAG decreased about 37.9% in SAIT2 (see an arrow). The bar at a lower part represents a concentration of a compound by an intensity of color, wherein, WT, that is, when the result of SAIT1 was 0 fold, 4 fold indicates an increase of 4 times, and −1 fold indicates a decrease of 1 time. PI denotes phosphatidyl inositol, PE denotes phosphatidyl ethanol, PC denotes phosphatidyl choline, PS denotes phosphatidyl serine, cer denotes ceramide, IPC denotes inositol phosphorylceramide, MIPC denotes mannosyl-inositol phosphorylceramide, and FA denotes fatty acid.

Figure 9:
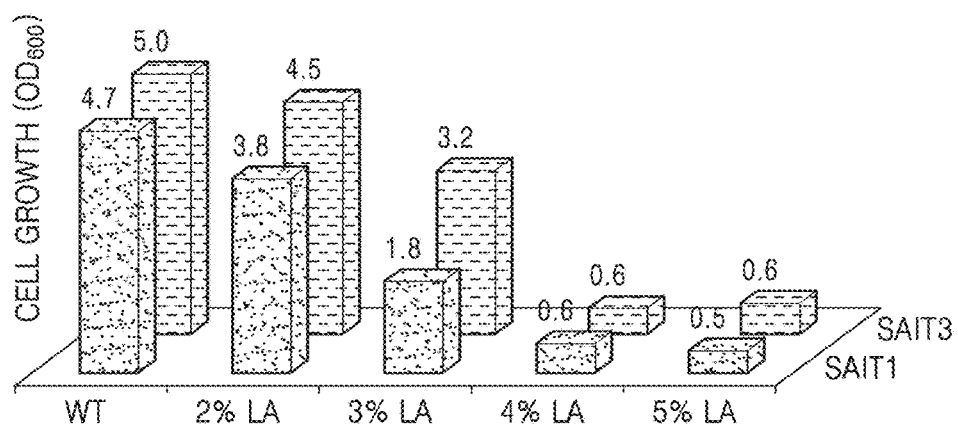
FIG. 9 is a graph of experimental data illustrating the effect of overexpression of AUR1 gene in S. cerevisiae on cell growth under acidic conditions.

As shown in FIG. 9, cell growth in SAIT3 was higher than that of SAIT1, particularly, under acidic condition. In particular, with respect to cell growth at 3% LA, SAIT3 was about 1.8 times higher than that of SAIT1. The vertical axis shows lactate concentrations included in a medium used in the culture. Also, WT refers to "wild-type strain", that is, a strain modified in the same manner as used in treating other strains, except that SAIT1 was used, and lactate was not included, that is a concentration of lactate added was 0. The horizontal axis denotes an $OD_{600}$ value.

Figure 10:
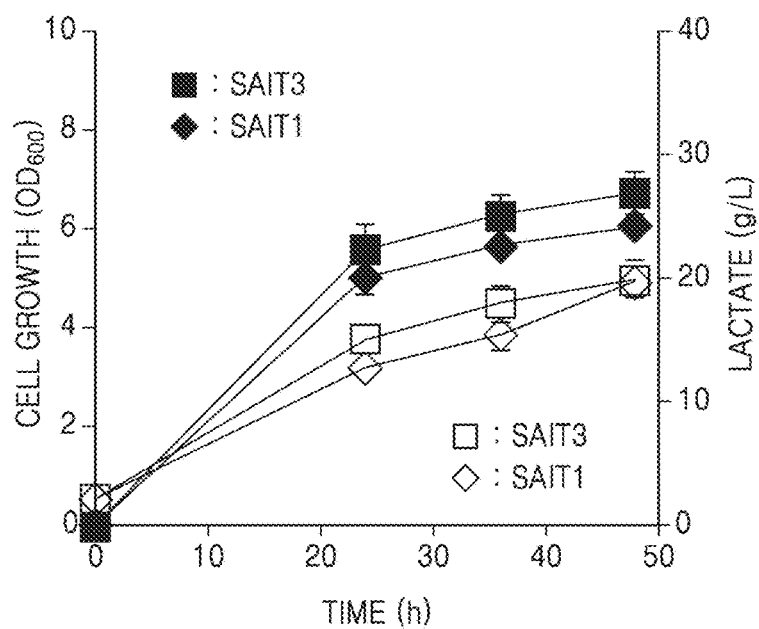
FIG. 10 is a graph of experimental data illustrating the effect of overexpression of AUR1 gene in S. cerevisiae on cell growth and lactate production under acidic conditions.

As shown in FIG. 10, cell growth (empty markers) in SAIT3 increased compared to cell growth of SAIT1, and lactate production (filled out markers) increased about 11% in SAIT3. The horizontal axis shows a period of culturing time, and a vertical axis denotes an $OD_{600}$ value and lactate concentration (g/L). The lactate concentration indicates a concentration of a supernatant, not cells.

Figure 11:
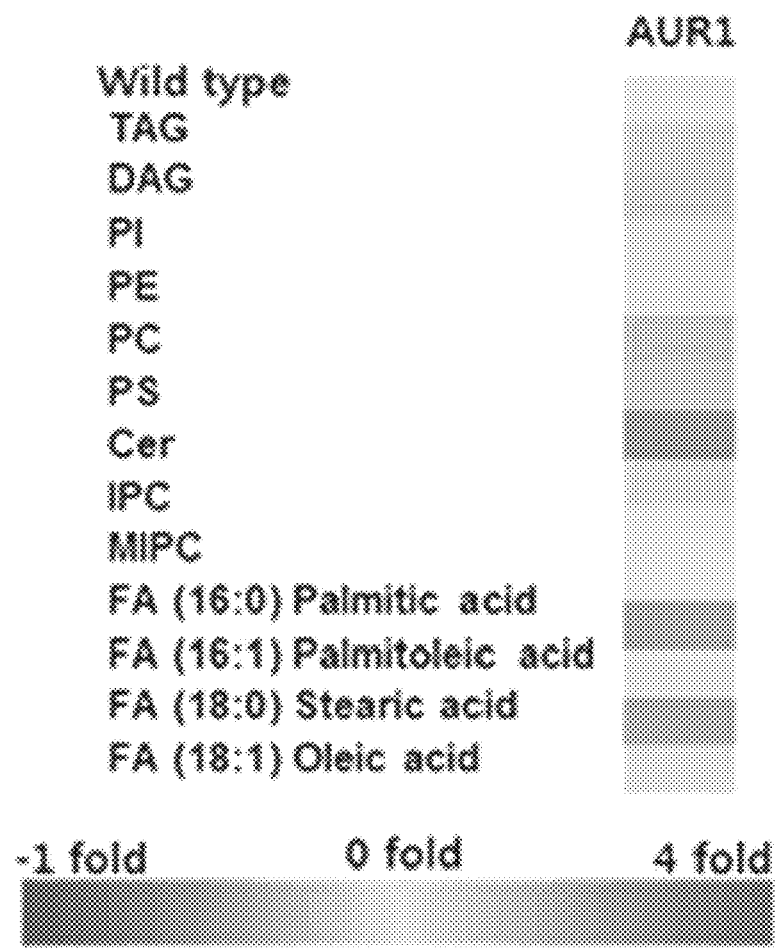
FIG. 11 depicts experimental data illustrating the effect of overexpression of AUR1 gene in S. cerevisiae on an amount of lipid components in cells grown under acidic conditions.

As shown in FIG. 11, IPC in SAIT3 increased about 38.6% compared to that of SAIT1. The bar at a lower part and abbreviations are the same as defined in connection with FIG. 8.

Figure 12:
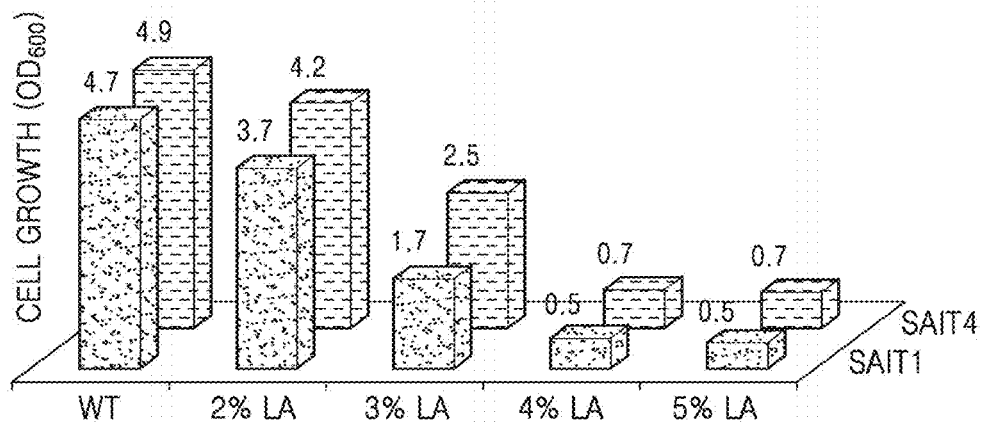
FIG. 12 is a graph of experimental data illustrating the effect of overexpression of OLE1 gene in S. cerevisiae on cell growth under acidic conditions.

As shown in FIG. 12, cell growth in SAIT4 was higher than that of SAIT1, particularly, under acidic condition. The horizontal axis shows lactate concentrations included in a medium used in the culture. Also, WT refers to "wild-type strain", that is, a strain modified in the same manner as used in treating other strains, except that SAIT1 was used, and lactate was not included, that is a concentration of lactate added was 0. A vertical axis denotes an $OD_{600}$ value.

Figure 13:
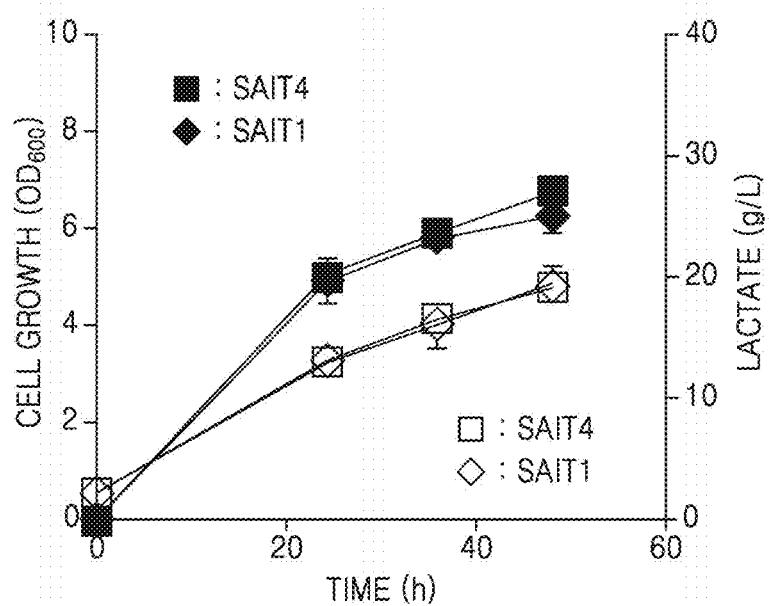
FIG. 13 is a graph of experimental data illustrating the effect of overexpression of OLE1 gene in S. cerevisiae on cell growth and lactate production under acidic conditions.

As shown in FIG. 13, cell growth (empty markers) in SAIT4 increased compared to cell growth of SAIT1, and lactate production (filled out markers) increased about 10% in SAIT4. The horizontal axis shows a period of culturing time, and a vertical axis denotes an $OD_{600}$ value and lactate concentration (g/L). The lactate concentration indicates a concentration of a supernatant, not cells.

Figure 14:
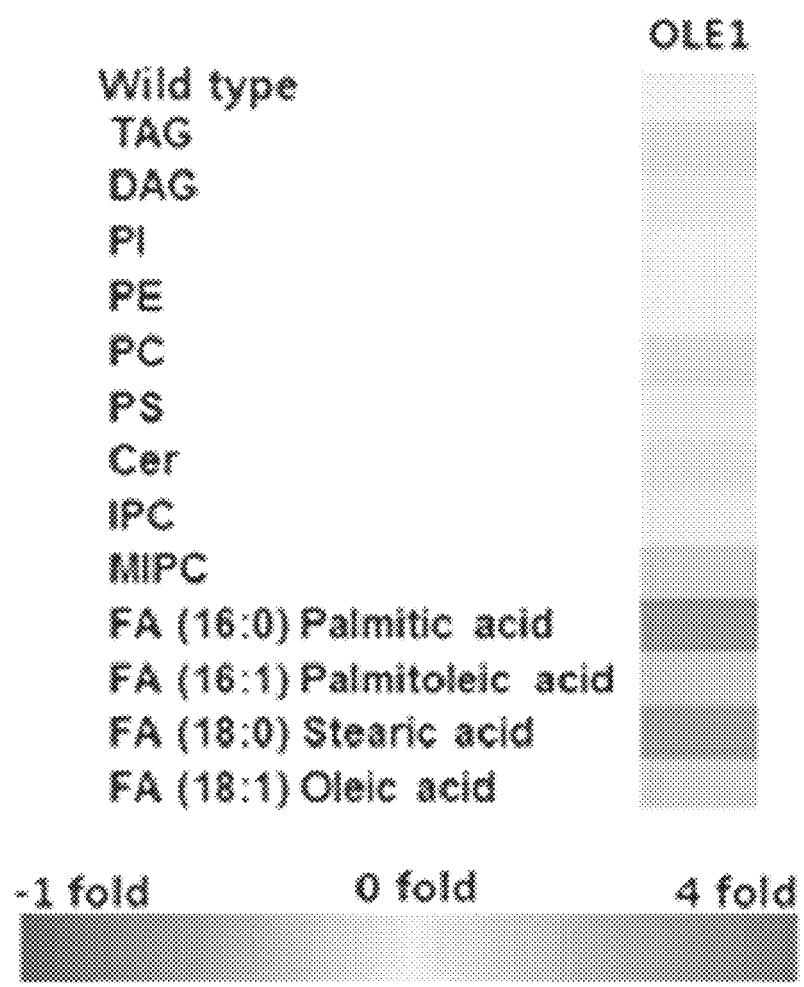
FIG. 14 depicts experimental data illustrating the effect of overexpression of OLE1 gene in S. cerevisiae on an amount of lipid components in cells grown under acidic conditions.

As shown in FIG. 14, compared to SAIT1, amounts of unsaturated fatty acids palmitoleic acid(16:1) and oleic acid(18:1) in SAIT4 increased about 90% and 78%, respectively, whereas, amounts of palmitoleic acid(16:0) and oleic acid(18:0) decreased.

[Accession Number]
Research Center Name: Korean Collection for Type Cultures (KCTC)
Accession Number: KCTC12415BP
Accession Date: 20130530

As described above, according to one or more of the above embodiments, an acid-tolerant yeast cell may culture a yeast cell under acidic condition. When a method of producing an organic acid according to one or more of the above embodiments is used, an organic acid may be efficiently produced even under acidic condition. Also, when a method of producing an acid-tolerant yeast cell according to one or more of the above embodiments is used, an acid-tolerant yeast cell may be efficiently produced.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An acid-tolerant genetically engineered yeast cell comprising
   an exogenous polynucleotide that encodes lactate dehydrogenase; and
   a genetic modification that increases activity of an IPC synthase catalytic subunit AUR1 having at least 95% sequence identity to SEQ ID NO: 1; and optionally further comprising any one of:
   a genetic modification that increases activity of an enzyme that catalyzes introduction of a double bond to a fatty acyl site of a fatty acyl-CoA;
   a genetic modification that decreases activity of an enzyme that catalyzes formation of triacylglycerol (TG) from diacylglycerol (DG); or
   a combination of the genetic modifications.

2. The yeast cell of claim 1, wherein the enzyme that catalyzes introduction of a double bond to a fatty acyl site of a fatty acyl-CoA is an enzyme that belongs to enzyme code (EC) 1.14.19.1; and the enzyme that catalyzes formation of TG from DG is selected from the group consisting of enzymes that belong to EC 2.3.1.22 and 2.3.1.158.

3. The yeast cell of claim 2, wherein the enzyme that catalyzes introduction of a double bond to a fatty acyl site of a fatty acyl-CoA is OLE1; and the enzyme that catalyzes formation of triacylglycerol (TG) from diacylglycerol (DG) is DGA1 or LRO1.

4. The yeast cell of claim 3, wherein OLE1 is a polypeptide each having at least 95% of sequence identity with amino acid sequence of SEQ ID NO:3 or SEQ ID NO:5, DGA1 is a polypeptide having at least 95% of sequence identity with amino acid sequence of SEQ ID NO:7, and LRO1 is a polypeptide having at least 95% of sequence identity with amino acid sequence of SEQ ID NO: 9.

5. The yeast cell of claim 1, wherein the yeast cell comprises a genetic modification increasing expression of AUR1, increasing expression of a gene that encodes an enzyme that catalyzes introduction of a double bond to a fatty acyl site of a fatty acyl-CoA, or increasing expression of both of the genes; and/or a genetic modification removing or disrupting a gene that encodes an enzyme that catalyzes formation of triacylglycerol (TG) from diacylglycerol (DG).

6. The yeast cell of claim 5, wherein the yeast cell comprises a genetic modification increasing the number of copies of a gene that encodes an AUR1 polypeptide having at least 95% of sequence identity with an amino acid sequence of SEQ ID NO: 1, increasing the number of copies of a gene that encodes a polypeptide having at least 95% of sequence identity with amino acid sequence of SEQ ID NO:3 or SEQ ID NO:5, or increasing the number of copies of both genes; and/or a genetic modification removing or disrupting a gene that encodes a polypeptide having at least 95% of sequence identity with an amino acid sequence of SEQ ID NO: 7.

7. The yeast cell of claim 1, wherein the yeast cell is genus *Saccharomyces*, genus *Kluyveromyces*, genus *Candida*, genus *Pichia*, genus *Issatchenkia*, genus *Debaryomyces*, genus *Zygosaccharomyces*, genus *Schizosaccharomyces*, or genus *Saccharomycopsis*.

8. The yeast cell of claim 1, wherein the yeast cell is *Saccharomyces cerevisiae*.

9. The yeast cell of claim 1, wherein the acid-tolerance is tolerance with respect to a C1-C20 organic acid.

10. The yeast cell of claim 1 comprising a recombinantly expressed enzyme that catalyzes formation of a C1-C20 organic acid.

11. The yeast cell of claim 1, wherein the exogenous polynucleotide that encodes lactate dehydrogenase comprises a polynucleotide sequence that encodes an amino acid sequence having at least 95% of sequence identity with an amino acid sequence of SEQ ID NO: 11, or a polynucleotide sequence of SEQ ID NO: 12.

12. The yeast cell of claim 1, further comprising genetic modification that decreases activity of a polypeptide converting pyruvate to acetaldehyde, a polypeptide converting lactate to pyruvate, a polypeptide converting dihydroxyacetone phosphate (DHAP) to glycerol-3-phosphate, an external mitochondrial NADH dehydrogenase, or a combination thereof.

13. The yeast cell of claim 12, in which a gene that encodes a polypeptide converting pyruvate to acetaldehyde, a gene that encodes a polypeptide converting lactate to pyruvate, a gene that encodes a polypeptide converting dihydroxyacetone phosphate (DHAP) to glycerol-3-phosphate, a gene that encodes an external mitochondrial NADH dehydrogenase, or a combination thereof are removed or disrupted.

14. The yeast cell of claim 13, wherein each of the polypeptide converting pyruvate to acetaldehyde, polypeptide converting lactate to pyruvate, polypeptide converting DHAP to glycerol-3-phosphate, and external mitochondrial NADH dehydrogenase has an amino acid sequence of at least 95% of sequence identity with one of SEQ ID NO: 15, 17, 19, 21, or 22.

15. The yeast cell of claim 13, wherein each of the genes that encode the polypeptide converting pyruvate to acetaldehyde, polypeptide converting lactate to pyruvate, a polypeptide converting DHAP to glycerol-3-phosphate, and external mitochondrial NADH dehydrogenase has the polynucleotide sequence of SEQ ID NO: 16, 18, 20, 23, or 24.

16. A method of producing lactate, the method comprising
   culturing the yeast cell of claim 1 in a medium to produce a culture; and
   collecting lactate from the culture,
   wherein the yeast cell comprises a genetic modification that increases activity of an enzyme, which catalyzes formation of the organic acid.

17. The method of claim 16, wherein the genetic modification comprises increasing the copy number of a polynucleotide that encodes lactate dehydrogenase.

18. The method of claim 16, wherein the culturing of the yeast cell is performed under an acidic condition for a predetermined period of time to perform whole or partial culturing.

* * * * *

SEQUENCE LISTING

```
<160> NUMBER OF SEQ ID NOS: 79

<210> SEQ ID NO 1
<211> LENGTH: 401
<212> TYPE: PRT
<213> ORGANISM: Saccharomyces cerevisiae
<220> FEATURE:
<221> NAME/KEY: misc_feature
<222> LOCATION: (1)..(401)
<223> OTHER INFORMATION: AUR1 amino acid

<400> SEQUENCE: 1

Met Ala Asn Pro Phe Ser Arg Trp Phe Leu Ser Glu Arg Pro Asn
 1               5                  10                  15

Cys His Val Ala Asp Leu Glu Thr Ser Leu Asp Pro His Gln Thr Leu
                20                  25                  30

Leu Lys Val Gln Lys Tyr Lys Pro Ala Leu Ser Asp Trp Val His Tyr
            35                  40                  45

Ile Phe Leu Gly Ser Ile Met Leu Phe Val Phe Ile Thr Asn Pro Ala
        50                  55                  60

Pro Trp Ile Phe Lys Ile Leu Phe Tyr Cys Phe Leu Gly Thr Leu Phe
65                  70                  75                  80

Ile Ile Pro Ala Thr Ser Gln Phe Phe Phe Asn Ala Leu Pro Ile Leu
                85                  90                  95
```

-continued

```
Thr Trp Val Ala Leu Tyr Phe Thr Ser Ser Tyr Phe Pro Asp Asp Arg
                100                 105                 110

Arg Pro Pro Ile Thr Val Lys Val Leu Pro Ala Val Glu Thr Ile Leu
            115                 120                 125

Tyr Gly Asp Asn Leu Ser Asp Ile Leu Ala Thr Ser Thr Asn Ser Phe
        130                 135                 140

Leu Asp Ile Leu Ala Trp Leu Pro Tyr Gly Leu Phe His Tyr Gly Ala
145                 150                 155                 160

Pro Phe Val Val Ala Ala Ile Leu Phe Val Phe Gly Pro Pro Thr Val
                165                 170                 175

Leu Gln Gly Tyr Ala Phe Ala Phe Gly Tyr Met Asn Leu Phe Gly Val
            180                 185                 190

Ile Met Gln Asn Val Phe Pro Ala Ala Pro Pro Trp Tyr Lys Ile Leu
        195                 200                 205

Tyr Gly Leu Gln Ser Ala Asn Tyr Asp Met His Gly Ser Pro Gly Gly
210                 215                 220

Leu Ala Arg Ile Asp Lys Leu Leu Gly Ile Asn Met Tyr Thr Thr Ala
225                 230                 235                 240

Phe Ser Asn Ser Ser Val Ile Phe Gly Ala Phe Pro Ser Leu His Ser
                245                 250                 255

Gly Cys Ala Thr Met Glu Ala Leu Phe Phe Cys Tyr Cys Phe Pro Lys
            260                 265                 270

Leu Lys Pro Leu Phe Ile Ala Tyr Val Cys Trp Leu Trp Trp Ser Thr
        275                 280                 285

Met Tyr Leu Thr His His Tyr Phe Val Asp Leu Met Ala Gly Ser Val
290                 295                 300

Leu Ser Tyr Val Ile Phe Gln Tyr Thr Lys Tyr Thr His Leu Pro Ile
305                 310                 315                 320

Val Asp Thr Ser Leu Phe Cys Arg Trp Ser Tyr Thr Ser Ile Glu Lys
                325                 330                 335

Tyr Asp Ile Ser Lys Ser Asp Pro Leu Ala Ala Asp Ser Asn Asp Ile
            340                 345                 350

Glu Ser Val Pro Leu Ser Asn Leu Glu Leu Asp Phe Asp Leu Asn Met
        355                 360                 365

Thr Asp Glu Pro Ser Val Ser Pro Ser Leu Phe Asp Gly Ser Thr Ser
    370                 375                 380

Val Ser Arg Ser Ser Ala Thr Ser Ile Thr Ser Leu Gly Val Lys Arg
385                 390                 395                 400

Ala

<210> SEQ ID NO 2
<211> LENGTH: 1206
<212> TYPE: DNA
<213> ORGANISM: Saccharomyces cerevisiae
<220> FEATURE:
<221> NAME/KEY: misc_feature
<222> LOCATION: (1)..(1206)
<223> OTHER INFORMATION: AUR1 gene

<400> SEQUENCE: 2
atggcaaacc cttttttcgag atggtttcta tcagagagac ctccaaactg ccatgtagcc      60
gatttagaaa caagtttaga tccccatcaa acgttgttga aggtgcaaaa atacaaaccc     120
gctttaagcg actgggtgca ttacatcttc ttgggatcca tcatgctgtt tgtgttcatt     180
actaatcccg cacccttggat cttcaagatc cttttttatt gtttcttggg cactttattc    240
```

```
atcattccag ctacgtcaca gttttctttc aatgccttgc ccatcctaac atgggtggcg    300
ctgtatttca cttcatcgta ctttccagat gaccgcaggc ctcctattac tgtcaaagtg    360
ttaccagcgg tggaaacaat tttatacggc gacaatttaa gtgatattct tgcaacatcg    420
acgaattcct ttttggacat tttagcatgg ttaccgtacg gactatttca ttatggggcc    480
ccatttgtcg ttgctgccat cttattcgta tttggtccac caactgtttt gcaaggttat    540
gcttttgcat ttggttatat gaacctgttt ggtgttatca tgcaaaatgt ctttccagcc    600
gctcccccat ggtataaaat tctctatgga ttgcaatcag ccaactatga tatgcatggc    660
tcgcctggtg gattagctag aattgataag ctactcggta ttaatatgta tactacagct    720
ttttcaaatt cctccgtcat tttcggtgct tttccttcac tgcattccgg gtgtgctact    780
atggaagccc tgttttttctg ttattgtttt ccaaaattga agccttgtt tattgcttat    840 gtttgctggt tatggtggtc aactatgtat ctgacacacc attattttgt agaccttatg    900
gcaggttctg tgctgtcata cgttattttc cagtacacaa agtacacaca tttaccaatt    960
gtagatacat ctcttttttg cagatggtca tacacttcaa ttgagaaata cgatatatca   1020
aagagtgatc cattggctgc agattcaaac gatatcgaaa gtgtcccttt gtccaacttg   1080
gaacttgact ttgatcttaa tatgactgat gaacccagtg taagcccttc gttatttgat   1140
ggatctactt ctgtttctcg ttcgtccgcc acgtctataa cgtcactagg tgtaaagagg   1200
gcttaa                                                              1206
```

<210> SEQ ID NO 3
<211> LENGTH: 510
<212> TYPE: PRT
<213> ORGANISM: Saccharomyces cerevisiae
<220> FEATURE:
<221> NAME/KEY: misc_feature
<222> LOCATION: (1)..(510)
<223> OTHER INFORMATION: OLE1 amino acid

<400> SEQUENCE: 3

```
Met Pro Thr Ser Gly Thr Thr Ile Glu Leu Ile Asp Asp Gln Phe Pro
  1               5                  10                  15

Lys Asp Asp Ser Ala Ser Ser Gly Ile Val Asp Glu Val Asp Leu Thr
             20                  25                  30

Glu Ala Asn Ile Leu Ala Thr Gly Leu Asn Lys Lys Ala Pro Arg Ile
         35                  40                  45

Val Asn Gly Phe Gly Ser Leu Met Gly Ser Lys Glu Met Val Ser Val
     50                  55                  60

Glu Phe Asp Lys Lys Gly Asn Glu Lys Lys Ser Asn Leu Asp Arg Leu
 65                  70                  75                  80

Leu Glu Lys Asp Asn Gln Glu Lys Glu Glu Ala Lys Thr Lys Ile His
                 85                  90                  95

Ile Ser Glu Gln Pro Trp Thr Leu Asn Asn Trp His Gln His Leu Asn
            100                 105                 110

Trp Leu Asn Met Val Leu Val Cys Gly Met Pro Met Ile Gly Trp Tyr
        115                 120                 125

Phe Ala Leu Ser Gly Lys Val Pro Leu His Leu Asn Val Phe Leu Phe
    130                 135                 140

Ser Val Phe Tyr Tyr Ala Val Gly Gly Val Ser Ile Thr Ala Gly Tyr
145                 150                 155                 160

His Arg Leu Trp Ser His Arg Ser Tyr Ser Ala His Trp Pro Leu Arg
                165                 170                 175
```

```
Leu Phe Tyr Ala Ile Phe Gly Cys Ala Ser Val Glu Gly Ser Ala Lys
                180                 185                 190

Trp Trp Gly His Ser His Arg Ile His His Arg Tyr Thr Asp Thr Leu
            195                 200                 205

Arg Asp Pro Tyr Asp Ala Arg Arg Gly Leu Trp Tyr Ser His Met Gly
        210                 215                 220

Trp Met Leu Leu Lys Pro Asn Pro Lys Tyr Lys Ala Arg Ala Asp Ile
225                 230                 235                 240

Thr Asp Met Thr Asp Trp Thr Ile Arg Phe Gln His Arg His Tyr
                245                 250                 255

Ile Leu Leu Met Leu Leu Thr Ala Phe Val Ile Pro Thr Leu Ile Cys
            260                 265                 270

Gly Tyr Phe Phe Asn Asp Tyr Met Gly Gly Leu Ile Tyr Ala Gly Phe
        275                 280                 285

Ile Arg Val Phe Val Ile Gln Gln Ala Thr Phe Cys Ile Asn Ser Leu
        290                 295                 300

Ala His Tyr Ile Gly Thr Gln Pro Phe Asp Asp Arg Arg Thr Pro Arg
305                 310                 315                 320

Asp Asn Trp Ile Thr Ala Ile Val Thr Phe Gly Glu Gly Tyr His Asn
                325                 330                 335

Phe His His Glu Phe Pro Thr Asp Tyr Arg Asn Ala Ile Lys Trp Tyr
            340                 345                 350

Gln Tyr Asp Pro Thr Lys Val Ile Ile Tyr Leu Thr Ser Leu Val Gly
        355                 360                 365

Leu Ala Tyr Asp Leu Lys Lys Phe Ser Gln Asn Ala Ile Glu Glu Ala
    370                 375                 380

Leu Ile Gln Gln Glu Gln Lys Lys Ile Asn Lys Lys Ala Lys Ile
385                 390                 395                 400

Asn Trp Gly Pro Val Leu Thr Asp Leu Pro Met Trp Asp Lys Gln Thr
                405                 410                 415

Phe Leu Ala Lys Ser Lys Glu Asn Lys Gly Leu Val Ile Ile Ser Gly
            420                 425                 430

Ile Val His Asp Val Ser Gly Tyr Ile Ser Glu His Pro Gly Gly Glu
        435                 440                 445

Thr Leu Ile Lys Thr Ala Leu Gly Lys Asp Ala Thr Lys Ala Phe Ser
450                 455                 460

Gly Gly Val Tyr Arg His Ser Asn Ala Ala Gln Asn Val Leu Ala Asp
465                 470                 475                 480

Met Arg Val Ala Val Ile Lys Glu Ser Lys Asn Ser Ala Ile Arg Met
                485                 490                 495

Ala Ser Lys Arg Gly Glu Ile Tyr Glu Thr Gly Lys Phe Phe
            500                 505                 510

<210> SEQ ID NO 4
<211> LENGTH: 1533
<212> TYPE: DNA
<213> ORGANISM: Saccharomyces cerevisiae
<220> FEATURE:
<221> NAME/KEY: misc_feature
<222> LOCATION: (1)..(1533)
<223> OTHER INFORMATION: OLE1 gene

<400> SEQUENCE: 4
atgccaactt ctggaactac tattgaattg attgacgacc aatttccaaa ggatgactct      60
gccagcagtg gcattgtcga cgaagtcgac ttaacggaag ctaatatttt ggctactggt     120
```

```
ttgaataaga aagcaccaag aattgtcaac ggttttggtt ctttaatggg ctccaaggaa    180
atggtttccg tggaattcga caagaaggga acgaaaaga agtccaattt ggatcgtctg     240
ctagaaaagg acaaccaaga aaaagaagaa gctaaaacta aaattcacat ctccgaacaa    300
ccatggactt tgaataactg gcaccaacat ttgaactggt tgaacatggt tcttgtttgt    360
ggtatgccaa tgattggttg gtacttcgct ctctctggta agtacccttt gcatttaaac    420
gttttccttt tctccgtttt ctactacgct gtcggtggtg tttctattac tgccggttac    480
catagattat ggtctcacag atcttactcc gctcactggc cattgagatt attctacgct    540
atcttcggtt gtgcttccgt tgaagggtcc gctaaatggt ggggccactc tcacagaatt    600
caccatcgtt acactgatac cttgagagat ccttatgacg ctcgtagagg tctatggtac    660
tcccacatgg gatggatgct tttgaagcca aatccaaaat acaaggctag agctgatatt    720
accgatatga ctgatgattg gaccattaga ttccaacaca gacactacat cttgttgatg    780
ttattaaccg ctttcgtcat tccaactctt atctgtggtt acttttttcaa cgactatatg    840 ggtggtttga tctatgccgg ttttattcgt gtctttgtca ttcaacaagc tacctttttgc   900 attaactcca tggctcatta catcggtacc caaccattcg atgacagaag aaccccctcgt  960 gacaactgga ttactgccat tgttactttc ggtgaaggtt accataactt ccaccacgaa   1020
ttcccaactg attacagaaa cgctattaag tggtaccaat cgacccaac taaggttatc    1080 atctatttga cttctttagt tggtctagca tacgacttga agaaattctc tcaaaatgct   1140
attgaagaag ccttgattca acaagaacaa aagaagatca ataaaagaa ggctaagatt    1200 aactggggtc cagtttttgac tgatttgcca atgtgggaca acaaacctt cttggctaag   1260 tctaaggaaa acaagggttt ggttatcatt tctggtattg ttcacgacgt atctggttat   1320
atctctgaac atccaggtgg tgaaactta attaaaactg cattaggtaa ggacgctacc    1380
aaggctttca gtggtggtgt ctaccgtcac tcaaatgccg ctcaaaatgt cttggctgat   1440
atgagagtgg ctgttatcaa ggaaagtaag aactctgcta ttagaatggc tagtaagaga   1500
ggtgaaatct acgaaactgg taagttcttt taa                                1533
```

<210> SEQ ID NO 5
<211> LENGTH: 594
<212> TYPE: PRT
<213> ORGANISM: Pichia kudriavzevii
<220> FEATURE:
<221> NAME/KEY: misc_feature
<222> LOCATION: (1)..(594)
<223> OTHER INFORMATION: OLE1 amino acid

<400> SEQUENCE: 5

Met Asp Ser Val Asp Ile Thr Gln Ala Asn Ala Val Ala Ala Gly Thr
 1               5                   10                  15

Asn Lys Pro Val Lys Arg Ile Val Ala Ser Gly Ile Gly Gly Arg Leu
                20                  25                  30

Met Gly Thr Lys Ala Met Thr Thr Val Thr Ala Glu Glu Leu Ala Arg
            35                  40                  45

Asp Ser Val Ala Glu Val Leu Lys Arg Asp Ser Glu Leu Arg Val Lys
        50                  55                  60

Tyr Glu Lys Glu Gln His Ile Ser Glu Lys Asp Trp Ser Phe Asp Thr
 65                  70                  75                  80

Phe Phe Gln Lys Ile Asn Trp Leu Asn Leu Tyr Leu Val Val Ala Phe
                85                  90                  95

Pro Leu Phe Ala Ile Ala Gly Phe Ile Met Asp Ser Val Asp Ile Thr

```
            100                 105                 110
Gln Ala Asn Ala Val Ala Gly Thr Asn Lys Pro Val Lys Arg Ile
        115                 120                 125
Val Ala Ser Gly Ile Gly Gly Arg Leu Met Gly Thr Lys Ala Met Thr
        130                 135                 140
Thr Val Thr Ala Glu Glu Leu Ala Arg Asp Ser Val Ala Glu Val Leu
145                 150                 155                 160
Lys Arg Asp Ser Glu Leu Arg Val Lys Tyr Glu Lys Glu Gln His Ile
                165                 170                 175
Ser Glu Lys Asp Trp Ser Phe Asp Thr Phe Gln Lys Ile Asn Trp
                180                 185                 190
Leu Asn Leu Tyr Leu Val Val Ala Phe Pro Leu Phe Ala Ile Ala Gly
            195                 200                 205
Ala Ile Tyr Phe Gln Ile Lys Pro Thr Ile Gln Thr Val Thr Leu Gly
        210                 215                 220
Val Ile Leu Phe Ser Leu Ser Gly Leu Ser Ile Thr Ala Gly Tyr His
225                 230                 235                 240
Arg Leu Trp Ser His Arg Ala Tyr Asp Ala Lys Asp Pro Leu Lys Ile
                245                 250                 255
Val Phe Ala Leu Phe Gly Ala Ala Ile Glu Gly Ser Ile Lys Trp
                260                 265                 270
Trp Gly His Ser His Arg Ile His His Arg Tyr Thr Asp Thr Asp Arg
            275                 280                 285
Asp Pro Tyr Asp Ala Arg Lys Gly Phe Trp Tyr Ser His Ile Gly Trp
        290                 295                 300
Met Leu Leu Val Pro Asn Pro Lys Tyr Lys Ala Arg Ala Asp Ile Ser
305                 310                 315                 320
Asp Leu Val Asp Asp Trp Ile Val Arg Val Gln His Arg His Tyr Leu
                325                 330                 335
Ser Ile Met Leu Ile Met Gly Leu Val Val Pro Ala Leu Leu Ser His
            340                 345                 350
Tyr Leu Trp Asn Asp Phe Trp Gly Gly Leu Ile Tyr Ala Gly Leu Leu
        355                 360                 365
Lys Ser Ser Ala Ile Gln Gln Ala Thr Phe Cys Val Asn Ser Leu Ala
        370                 375                 380
His Trp Ile Gly Glu Gln Pro Phe Asp Asp Arg Arg Thr Pro Arg Asp
385                 390                 395                 400
His Phe Leu Thr Ala Leu Val Thr Phe Gly Glu Gly Tyr His Asn Phe
                405                 410                 415
His His Glu Phe Pro Ser Asp Tyr Arg Asn Ala Leu Lys Trp Tyr Gln
                420                 425                 430
Tyr Asp Pro Thr Lys Ile Leu Ile Trp Cys Ala Ser Lys Val Gly Leu
            435                 440                 445
Ala Tyr Asn Leu Lys Lys Phe Ser Gln Asn Ala Ile Asp Gln Gly Ile
        450                 455                 460
Leu Gln Gln Lys Gln Lys Lys Leu Asp Glu Met Arg Ser Lys Leu Asn
465                 470                 475                 480
Trp Gly Pro Gln Ile Ala Asp Leu Pro Ile Trp Thr Lys Glu Glu Phe
                485                 490                 495
Lys Glu Lys Ala Ala Gln Lys Lys Gly Tyr Ile Ile Ile Ser Gly Ile
                500                 505                 510
Val His Asp Cys Ser Ser Phe Ile Thr Glu His Pro Gly Gly Gln Ala
            515                 520                 525
```

Leu Val Arg Thr Ser Tyr Gly Lys Asp Ala Thr Val Ala Phe Asn Gly
        530                 535                 540

Gly Val Tyr Ala His Ser Asn Ala Ala His Asn Leu Leu Ser Thr Leu
545                 550                 555                 560

Arg Val Ala Val Ile Lys Asp Ser Gly Ala Asn Gly Asn Thr Tyr Ser
                565                 570                 575

Arg Gln Leu Glu Tyr Leu Ala Lys Thr Glu Lys Glu Gln Met Ser Lys
            580                 585                 590

Ser Asn

<210> SEQ ID NO 6
<211> LENGTH: 1785
<212> TYPE: DNA
<213> ORGANISM: Pichia kudriavzevii
<220> FEATURE:
<221> NAME/KEY: misc_feature
<222> LOCATION: (1)..(1785)
<223> OTHER INFORMATION: OLE1 gene

<400> SEQUENCE: 6

| | | | | | |
|---|---|---|---|---|---|
| atggacagtg | ttgatatcac | acaggctaat | gccgttgcag | ccggcacaaa | taaaccggtc | 60 |
| aagagaattg | tcgcctcagg | tattggaggc | cgtctgatgg | gtacaaaggc | tatgactact | 120 |
| gtgacagcag | aagaattggc | tcgggattcg | gttgccgaag | ttttgaaaag | ggactctgaa | 180 |
| ctaagggtca | agtatgagaa | ggaacaacac | atctcggaga | agattggtc | ctttgatact | 240 |
| ttttttccaaa | aaatcaactg | gctgaacttg | taccttgttg | ttgcatttcc | tttatttgca | 300 |
| attgcaggtt | ttataatgga | cagtgttgat | atcacacagg | ctaatgccgt | tgcagccggc | 360 |
| acaaataaac | cggtcaagag | aattgtcgcc | tcaggtattg | gaggccgtct | gatgggtaca | 420 |
| aaggctatga | ctactgtgac | agcagaagaa | ttggctcggg | attcggttgc | cgaagttttg | 480 |
| aaaagggact | ctgaactaag | ggtcaagtat | gagaaggaac | aacacatctc | ggagaaagat | 540 |
| tggtcctttg | atactttttt | ccaaaaaatc | aactggctga | acttgtacct | tgttgttgca | 600 |
| tttcctttat | ttgcaattgc | aggtgcaatt | tatttccaaa | ttaagccaac | tattcaaaca | 660 |
| gtcactttag | gtgttattct | cttttcattg | agtgggttgt | ccatcactgc | tggttaccac | 720 |
| agactatggt | ctcatcgtgc | ttatgatgca | aaggatccat | aaagattgt | ctttgctctc | 780 |
| tttggtgccg | ctgctattga | aggttccatc | aaatggtggg | tcattctca | tcggatccat | 840 |
| catagatata | ccgataccga | ccgtgatcca | tacgatgcaa | gaaagggatt | ctggtattcc | 900 |
| catattggat | ggatgttgtt | ggttcctaat | cctaaatata | aggcaagagc | agacatttcc | 960 |
| gatttagttg | acgactggat | tgtcagagtc | caacatagac | actacttatc | tatcatgttg | 1020 |
| attatgggtc | tggtggtccc | tgctttatta | tcccactatt | tatggaacga | tttctgggg | 1080 |
| ggcttgattt | atgcaggtct | cttaaaatct | tctgctattc | aacaagctac | attttgtgtg | 1140 |
| aactctctag | cccactggat | tggtgagcaa | ccatttgatg | acagaagaac | cccaagagac | 1200 |
| catttcttga | cggctttggt | cactttggt | gaaggttatc | ataactttca | tcatgagttt | 1260 |
| ccttcggatt | atagaaatgc | ccttaaatgg | taccaatacg | atccaaccaa | gatttttgatt | 1320 |
| tggtgtgcat | ccaaggttgg | acttgcgtac | aatttgaaga | agttttctca | aaatgccatt | 1380 |
| gatcaaggaa | tacttcaaca | gaagcagaag | aaacttgacg | aaatgagatc | caaattaaac | 1440 |
| tggggtcctc | aaattgcaga | cttgccaatt | tggacaaagg | aagaatttaa | ggaaaaggct | 1500 |
| gcacaaaaga | agggttacat | tattatctct | ggcattgtcc | atgactgttc | ctcttttatt | 1560 |

```
actgaacatc caggtggtca ggcattagtt cgtacctcct atggtaaaga tgctacggtg    1620
gcattcaatg gaggtgttta tgcccattcc aacgctgccc ataacttgtt atcgacgttg    1680
agagtcgccg ttattaagga ttcgggcgcc aatggtaata cctactcgag acaactggaa    1740
tacttggcta aaaccgaaaa ggaacagatg tccaaatcca actaa                    1785
```

<210> SEQ ID NO 7
<211> LENGTH: 418
<212> TYPE: PRT
<213> ORGANISM: Saccharomyces cerevisiae
<220> FEATURE:
<221> NAME/KEY: misc_feature
<222> LOCATION: (1)..(418)
<223> OTHER INFORMATION: DGA1 amino acid

<400> SEQUENCE: 7

```
Met Ser Gly Thr Phe Asn Asp Ile Arg Arg Arg Lys Lys Glu Glu Gly
 1               5                  10                  15

Ser Pro Thr Ala Gly Ile Thr Glu Arg His Glu Asn Lys Ser Leu Ser
            20                  25                  30

Ser Ile Asp Lys Arg Glu Gln Thr Leu Lys Pro Gln Leu Glu Ser Cys
        35                  40                  45

Cys Pro Leu Ala Thr Pro Phe Glu Arg Arg Leu Gln Thr Leu Ala Val
    50                  55                  60

Ala Trp His Thr Ser Ser Phe Val Leu Phe Ser Ile Phe Thr Leu Phe
65                  70                  75                  80

Ala Ile Ser Thr Pro Ala Leu Trp Val Leu Ala Ile Pro Tyr Met Ile
                85                  90                  95

Tyr Phe Phe Phe Asp Arg Ser Pro Ala Thr Gly Glu Val Val Asn Arg
            100                 105                 110

Tyr Ser Leu Arg Phe Arg Ser Leu Pro Ile Trp Lys Trp Tyr Cys Asp
        115                 120                 125

Tyr Phe Pro Ile Ser Leu Ile Lys Thr Val Asn Leu Lys Pro Thr Phe
    130                 135                 140

Thr Leu Ser Lys Asn Lys Arg Val Asn Glu Lys Asn Tyr Lys Ile Arg
145                 150                 155                 160

Leu Trp Pro Thr Lys Tyr Ser Ile Asn Leu Lys Ser Asn Ser Thr Ile
                165                 170                 175

Asp Tyr Arg Asn Gln Glu Cys Thr Gly Pro Thr Tyr Leu Phe Gly Tyr
            180                 185                 190

His Pro His Gly Ile Gly Ala Leu Gly Ala Phe Gly Ala Phe Ala Thr
        195                 200                 205

Glu Gly Cys Asn Tyr Ser Lys Ile Phe Pro Gly Ile Pro Ile Ser Leu
    210                 215                 220

Met Thr Leu Val Thr Gln Phe His Ile Pro Leu Tyr Arg Asp Tyr Leu
225                 230                 235                 240

Leu Ala Leu Gly Ile Ser Ser Val Ser Arg Lys Asn Ala Leu Arg Thr
                245                 250                 255

Leu Ser Lys Asn Gln Ser Ile Cys Ile Val Val Gly Gly Ala Arg Glu
            260                 265                 270

Ser Leu Leu Ser Ser Thr Asn Gly Thr Gln Leu Ile Leu Asn Lys Arg
        275                 280                 285

Lys Gly Phe Ile Lys Leu Ala Ile Gln Thr Gly Asn Ile Asn Leu Val
    290                 295                 300

Pro Val Phe Ala Phe Gly Glu Val Asp Cys Tyr Asn Val Leu Ser Thr
305                 310                 315                 320
```

```
Lys Lys Asp Ser Val Leu Gly Lys Met Gln Leu Trp Phe Lys Glu Asn
            325                 330                 335

Phe Gly Phe Thr Ile Pro Ile Phe Tyr Ala Arg Gly Leu Phe Asn Tyr
            340                 345                 350

Asp Phe Gly Leu Leu Pro Phe Arg Ala Pro Ile Asn Val Val Val Gly
            355                 360                 365

Arg Pro Ile Tyr Val Glu Lys Lys Ile Thr Asn Pro Pro Asp Asp Val
        370                 375                 380

Val Asn His Phe His Asp Leu Tyr Ile Ala Glu Leu Lys Arg Leu Tyr
385                 390                 395                 400

Tyr Glu Asn Arg Glu Lys Tyr Gly Val Pro Asp Ala Glu Leu Lys Ile
                405                 410                 415

Val Gly

<210> SEQ ID NO 8
<211> LENGTH: 1257
<212> TYPE: DNA
<213> ORGANISM: Saccharomyces cerevisiae
<220> FEATURE:
<221> NAME/KEY: misc_feature
<222> LOCATION: (1)..(1257)
<223> OTHER INFORMATION: DGA1 gene

<400> SEQUENCE: 8
atgtcaggaa cattcaatga tataagaaga aggaagaagg aagaaggaag ccctacagcc      60
ggtattaccg aaaggcatga gaataagtct ttgtcaagca tcgataaaag agaacagact     120
ctcaaaccac aactagagtc atgctgtcca ttggcgaccc cttttgaaag aaggttacaa     180
actctggctg tagcatggca cacttcttca tttgtactct tctccatatt tacgttattt     240
gcaatctcga caccagcact gtgggttctt gctattccat atatgattta ttttttttc      300 gataggtctc ctgcaactgg cgaagtggta aatcgatact ctcttcgatt tcgttcattg     360
cccatttgga agtggtattg tgattatttc cctataagtt tgattaaaac tgtcaattta     420
aaaccaactt ttacgctttc aaaaaaataag agagttaacg aaaaaaatta caagattaga     480
ttgtggccaa ctaagtattc cattaatctc aaaagcaact ctactattga ctatcgcaac     540
caggaatgta cagggccaac gtacttattt ggttaccatc cacacggcat aggagcactt     600
ggtgcgtttg gagcgtttgc aacagaaggt tgtaactatt ccaagatttt cccaggtatt     660
cctatttctc tgatgacact ggtcacacaa tttcatatcc cattgtatag agactactta     720
ttggcgttag gtatttcttc agtatctcgg aaaaacgctt taaggactct aagcaaaaat     780
cagtcgatct gcattgttgt tggtggcgct agggaatctt tattaagttc aacaaatggt     840
acacaactga ttttaaacaa agaaagggt tttattaaac tggccattca acgggggaat      900
attaacctag tgcctgtgtt tgcatttgga gaggtggact gttataatgt tctgagcaca     960
aaaaaagatt cagtcctggg taaaatgcaa ctatggttca agaaaacttt ggttttacc     1020 attcccattt tctacgcaag aggattattc aattacgatt tcggtttgtt gccatttaga    1080
gcgcctatca atgttgttgt tggaaggcct atatacgttg aaaagaaaat aacaaatccg    1140
ccagatgatg ttgttaatca tttccatgat ttgtatattg cggagttgaa aagactatat    1200
tacgaaaata gagaaaaata tggggtaccg gatgcagaat tgaagatagt tgggtaa      1257

<210> SEQ ID NO 9
<211> LENGTH: 661
<212> TYPE: PRT
```

<213> ORGANISM: Saccharomyces cerevisiae
<220> FEATURE:
<221> NAME/KEY: misc_feature
<222> LOCATION: (1)..(661)
<223> OTHER INFORMATION: LRO1 amino acid

<400> SEQUENCE: 9

```
Met Gly Thr Leu Phe Arg Arg Asn Val Gln Asn Gln Lys Ser Asp Ser
 1               5                  10                  15

Asp Glu Asn Asn Lys Gly Gly Ser Val His Asn Lys Arg Glu Ser Arg
                20                  25                  30

Asn His Ile His His Gln Gln Gly Leu Gly His Lys Arg Arg Arg Gly
            35                  40                  45

Ile Ser Gly Ser Ala Lys Arg Asn Glu Arg Gly Lys Asp Phe Asp Arg
        50                  55                  60

Lys Arg Asp Gly Asn Gly Arg Lys Arg Trp Arg Asp Ser Arg Arg Leu
65                  70                  75                  80

Ile Phe Ile Leu Gly Ala Phe Leu Gly Val Leu Leu Pro Phe Ser Phe
                85                  90                  95

Gly Ala Tyr His Val His Asn Ser Asp Ser Asp Leu Phe Asp Asn Phe
                100                 105                 110

Val Asn Phe Asp Ser Leu Lys Val Tyr Leu Asp Asp Trp Lys Asp Val
            115                 120                 125

Leu Pro Gln Gly Ile Ser Ser Phe Ile Asp Asp Ile Gln Ala Gly Asn
130                 135                 140

Tyr Ser Thr Ser Ser Leu Asp Asp Leu Ser Glu Asn Phe Ala Val Gly
145                 150                 155                 160

Lys Gln Leu Leu Arg Asp Tyr Asn Ile Glu Ala Lys His Pro Val Val
                165                 170                 175

Met Val Pro Gly Val Ile Ser Thr Gly Ile Glu Ser Trp Gly Val Ile
            180                 185                 190

Gly Asp Asp Glu Cys Asp Ser Ser Ala His Phe Arg Lys Arg Leu Trp
        195                 200                 205

Gly Ser Phe Tyr Met Leu Arg Thr Met Val Met Asp Lys Val Cys Trp
    210                 215                 220

Leu Lys His Val Met Leu Asp Pro Glu Thr Gly Leu Asp Pro Pro Asn
225                 230                 235                 240

Phe Thr Leu Arg Ala Ala Gln Gly Phe Glu Ser Thr Asp Tyr Phe Ile
                245                 250                 255

Ala Gly Tyr Trp Ile Trp Asn Lys Val Phe Gln Asn Leu Gly Val Ile
            260                 265                 270

Gly Tyr Glu Pro Asn Lys Met Thr Ser Ala Ala Tyr Asp Trp Arg Leu
        275                 280                 285

Ala Tyr Leu Asp Leu Glu Arg Arg Asp Arg Tyr Phe Thr Lys Leu Lys
    290                 295                 300

Glu Gln Ile Glu Leu Phe His Gln Leu Ser Gly Glu Lys Val Cys Leu
305                 310                 315                 320

Ile Gly His Ser Met Gly Ser Gln Ile Ile Phe Tyr Phe Met Lys Trp
                325                 330                 335

Val Glu Ala Glu Gly Pro Leu Tyr Gly Asn Gly Gly Arg Gly Trp Val
            340                 345                 350

Asn Glu His Ile Asp Ser Phe Ile Asn Ala Ala Gly Thr Leu Leu Gly
        355                 360                 365

Ala Pro Lys Ala Val Pro Ala Leu Ile Ser Gly Glu Met Lys Asp Thr
    370                 375                 380
```

Ile Gln Leu Asn Thr Leu Ala Met Tyr Gly Leu Glu Lys Phe Phe Ser
385                 390                 395                 400

Arg Ile Glu Arg Val Lys Met Leu Gln Thr Trp Gly Gly Ile Pro Ser
            405                 410                 415

Met Leu Pro Lys Gly Glu Val Ile Trp Gly Asp Met Lys Ser Ser
        420                 425                 430

Ser Glu Asp Ala Leu Asn Asn Asn Thr Asp Thr Tyr Gly Asn Phe Ile
        435                 440                 445

Arg Phe Glu Arg Asn Thr Ser Asp Ala Phe Asn Lys Asn Leu Thr Met
    450                 455                 460

Lys Asp Ala Ile Asn Met Thr Leu Ser Ile Ser Pro Glu Trp Leu Gln
465                 470                 475                 480

Arg Arg Val His Glu Gln Tyr Ser Phe Gly Tyr Ser Lys Asn Glu Glu
                485                 490                 495

Glu Leu Arg Lys Asn Glu Leu His His Lys His Trp Ser Asn Pro Met
            500                 505                 510

Glu Val Pro Leu Pro Glu Ala Pro His Met Lys Ile Tyr Cys Ile Tyr
        515                 520                 525

Gly Val Asn Asn Pro Thr Glu Arg Ala Tyr Val Tyr Lys Glu Asp
        530                 535                 540

Asp Ser Ser Ala Leu Asn Leu Thr Ile Asp Tyr Glu Ser Lys Gln Pro
545                 550                 555                 560

Val Phe Leu Thr Glu Gly Asp Gly Thr Val Pro Leu Val Ala His Ser
                565                 570                 575

Met Cys His Lys Trp Ala Gln Gly Ala Ser Pro Tyr Asn Pro Ala Gly
            580                 585                 590

Ile Asn Val Thr Ile Val Glu Met Lys His Gln Pro Asp Arg Phe Asp
        595                 600                 605

Ile Arg Gly Gly Ala Lys Ser Ala Glu His Val Asp Ile Leu Gly Ser
        610                 615                 620

Ala Glu Leu Asn Asp Tyr Ile Leu Lys Ile Ala Ser Gly Asn Gly Asp
625                 630                 635                 640

Leu Val Glu Pro Arg Gln Leu Ser Asn Leu Ser Gln Trp Val Ser Gln
                645                 650                 655

Met Pro Phe Pro Met
            660

<210> SEQ ID NO 10
<211> LENGTH: 1986
<212> TYPE: DNA
<213> ORGANISM: Saccharomyces cerevisiae
<220> FEATURE:
<221> NAME/KEY: misc_feature
<222> LOCATION: (1)..(1986)
<223> OTHER INFORMATION: LRO1 gene

<400> SEQUENCE: 10
atgggcacac tgtttcgaag aaatgtccag aaccaaaaga gtgattctga tgaaaacaat     60 aaaggggtt ctgttcataa caagcgagag agcagaaacc acattcatca tcaacaggga    120
ttaggccata agagaagaag gggtattagt ggcagtgcaa aaagaaatga gcgtggcaaa    180
gatttcgaca ggaaaagaga cgggaacggt agaaaacgtt ggagagattc cagaagactg    240
attttcattc ttggtgcatt cttaggtgta cttttgccgt ttagctttgg cgcttatcat    300
gttcataata gcgatagcga cttgtttgac aactttgtaa attttgattc acttaaagtg    360

```
tatttggatg attggaaaga tgttctccca caaggtataa gttcgtttat tgatgatatt    420
caggctggta actactccac atcttcttta gatgatctca gtgaaaattt tgccgttggt    480
aaacaactct tacgtgatta taatatcgag gccaaacatc ctgttgtaat ggttcctggt    540
gtcatttcta cgggaattga agctggggga gttattggag cgatgagtg cgatagttct    600 gcgcattttc gtaaacggct gtggggaagt ttttacatgc tgagaacaat ggttatggat    660
aaagtttgtt ggttgaaaca tgtaatgtta gatcctgaaa caggtctgga cccaccgaac    720
tttacgctac gtgcagcaca gggcttcgaa tcaactgatt atttcatcgc agggtattgg    780
atttggaaca agttttcca aaatctggga gtaattggct atgaacccaa taaaatgacg    840
agtgctgcgt atgattggag gcttgcatat ttagatctag aaagacgcga taggtacttt    900
acgaagctaa aggaacaaat cgaactgttt catcaattga gtggtgaaaa agtttgttta    960
attggacatt ctatgggttc tcagattatc ttttacttta tgaaatgggt cgaggctgaa   1020
ggccctcttt acggtaatgg tggtcgtggc tgggttaacg aacacataga ttcattcatt   1080
aatgcagcag ggacgcttct gggcgctcca aaggcagttc cagctctaat tagtggtgaa   1140
atgaaagata ccattcaatt aaatacgtta gccatgtatg gtttggaaaa gttcttctca   1200
agaattgaga gagtaaaaat gttacaaacg tggggtggta taccatcaat gctaccaaag   1260
ggagaagagg tcatttgggg ggatatgaag tcatcttcag aggatgcatt gaataacaac   1320
actgacacat acggcaattt cattcgattt gaaaggaata cgagcgatgc tttcaacaaa   1380
aatttgacaa tgaaagacgc cattaacatg acattatcga tatcacctga atggctccaa   1440
agaagagtac atgagcagta ctcgttcggc tattccaaga tgaagaaga gttaagaaaa   1500 aatgagctac accacaagca ctggtcgaat ccaatggaag taccacttcc agaagctccc   1560
cacatgaaaa tctattgtat atacggggtg aacaacccaa ctgaaagggc atatgtatat   1620
aaggaagagg atgactcctc tgctctgaat ttgaccatcg actacgaaag caagcaacct   1680
gtattcctca ccgaggggga cggaaccgtt ccgctcgtgg cgcattcaat gtgtcacaaa   1740
tgggcccagg gtgcttcacc gtacaaccct gccggaatta acgttactat tgtggaaatg   1800
aaacaccagc cagatcgatt tgatatacgt ggtggagcaa aaagcgccga acacgtagac   1860
atcctcggca gcgcggagtt gaacgattac atcttgaaaa ttgcaagcgg taatggcgat   1920
ctcgtcgagc cacgccaatt gtctaattg agccagtggg tttctcagat gcccttccca   1980
atgtaa                                                             1986
```

<210> SEQ ID NO 11
<211> LENGTH: 324
<212> TYPE: PRT
<213> ORGANISM: Sordaria macrospora

<400> SEQUENCE: 11

```
Met Ser Val Pro Ser Thr Glu Ile Ser Ser His Ala Lys Ser Ile Lys
  1               5                  10                  15

Val Val Ile Val Gly Ala Gly Ser Val Gly Val Thr Thr Ala Tyr Ala
                 20                  25                  30

Leu Leu Leu Ser His Leu Ala Pro Glu Ile Val Leu Ile Asp Ile Asp
             35                  40                  45

Lys Asn Arg Ala Leu Gly Glu Ala Met Asp Leu Ser His Ala Ala His
         50                  55                  60

Tyr Ala His Ala Lys Val Ser Val Gly Asn Tyr Glu Asp Cys Ala Gly
 65                  70                  75                  80
```

```
Ala Thr Ala Val Ile Ile Thr Ala Gly Val Asn Gln Lys Pro Gly Gln
                85                  90                  95

Thr Arg Met Asp Leu Val Lys Thr Asn Phe Gly Leu Phe Glu Lys Ile
            100                 105                 110

Val Pro Gln Ile Ala Lys His Ala Pro Asn Thr Ile Leu Ile Val Ala
        115                 120                 125

Thr Asn Pro Cys Asp Val Leu Thr Lys Ala Ala Gln Glu Leu Ser Gly
    130                 135                 140

Phe Pro Val Gln Arg Val Ile Gly Ser Gly Thr Ala Met Asp Thr Thr
145                 150                 155                 160

Arg Phe Arg His Glu Leu Gly Lys His Tyr Gly Val Asn Pro Arg Asn
                165                 170                 175

Val His Ala Val Ile Val Gly Glu His Gly Asp Ser Gln Leu Pro Val
            180                 185                 190

Trp Ser Leu Ala Thr Ile Ala Gly Met Arg Leu Glu Asp Tyr Cys Asn
        195                 200                 205

Gln Lys Gly Ile Ala Tyr Asp Glu Lys Ala Met Asp Ala Leu Gly Lys
    210                 215                 220

Arg Thr Arg Glu Ala Ala Tyr Glu Ile Ile Gln Arg Lys Gly Lys Thr
225                 230                 235                 240

Asn Tyr Gly Val Ala Ser Val Leu Val Ser Ile Leu Glu Pro Ile Ile
                245                 250                 255

Thr Asn Ala Asp Gln Leu Val Thr Val Ser Arg Val Gly Asn Tyr Ala
            260                 265                 270

Gly Val Glu Gly Val Ala Leu Ser Met Pro Cys Lys Leu Asn Ser Leu
        275                 280                 285

Gly Ala His Gln Asp Val Glu Leu Leu Leu Asn Asp Lys Glu Lys Glu
    290                 295                 300

Ala Leu Arg Lys Ser Ala Thr Ser Ile Lys Glu Cys Phe Asp Ser Val
305                 310                 315                 320

Ala Lys Lys Glu

<210> SEQ ID NO 12
<211> LENGTH: 975
<212> TYPE: DNA
<213> ORGANISM: Sordaria macrospora

<400> SEQUENCE: 12
atgagcgttc caagcacaga gatttcatct catgccaaat ctataaaggt tgtcatcgtt      60
ggtgcgggtt cagttggtgt cacaactgct tatgccttat tgctttcgca cttagcacca     120
gagatcgttc tgatcgacat tgataaaaat agagctttag agaggcaat ggacctgtca      180 catgcagctc attacgctca cgcaaaagtt agtgttggaa actatgagga ttgtgctggg     240
gccacagcag ttatcataac agctggtgtt aaccaaaagc cagggcaaac taggatggat     300
ttagtcaaaa caaactttgg actatttgag aagatagtgc cccaaatagc taagcacgcg     360
cctaatacta ttttaatagt cgctaccaat ccctgtgatg tcttaacaaa agcggcacag     420
gagttatcag gattccctgt acagagagtt atcggttctg gaaccgctat ggatactacc     480
cgtttcagac acgaactggg caagcattat ggagtaaatc caagaaacgt acatgctgtg     540
attgtaggtg aacatggtga ttcccaacta cctgtatggt ccttagctac tattgctggt     600
atgcgtttgg aagattattg caatcaaaaa ggtatagcct acgatgaaaa agctatggat     660
gccttgggta aagaactag ggaagcagca tacgaaatca ttcaaagaaa aggcaagacg      720
```

```
aattatggcg tggcatcggt ccttgtatct attttggaac cgattattac caatgcagac       780
caacttgtga ctgtctctag ggtgggcaat tacgccggtg tagaaggcgt ggctttaagt       840
atgccatgca aattgaacag tctaggtgcg catcaggacg ttgaattgtt gcttaacgac       900
aaggaaaaag aagccctacg taaatcagcc acgtccatta agaatgtttt tgattctgtt       960
gcaaagaagg aataa                                                        975

<210> SEQ ID NO 13
<211> LENGTH: 332
<212> TYPE: PRT
<213> ORGANISM: Pelodiscus sinensis japonicus

<400> SEQUENCE: 13
```

Met Ser Val Lys Glu Leu Leu Ile Gln Asn Val His Lys Glu His
 1               5                  10                  15

Ser His Ala His Asn Lys Ile Thr Val Val Gly Val Gly Ala Val Gly
             20                  25                  30

Met Ala Cys Ala Ile Ser Ile Leu Met Lys Asp Leu Ala Asp Glu Leu
         35                  40                  45

Ala Leu Val Asp Val Ile Glu Asp Lys Leu Arg Gly Glu Met Leu Asp
     50                  55                  60

Leu Gln His Gly Ser Leu Phe Leu Arg Thr Pro Lys Ile Val Ser Gly
 65                  70                  75                  80

Lys Asp Tyr Ser Val Thr Ala His Ser Lys Leu Val Ile Ile Thr Ala
                 85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125

Pro Asp Cys Met Leu Leu Val Val Ser Asn Pro Val Asp Ile Leu Thr
    130                 135                 140

Tyr Val Ala Trp Lys Ile Ser Gly Phe Pro Lys His Arg Val Ile Gly
145                 150                 155                 160

Ser Gly Cys Asn Leu Asp Ser Ala Arg Phe Arg Tyr Leu Met Gly Glu
                165                 170                 175

Lys Leu Gly Ile His Ser Leu Ser Cys His Gly Trp Ile Ile Gly Glu
            180                 185                 190

His Gly Asp Ser Ser Val Pro Val Trp Ser Gly Val Asn Val Ala Gly
        195                 200                 205

Val Ser Leu Lys Ala Leu Tyr Pro Asp Leu Gly Thr Asp Ala Asp Lys
    210                 215                 220

Glu His Trp Lys Glu Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Thr Val Met Lys Asn Leu Arg Arg Val His Pro
            260                 265                 270

Ile Ser Thr Met Val Lys Gly Met Tyr Gly Val Ser Ser Asp Val Phe
        275                 280                 285

Leu Ser Val Pro Cys Val Leu Gly Tyr Ala Gly Ile Thr Asp Val Val
    290                 295                 300

Lys Met Thr Leu Lys Ser Glu Glu Glu Lys Leu Arg Lys Ser Ala
305                 310                 315                 320

Asp Thr Leu Trp Gly Ile Gln Lys Glu Leu Gln Phe

<210> SEQ ID NO 14
<211> LENGTH: 999
<212> TYPE: DNA
<213> ORGANISM: Pelodiscus sinensis japonicus

<400> SEQUENCE: 14

```
atgtccgtaa aggaactact tatacaaaac gtccataagg aggagcattc tcacgctcac      60
aataagataa cagttgtagg agtaggtgca gtaggtatgg catgtgctat ttcgatatta     120
atgaaagact ggctgatga actagccttg gttgatgtga ttgaggataa gttacgtgga     180
gaaatgttag atttgcaaca tggttcattg ttcttgagaa cccccaaaat tgtctcgggt     240
aaggattatt cagtcactgc tcattctaaa ctggttatca ttacagcagg tgcaagacag     300
caagaagggg agagcagact aaatctggtt caacgtaatg tcaacatctt caagtttatc     360
atcccgaacg tagtaaaata cagtccagac tgcatgttgc ttgttgtgag taatccagtt     420
gacatcttaa cctatgttgc gtggaaaatc agtgggtttc caaaacatag ggtgattggc     480
tcaggatgca accttgatag cgccaggttt aggtatctaa tgggagaaaa attaggtatt     540
cactccttat cttgtcatgg ctggataata ggcgaacatg gtgattcttc ggtacctgtt     600
tggtccgggg ttaatgtggc tggtgttagt ttaaaagcat tatatcctga cctgggtact     660
gatgccgata agaacattg gaagaagtg cacaaacaag tggttgattc tgcttacgaa       720
gttattaaac ttaagggcta cacttcttgg gctataggtc tatcagtagc tgatttggca     780
gaaaccgtta tgaaaaattt aagaagagtc cacccaattt ccacgatggt caagggtatg     840
tacggtgtta gctctgacgt cttcttatct gttccttgtg ttttgggata tgcgggaatt     900
acagacgtcg tgaagatgac attgaaatca gaggaagagg aaaaactaag aaagtcagcc     960
gatactctgt ggggcattca aaaggaattg cagtttttaa                          999
```

<210> SEQ ID NO 15
<211> LENGTH: 563
<212> TYPE: PRT
<213> ORGANISM: Saccharomyces cerevisiae

<400> SEQUENCE: 15

```
Met Ser Glu Ile Thr Leu Gly Lys Tyr Leu Phe Glu Arg Leu Lys Gln
  1               5                  10                  15

Val Asn Val Asn Thr Val Phe Gly Leu Pro Gly Asp Phe Asn Leu Ser
                 20                  25                  30

Leu Leu Asp Lys Ile Tyr Glu Val Glu Gly Met Arg Trp Ala Gly Asn
             35                  40                  45

Ala Asn Glu Leu Asn Ala Ala Tyr Ala Ala Asp Gly Tyr Ala Arg Ile
         50                  55                  60

Lys Gly Met Ser Cys Ile Ile Thr Thr Phe Gly Val Gly Glu Leu Ser
 65                  70                  75                  80

Ala Leu Asn Gly Ile Ala Gly Ser Tyr Ala Glu His Val Gly Val Leu
                 85                  90                  95

His Val Val Gly Val Pro Ser Ile Ser Ser Gln Ala Lys Gln Leu Leu
                100                 105                 110

Leu His His Thr Leu Gly Asn Gly Asp Phe Thr Val Phe His Arg Met
            115                 120                 125

Ser Ala Asn Ile Ser Glu Thr Thr Ala Met Ile Thr Asp Ile Ala Thr
        130                 135                 140
```

```
Ala Pro Ala Glu Ile Asp Arg Cys Ile Arg Thr Thr Tyr Val Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Gln Thr Pro Ile Asp Met Ser Leu Lys Pro Asn
            180                 185                 190

Asp Ala Glu Ser Glu Lys Glu Val Ile Asp Thr Ile Leu Ala Leu Val
        195                 200                 205

Lys Asp Ala Lys Asn Pro Val Ile Leu Ala Asp Ala Cys Cys Ser Arg
210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Gln His
                245                 250                 255

Pro Arg Tyr Gly Gly Val Tyr Val Gly Thr Leu Ser Lys Pro Glu Val
            260                 265                 270

Lys Glu Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Asn
                325                 330                 335

Ile Ala Asp Ala Ala Lys Gly Tyr Lys Pro Val Ala Val Pro Ala Arg
            340                 345                 350

Thr Pro Ala Asn Ala Ala Val Pro Ala Ser Thr Pro Leu Lys Gln Glu
        355                 360                 365

Trp Met Trp Asn Gln Leu Gly Asn Phe Leu Gln Glu Gly Asp Val Val
370                 375                 380

Ile Ala Glu Thr Gly Thr Ser Ala Phe Gly Ile Asn Gln Thr Thr Phe
385                 390                 395                 400

Pro Asn Asn Thr Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
            420                 425                 430

Asp Pro Lys Lys Arg Val Ile Leu Phe Ile Gly Asp Gly Ser Leu Gln
        435                 440                 445

Leu Thr Val Gln Glu Ile Ser Thr Met Ile Arg Trp Gly Leu Lys Pro
450                 455                 460

Tyr Leu Phe Val Leu Asn Asn Asp Gly Tyr Thr Ile Glu Lys Leu Ile
465                 470                 475                 480

His Gly Pro Lys Ala Gln Tyr Asn Glu Ile Gln Gly Trp Asp His Leu
                485                 490                 495

Ser Leu Leu Pro Thr Phe Gly Ala Lys Asp Tyr Glu Thr His Arg Val
            500                 505                 510

Ala Thr Thr Gly Glu Trp Asp Lys Leu Thr Gln Asp Lys Ser Phe Asn
        515                 520                 525

Asp Asn Ser Lys Ile Arg Met Ile Glu Val Met Leu Pro Val Phe Asp
530                 535                 540

Ala Pro Gln Asn Leu Val Glu Gln Ala Lys Leu Thr Ala Ala Thr Asn
545                 550                 555                 560

Ala Lys Gln
```

<210> SEQ ID NO 16
<211> LENGTH: 1692
<212> TYPE: DNA
<213> ORGANISM: Saccharomyces cerevisiae

<400> SEQUENCE: 16

```
atgtctgaaa ttactttggg taaatatttg ttcgaaagat taaagcaagt caacgttaac      60
accgttttcg gtttgccagg tgacttcaac ttgtccttgt tggacaagat ctacgaagtt     120
gaaggtatga gatgggctgg taacgccaac gaattgaacg ctgcttacgc cgctgatggt     180
tacgctcgta tcaagggtat gtcttgtatc atcaccacct tcggtgtcgg tgaattgtct     240
gctttgaacg gtattgccgg ttcttacgct gaacacgtcg gtgttttgca cgttgttggt     300
gtcccatcca tctcttctca agctaagcaa ttgttgttgc accacacctt gggtaacggt     360
gacttcactg ttttccacag aatgtctgcc aacatttctg aaaccactgc tatgatcact     420
gacattgcta ccgccccagc tgaaattgac agatgtatca gaaccactta cgtcacccaa     480
agaccagtct acttaggttt gccagctaac ttggtcgact gaacgtccc agctaagttg     540
ttgcaaactc caattgacat gtctttgaag ccaaacgatg ctgaatccga aaaggaagtc     600
attgacacca tcttggcttt ggtcaaggat gctaagaacc cagttatctt ggctgatgct     660
tgttgttcca gacacgacgt caaggctgaa actaagaagt tgattgactt gactcaattc     720
ccagctttcg tcaccccaat gggtaagggt tccattgacg aacaacaccc aagatacggt     780
ggtgtttacg tcggtacctt gtccaagcca gaagttaagg aagccgttga atctgctgac     840
ttgattttgt ctgtcggtgc tttgttgtct gatttcaaca ccggttcttt ctcttactct     900
tacaagacca gaacattgt cgaattccac tccgaccaca tgaagatcag aaacgccact     960
ttcccaggtg tccaaatgaa attcgttttg caaaagttgt tgaccaatat tgctgacgcc    1020
gctaagggtt acaagccagt tgctgtccca gctagaactc cagctaacgc tgctgtccca    1080
gcttctaccc cattgaagca agaatggatg tggaaccaat tgggtaactt cttgcaagaa    1140
ggtgatgttg tcattgctga accggtacc tccgctttcg gtatcaacca aaccactttc    1200
ccaaacaaca cctacggtat ctctcaagtc ttatggggtt ccattggttt caccactggt    1260
gctaccttgg gtgctgcttt cgctgctgaa gaaattgatc aaagaagag agttatctta    1320
ttcattggtg acggttcttt gcaattgact gttcaagaaa tctccaccat gatcagatgg    1380
ggcttgaagc catacttgtt cgtcttgaac aacgatggtt acaccattga aaagttgatt    1440
cacggtccaa aggctcaata caacgaaatt caaggttggg accacctatc cttgttgcca    1500
actttcggtg ctaaggacta cgaaacccac agagtcgcta ccaccggtga atgggacaag    1560
ttgacccaag acaagtcttt caacgacaac tctaagatca gaatgattga ggttatgttg    1620
ccagtcttcg atgctccaca aaacttggtt gaacaagcta agttgactgc tgctaccaac    1680
gctaagcaat aa                                                        1692
```

<210> SEQ ID NO 17
<211> LENGTH: 591
<212> TYPE: PRT
<213> ORGANISM: Saccharomyces cerevisiae

<400> SEQUENCE: 17

```
Met Leu Lys Tyr Lys Pro Leu Leu Lys Ile Ser Lys Asn Cys Glu Ala
 1               5                  10                  15

Ala Ile Leu Arg Ala Ser Lys Thr Arg Leu Asn Thr Ile Arg Ala Tyr
```

```
                    20                  25                  30
Gly Ser Thr Val Pro Lys Ser Lys Ser Phe Glu Gln Asp Ser Arg Lys
                35                  40                  45
Arg Thr Gln Ser Trp Thr Ala Leu Arg Val Gly Ala Ile Leu Ala Ala
 50                  55                  60
Thr Ser Ser Val Ala Tyr Leu Asn Trp His Asn Gly Gln Ile Asp Asn
 65                  70                  75                  80
Glu Pro Lys Leu Asp Met Asn Lys Gln Lys Ile Ser Pro Ala Glu Val
                 85                  90                  95
Ala Lys His Asn Lys Pro Asp Asp Cys Trp Val Val Ile Asn Gly Tyr
                100                 105                 110
Val Tyr Asp Leu Thr Arg Phe Leu Pro Asn His Pro Gly Gly Gln Asp
                115                 120                 125
Val Ile Lys Phe Asn Ala Gly Lys Asp Val Thr Ala Ile Phe Glu Pro
                130                 135                 140
Leu His Ala Pro Asn Val Ile Asp Lys Tyr Ile Ala Pro Glu Lys Lys
145                 150                 155                 160
Leu Gly Pro Leu Gln Gly Ser Met Pro Pro Glu Leu Val Cys Pro Pro
                165                 170                 175
Tyr Ala Pro Gly Glu Thr Lys Glu Asp Ile Ala Arg Lys Glu Gln Leu
                180                 185                 190
Lys Ser Leu Leu Pro Pro Leu Asp Asn Ile Ile Asn Leu Tyr Asp Phe
                195                 200                 205
Glu Tyr Leu Ala Ser Gln Thr Leu Thr Lys Gln Ala Trp Ala Tyr Tyr
                210                 215                 220
Ser Ser Gly Ala Asn Asp Glu Val Thr His Arg Glu Asn His Asn Ala
225                 230                 235                 240
Tyr His Arg Ile Phe Phe Lys Pro Lys Ile Leu Val Asp Val Arg Lys
                245                 250                 255
Val Asp Ile Ser Thr Asp Met Leu Gly Ser His Val Asp Val Pro Phe
                260                 265                 270
Tyr Val Ser Ala Thr Ala Leu Cys Lys Leu Gly Asn Pro Leu Glu Gly
                275                 280                 285
Glu Lys Asp Val Ala Arg Gly Cys Gly Gln Gly Val Thr Lys Val Pro
                290                 295                 300
Gln Met Ile Ser Thr Leu Ala Ser Cys Ser Pro Glu Glu Ile Ile Glu
305                 310                 315                 320
Ala Ala Pro Ser Asp Lys Gln Ile Gln Trp Tyr Gln Leu Tyr Val Asn
                325                 330                 335
Ser Asp Arg Lys Ile Thr Asp Asp Leu Val Lys Asn Val Glu Lys Leu
                340                 345                 350
Gly Val Lys Ala Leu Phe Val Thr Val Asp Ala Pro Ser Leu Gly Gln
                355                 360                 365
Arg Glu Lys Asp Met Lys Leu Lys Phe Ser Asn Thr Lys Ala Gly Pro
                370                 375                 380
Lys Ala Met Lys Lys Thr Asn Val Glu Glu Ser Gln Gly Ala Ser Arg
385                 390                 395                 400
Ala Leu Ser Lys Phe Ile Asp Pro Ser Leu Thr Trp Lys Asp Ile Glu
                405                 410                 415
Glu Leu Lys Lys Lys Thr Lys Leu Pro Ile Val Ile Lys Gly Val Gln
                420                 425                 430
Arg Thr Glu Asp Val Ile Lys Ala Ala Glu Ile Gly Val Ser Gly Val
                435                 440                 445
```

```
Val Leu Ser Asn His Gly Gly Arg Gln Leu Asp Phe Ser Arg Ala Pro
    450                 455                 460

Ile Glu Val Leu Ala Glu Thr Met Pro Ile Leu Glu Gln Arg Asn Leu
465                 470                 475                 480

Lys Asp Lys Leu Glu Val Phe Val Asp Gly Gly Val Arg Arg Gly Thr
                485                 490                 495

Asp Val Leu Lys Ala Leu Cys Leu Gly Ala Lys Gly Val Gly Leu Gly
            500                 505                 510

Arg Pro Phe Leu Tyr Ala Asn Ser Cys Tyr Gly Arg Asn Gly Val Glu
        515                 520                 525

Lys Ala Ile Glu Ile Leu Arg Asp Glu Ile Glu Met Ser Met Arg Leu
    530                 535                 540

Leu Gly Val Thr Ser Ile Ala Glu Leu Lys Pro Asp Leu Leu Asp Leu
545                 550                 555                 560

Ser Thr Leu Lys Ala Arg Thr Val Gly Val Pro Asn Asp Val Leu Tyr
                565                 570                 575

Asn Glu Val Tyr Glu Gly Pro Thr Leu Thr Glu Phe Glu Asp Ala
            580                 585                 590

<210> SEQ ID NO 18
<211> LENGTH: 1776
<212> TYPE: DNA
<213> ORGANISM: Saccharomyces cerevisiae

<400> SEQUENCE: 18
atgctaaaat acaaaccttt actaaaaatc tcgaagaact gtgaggctgc tatcctcaga      60
gcgtctaaga ctagattgaa cacaatccgc gcgtacggtt ctaccgttcc aaaatccaag     120
tcgttcgaac aagactcaag aaaacgcaca cagtcatgga ctgccttgag agtcggtgca     180
attctagccg ctactagttc cgtggcgtat ctaaactggc ataatggcca aatagacaac     240
gagccgaaac tggatatgaa taaacaaaag atttcgcccg ctgaagttgc caagcataac     300
aagcccgatg attgttgggt tgtgatcaat ggttacgtat acgacttaac gcgattccta     360
ccaaatcatc caggtgggca ggatgttatc aagtttaacg ccgggaaaga tgtcactgct     420
atttttgaac cactacatgc tcctaatgtc atcgataagt atatagctcc cgagaaaaaa     480
ttgggtcccc ttcaaggatc catgcctcct gaacttgtct gtcctcctta tgctcctggt     540
gaaactaagg aagatatcgc tagaaaagaa caactaaaat cgctgctacc tcctctagat     600
aatattatta acctttacga ctttgaatac ttggcctctc aaactttgac taaacaagcg     660
tgggcctact attcctccgg tgctaacgac gaagttactc acagagaaaa ccataatgct     720
tatcatagga tttttttcaa accaaagatc cttgtagatg tacgcaaagt agacatttca     780
actgacatgt tgggttctca tgtggatgtt cccttctacg tgtctgctac agctttgtgt     840
aaactgggaa acccccttaga aggtgaaaaa gatgtcgcca gaggttgtgg ccaaggtgtg     900
acaaaagtcc cacaaatgat atctactttg gcttcatgtt cccctgagga aattattgaa     960
gcagcaccct ctgataaaca aattcaatgg taccaactat atgttaactc tgatagaaag    1020
atcactgatg atttggttaa aaatgtagaa aagctgggtg taaaggcatt atttgtcact    1080
gtggatgctc caagtttagg tcaaagagaa aaagatatga agctgaaatt ttccaataca    1140
aaggctggtc caaaagcgat gaagaaaact aatgtagaag aatctcaagg tgcttcgaga    1200
gcgttatcaa agtttattga cccctctttg acttggaaag atatagaaga gttgaagaaa    1260
aagacaaaac tacctattgt tatcaaaggt gttcaacgta ccgaagatgt tatcaaagca    1320
```

```
gcagaaatcg gtgtaagtgg ggtggttcta tccaatcatg gtggtagaca attagatttt    1380
tcaagggctc ccattgaagt cctggctgaa accatgccaa tcctggaaca acgtaacttg    1440
aaggataagt tggaagtttt cgtggacggt ggtgttcgtc gtggtacaga tgtcttgaaa    1500
gcgttatgtc taggtgctaa aggtgttggt ttgggtagac cattcttgta tgcgaactca    1560
tgctatggtc gtaatggtgt tgaaaaagcc attgaaattt aagagatga aattgaaatg    1620 tctatgagac tattaggtgt tactagcatt gcggaattga agcctgatct tttagatcta    1680
tcaacactaa aggcaagaac agttggagta ccaaacgacg tgctgtataa tgaagtttat    1740
gagggaccta ctttaacaga atttgaggat gcatga                              1776
```

<210> SEQ ID NO 19
<211> LENGTH: 391
<212> TYPE: PRT
<213> ORGANISM: Saccharomyces cerevisiae

<400> SEQUENCE: 19

```
Met Ser Ala Ala Asp Arg Leu Asn Leu Thr Ser Gly His Leu Asn
  1               5                  10                  15

Ala Gly Arg Lys Arg Ser Ser Ser Val Ser Leu Lys Ala Ala Glu
                 20                  25                  30

Lys Pro Phe Lys Val Thr Val Ile Gly Ser Gly Asn Trp Gly Thr Thr
             35                  40                  45

Ile Ala Lys Val Val Ala Glu Asn Cys Lys Gly Tyr Pro Glu Val Phe
 50                  55                  60

Ala Pro Ile Val Gln Met Trp Val Phe Glu Glu Ile Asn Gly Glu
 65                  70                  75                  80

Lys Leu Thr Glu Ile Ile Asn Thr Arg His Gln Asn Val Lys Tyr Leu
                 85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285
```

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390

<210> SEQ ID NO 20
<211> LENGTH: 1176
<212> TYPE: DNA
<213> ORGANISM: Saccharomyces cerevisiae

<400> SEQUENCE: 20
atgtctgctg ctgctgatag attaaactta acttccggcc acttgaatgc tggtagaaag      60
agaagttcct cttctgtttc tttgaaggct gccgaaaagc ctttcaaggt tactgtgatt     120
ggatctggta actggggtac tactattgcc aaggtggttg ccgaaaattg taagggatac     180
ccagaagttt tcgctccaat agtacaaatg tgggtgttcg aagaagagat caatggtgaa     240
aaattgactg aaatcataaa tactagacat caaaacgtga atacttgcc tggcatcact      300
ctacccgaca atttggttgc taatccagac ttgattgatt cagtcaagga tgtcgacatc     360
atcgttttca acattccaca tcaattttg ccccgtatct gtagccaatt gaaaggtcat      420
gttgattcac acgtcagagc tatctcctgt ctaaagggtt ttgaagttgg tgctaaaggt     480
gtccaattgc tatcctctta catcactgag gaactaggta ttcaatgtgg tgctctatct     540
ggtgctaaca ttgccaccga agtcgctcaa gaacactggt ctgaaacaac agttgcttac     600
cacattccaa aggatttcag aggcgagggc aaggacgtcg accataaggt tctaaaggcc     660
ttgttccaca gaccttactt ccacgttagt gtcatcgaag atgttgctgg tatctccatc     720
tgtggtgctt tgaagaacgt tgttgcctta ggttgtggtt tcgtcgaagg tctaggctgg     780
ggtaacaacg cttctgctgc catccaaaga gtcggtttgg gtgagatcat cagattcggt     840
caaatgtttt tcccagaatc tagagaagaa acatactacc aagagtctgc tggtgttgct     900
gatttgatca ccacctgcgc tggtggtaga aacgtcaagg ttgctaggct aatggctact     960
tctggtaagg acgcctggga atgtgaaaag gagttgttga atggccaatc cgctcaaggt    1020
ttaattacct gcaaagaagt tcacgaatgg ttggaaacat gtggtctctgt cgaagacttc    1080
ccattatttg aagccgtata ccaaatcgtt acaacaact acccaatgaa gaacctgccg     1140
gacatgattg aagaattaga tctacatgaa gattag                              1176

<210> SEQ ID NO 21
<211> LENGTH: 560
<212> TYPE: PRT
<213> ORGANISM: Saccharomyces cerevisiae

<400> SEQUENCE: 21

Met Ile Arg Gln Ser Leu Met Lys Thr Val Trp Ala Asn Ser Ser Arg
1               5                   10                  15

-continued

```
Phe Ser Leu Gln Ser Lys Ser Gly Leu Val Lys Tyr Ala Lys Asn Arg
             20                  25                  30
Ser Phe His Ala Ala Arg Asn Leu Leu Glu Asp Lys Lys Val Ile Leu
         35                  40                  45
Gln Lys Val Ala Pro Thr Thr Gly Val Val Ala Lys Gln Ser Phe Phe
     50                  55                  60
Lys Arg Thr Gly Lys Phe Thr Leu Lys Ala Leu Leu Tyr Ser Ala Leu
 65                  70                  75                  80
Ala Gly Thr Ala Tyr Val Ser Tyr Ser Leu Tyr Arg Glu Ala Asn Pro
                 85                  90                  95
Ser Thr Gln Val Pro Gln Ser Asp Thr Phe Pro Asn Gly Ser Lys Arg
            100                 105                 110
Lys Thr Leu Val Ile Leu Gly Ser Gly Trp Gly Ser Val Ser Leu Leu
        115                 120                 125
Lys Asn Leu Asp Thr Thr Leu Tyr Asn Val Val Val Ser Pro Arg
130                 135                 140
Asn Tyr Phe Leu Phe Thr Pro Leu Leu Pro Ser Thr Pro Val Gly Thr
145                 150                 155                 160
Ile Glu Leu Lys Ser Ile Val Glu Pro Val Arg Thr Ile Ala Arg Arg
                165                 170                 175
Ser His Gly Glu Val His Tyr Tyr Glu Ala Glu Ala Tyr Asp Val Asp
            180                 185                 190
Pro Glu Asn Lys Thr Ile Lys Val Lys Ser Ser Ala Lys Asn Asn Asp
        195                 200                 205
Tyr Asp Leu Asp Leu Lys Tyr Asp Tyr Leu Val Gly Val Gly Ala
210                 215                 220
Gln Pro Asn Thr Phe Gly Thr Pro Gly Val Tyr Glu Tyr Ser Ser Phe
225                 230                 235                 240
Leu Lys Glu Ile Ser Asp Ala Gln Glu Ile Arg Leu Lys Ile Met Ser
                245                 250                 255
Ser Ile Glu Lys Ala Ala Ser Leu Ser Pro Lys Asp Pro Glu Arg Ala
            260                 265                 270
Arg Leu Leu Ser Phe Val Val Gly Gly Pro Thr Gly Val Glu
        275                 280                 285
Phe Ala Ala Glu Leu Arg Asp Tyr Val Asp Gln Asp Leu Arg Lys Trp
    290                 295                 300
Met Pro Glu Leu Ser Lys Glu Ile Lys Val Thr Leu Val Glu Ala Leu
305                 310                 315                 320
Pro Asn Ile Leu Asn Met Phe Asp Lys Tyr Leu Val Asp Tyr Ala Gln
                325                 330                 335
Asp Leu Phe Lys Glu Glu Lys Ile Asp Leu Arg Leu Lys Thr Met Val
            340                 345                 350
Lys Lys Val Asp Ala Thr Thr Ile Thr Ala Lys Thr Gly Asp Gly Asp
        355                 360                 365
Ile Glu Asn Ile Pro Tyr Gly Val Leu Val Trp Ala Thr Gly Asn Ala
    370                 375                 380
Pro Arg Glu Val Ser Lys Asn Leu Met Thr Lys Leu Glu Glu Gln Asp
385                 390                 395                 400
Ser Arg Arg Gly Leu Leu Ile Asp Asn Lys Leu Gln Leu Leu Gly Ala
                405                 410                 415
Lys Gly Ser Ile Phe Ala Ile Gly Asp Cys Thr Phe His Pro Gly Leu
            420                 425                 430
```

```
Phe Pro Thr Ala Gln Val Ala His Gln Glu Gly Glu Tyr Leu Ala Gln
            435                 440                 445

Tyr Phe Lys Lys Ala Tyr Lys Ile Asp Gln Leu Asn Trp Lys Met Thr
450                 455                 460

His Ala Lys Asp Asp Ser Glu Val Ala Arg Leu Lys Asn Gln Ile Val
465                 470                 475                 480

Lys Thr Gln Ser Gln Ile Glu Asp Phe Lys Tyr Asn His Lys Gly Ala
                485                 490                 495

Leu Ala Tyr Ile Gly Ser Asp Lys Ala Ile Ala Asp Leu Ala Val Gly
            500                 505                 510

Glu Ala Lys Tyr Arg Leu Ala Gly Ser Phe Thr Phe Leu Phe Trp Lys
        515                 520                 525

Ser Ala Tyr Leu Ala Met Cys Leu Ser Phe Arg Asn Arg Val Leu Val
    530                 535                 540

Ala Met Asp Trp Ala Lys Val Tyr Phe Leu Gly Arg Asp Ser Ser Ile
545                 550                 555                 560

<210> SEQ ID NO 22
<211> LENGTH: 545
<212> TYPE: PRT
<213> ORGANISM: Saccharomyces cerevisiae

<400> SEQUENCE: 22

Met Leu Pro Arg Leu Gly Phe Ala Arg Thr Ala Arg Ser Ile His Arg
1               5                   10                  15

Phe Lys Met Thr Gln Ile Ser Lys Pro Phe His Ser Thr Glu Val
            20                  25                  30

Gly Lys Pro Gly Pro Gln Gln Lys Leu Ser Lys Ser Tyr Thr Ala Val
            35                  40                  45

Phe Lys Lys Trp Phe Val Arg Gly Leu Lys Leu Thr Phe Tyr Thr Thr
        50                  55                  60

Leu Ala Gly Thr Leu Tyr Val Ser Tyr Glu Leu Tyr Lys Glu Ser Asn
65                  70                  75                  80

Pro Pro Lys Gln Val Pro Gln Ser Thr Ala Phe Ala Asn Gly Leu Lys
                85                  90                  95

Lys Lys Glu Leu Val Ile Leu Gly Thr Gly Trp Gly Ala Ile Ser Leu
            100                 105                 110

Leu Lys Lys Leu Asp Thr Ser Leu Tyr Asn Val Thr Val Val Ser Pro
        115                 120                 125

Arg Ser Phe Phe Leu Phe Thr Pro Leu Leu Pro Ser Thr Pro Val Gly
    130                 135                 140

Thr Ile Glu Met Lys Ser Ile Val Glu Pro Val Arg Ser Ile Ala Arg
145                 150                 155                 160

Arg Thr Pro Gly Glu Val His Tyr Ile Glu Ala Glu Ala Leu Asp Val
                165                 170                 175

Asp Pro Lys Ala Lys Lys Val Met Val Gln Ser Val Ser Glu Asp Glu
            180                 185                 190

Tyr Phe Val Ser Ser Leu Ser Tyr Asp Tyr Leu Val Val Ser Val Gly
        195                 200                 205

Ala Lys Thr Thr Thr Phe Asn Ile Pro Gly Val Tyr Gly Asn Ala Asn
    210                 215                 220

Phe Leu Lys Glu Ile Glu Asp Ala Gln Asn Ile Arg Met Lys Leu Met
225                 230                 235                 240

Lys Thr Ile Glu Gln Ala Ser Ser Phe Pro Val Asn Asp Pro Glu Arg
                245                 250                 255
```

```
Lys Arg Leu Leu Thr Phe Val Val Gly Gly Pro Thr Gly Val
            260                 265                 270
Glu Phe Ala Ala Glu Leu Gln Asp Tyr Ile Asn Gln Leu Arg Lys
            275                 280                 285
Trp Met Pro Asp Leu Ser Lys Glu Met Lys Val Ile Leu Ile Glu Ala
    290                 295                 300
Leu Pro Asn Ile Leu Asn Met Phe Asp Lys Thr Leu Ile Lys Tyr Ala
305                 310                 315                 320
Glu Asp Leu Phe Ala Arg Asp Glu Ile Asp Leu Gln Val Asn Thr Ala
                325                 330                 335
Val Lys Val Val Glu Pro Thr Tyr Ile Arg Thr Leu Gln Asn Gly Gln
            340                 345                 350
Thr Asn Thr Asp Ile Glu Tyr Gly Met Leu Val Trp Ala Thr Gly Asn
            355                 360                 365
Glu Pro Ile Asp Phe Ser Lys Thr Leu Met Ser Arg Ile Pro Glu Gln
            370                 375                 380
Thr Asn Arg Arg Gly Leu Leu Ile Asn Asp Lys Leu Glu Leu Leu Gly
385                 390                 395                 400
Ser Glu Asn Ser Ile Tyr Ala Ile Gly Asp Cys Thr Ala His Thr Gly
                405                 410                 415
Phe Phe Pro Thr Ala Gln Val Ala His Gln Glu Gly Glu Tyr Leu Ala
            420                 425                 430
Lys Ile Leu Asp Lys Lys Leu Gln Ile Glu Gln Leu Glu Trp Asp Met
            435                 440                 445
Leu Asn Ser Thr Asp Glu Thr Glu Val Ser Arg Leu Gln Lys Glu Val
            450                 455                 460
Asn Leu Arg Lys Ser Lys Leu Asp Lys Phe Asn Tyr Lys His Met Gly
465                 470                 475                 480
Ala Leu Ala Tyr Ile Gly Ser Glu Thr Ala Ile Ala Asp Leu His Met
                485                 490                 495
Gly Asp Ser Ser Tyr Gln Leu Lys Gly Met Phe Ala Phe Leu Phe Trp
            500                 505                 510
Lys Ser Ala Tyr Leu Ala Met Cys Leu Ser Ile Arg Asn Arg Ile Leu
            515                 520                 525
Ile Ala Met Asp Trp Thr Lys Val Tyr Phe Leu Gly Arg Asp Ser Ser
        530                 535                 540
Val
545

<210> SEQ ID NO 23
<211> LENGTH: 1683
<212> TYPE: DNA
<213> ORGANISM: Saccharomyces cerevisiae

<400> SEQUENCE: 23
atgattagac aatcattaat gaaaacagtg tgggctaact cctccaggtt tagcctacag      60
agcaagtcgg ggcttgtgaa atatgccaaa atagatcgt tccatgcagc aagaaatttg     120
ctagaggaca agaaagtcat tttgcaaaaa gtggcgccca ctactggcgt tgttgcgaag     180
cagtcctttt tcaagagaac tgggaaattt actttgaagg ctttattgta ttctgccctc     240
gcgggtacgg cttacgtttc atactcactt taccgagaag ctaacccttc tacccaagtt     300
cctcaatcgg acacttttcc aaacggttca agaggaaga ctttggtaat tctgggctcc     360
ggttggggtt ctgtgtcgct tttgaaaaat ttggacacca cgttgtataa tgttgttgtt     420
```

```
gtttctccaa gaaattattt tcttttact  ccgctattgc catctacccc agttggtacc   480
atcgaattga aatctattgt tgaacctgtc aggactattg ctagaagatc gcacggtgaa   540
gtccattact atgaagctga agcgtacgac gttgatcctg aaaacaaaac aattaaggtc   600
aaatcttccg ctaagaataa cgactacgac ttggacttga aatacgacta tctggttgtc   660
ggtgtgggtg ctcaaccaaa cacttttggt actccgggag tttatgaata ttcttctttc   720
ttgaaggaaa tatccgacgc tcaagagatc agattaaaaa ttatgtccag tattgagaaa   780
gctgcctccc tatctccaaa agatcctgag agagcaagat tgttgagctt tgttgtcgtt   840
ggtggtggtc ccaccggtgt cgaatttgcc gctgaattga gagattatgt tgaccaggac   900
ttgagaaaat ggatgcccga attgagtaaa gaaattaaag tcactttggt ggaggctttg   960
ccaaacattt tgaacatgtt tgacaagtat ctcgttgact atgctcaaga tttattcaaa   1020
gaggaaaaaa tcgatttaag attgaaaaca atggttaaga agttgacgc  taccactata   1080 actgccaaaa ctggcgatgg tgacattgaa aatataccgt atggtgtatt agtttgggct   1140
acaggtaatg cgccaagaga agtgtctaag aacctaatga ctaaattaga ggaacaggac   1200
tcaagacgtg gtttgttgat agataacaaa cttcaacttt tgggtgctaa gggatctatt   1260
tttgctatcg gcgattgtac cttccaccct ggcttgttcc ctaccgctca agttgcccac   1320
caagaaggtg aatacttggc tcagtatttc aagaaagctt ataaaatcga tcaattgaac   1380
tggaaaatga cccatgctaa agacgattca gaagtcgcta gattaaagaa ccaaatagtc   1440
aaaacgcaat cgcaaattga agacttcaag tacaaccata agggtgctct ggcttatatt   1500
ggttcagata aagccattgc tgatcttgcc gttggtgaag ccaaatatag gttagccggc   1560
tcattcacct tcctattctg gaaatctgct tatttggcaa tgtgtctatc ctttagaaac   1620
agagttcttg tcgctatgga ttgggctaaa gtttatttct gggtagaga  ttcatctatc   1680 tag                                                                 1683

<210> SEQ ID NO 24
<211> LENGTH: 1638
<212> TYPE: DNA
<213> ORGANISM: Saccharomyces cerevisiae

<400> SEQUENCE: 24
atgctgccca gacttggttt tgcgaggact gctaggtcca tacaccgttt caagatgacc    60
cagatctcta aaccttttt  ccattccact gaagttggta agcccggacc acagcagaag   120
ctatcgaaat cttacactgc ggtattcaag aaatggtttg tcagaggttt aaagttaacc   180
ttttacacga cgttggccgg cacattgtat gtgtcatacg agctgtacaa agaatcgaac   240
ccacccaaac aggttcccca atcgaccgct tttgctaatg gtttgaaaaa gaaggagctg   300
gttattttgg gtacaggctg gggcgccata tctcttttga gaaattaga cacgtctttg   360 tataacgtga ccgtggtgtc gccaagaagc ttctttttgt tcacaccgtt attaccctca   420
acgcctgtgg gtacgataga gatgaagtct attgtcgaac cggttagatc gatcgctaga   480
agaacgcctg agaagttca  ctacattgag gcggaagcgt tggacgttga tccaaaggcc   540
aaaaaagtaa tggtgcaatc ggtgtcagag gacgaatatt tcgtttcgag cttaagttac   600
gattatcttg ttgttagtgt aggcgctaaa accactactt ttaacattcc cggggtctat   660
ggcaatgcta acttcttgaa agagattgaa gatgctcaaa atattcgtat gaagttaatg   720
aaaaccatag aacaggcaag ttcatttcct gtgaacgatc cggaaaggaa gcgattatta   780
```

```
acgttcgtgg ttgttggagg gggccctacg ggggttgaat ttgccgccga actgcaagat    840
tacatcaatc aagatttgag gaagtggatg cccgacttaa gtaaagaaat gaaggttatc    900
ttaattgaag ccctgcctaa tatcctaaac atgttcgata agacgttgat caagtatgcc    960
gaggaccttt tgccagaga tgaaattgac ttgcaagtga atactgccgt gaaagtcgta   1020
gagccaacct atatacgcac tctgcaaaac ggccaaacaa acacgatat cgaatacggg   1080 atgctggttt gggccacggg aaatgaacca atcgattttt caaagacact gatgagtaga   1140
ataccggagc aaactaatag gcgtggtctg ttaattaatg acaagttgga gcttctcggt   1200
tctgagaatt cgatttatgc aattggtgat tgtaccgcac acgggttt ctttcccacg    1260 gcacaagttg cacatcagga aggcgaatac ttggccaaga tcttggataa aaaattacag   1320
atagaacaat tggaatggga catgctcaac agtaccgatg aaactgaggt atcacgtcta   1380 caaaagagg ttaatttgag gaaatctaag ttggataagt tcaactacaa gcatatgggt    1440
gcccttgcgt acatcggctc tgaaaccgca attgcagatt tgcatatggg cgactcatca   1500
taccagttga aaggtatgtt tgccttcttg ttttggaaat ccgcttattt ggccatgtgt   1560
ctctctatca ggaataggat tttaattgcc atggactgga ccaaagttta ctttcttgga   1620
agggattcct ccgtgtag                                                1638

<210> SEQ ID NO 25
<211> LENGTH: 31
<212> TYPE: DNA
<213> ORGANISM: Artificial Sequence
<220> FEATURE:
<223> OTHER INFORMATION: Synthetic forward primer

<400> SEQUENCE: 25
cgagctcttc gcggccacct acgccgctat c                                  31

<210> SEQ ID NO 26
<211> LENGTH: 32
<212> TYPE: DNA
<213> ORGANISM: Artificial Sequence
<220> FEATURE:
<223> OTHER INFORMATION: Synthetic reverse primer

<400> SEQUENCE: 26
gctctagata ttgatatagt gtttaagcga at                                 32

<210> SEQ ID NO 27
<211> LENGTH: 26
<212> TYPE: DNA
<213> ORGANISM: Artificial Sequence
<220> FEATURE:
<223> OTHER INFORMATION: Synthetic forward primer

<400> SEQUENCE: 27
ggatccatgt ccgtaaagga actact                                        26

<210> SEQ ID NO 28
<211> LENGTH: 34
<212> TYPE: DNA
<213> ORGANISM: Artificial Sequence
<220> FEATURE:
<223> OTHER INFORMATION: Synthetic reverse primer

<400> SEQUENCE: 28
acgcgtcgac ttaaaactgc aattccttt gaat                                34
```

<210> SEQ ID NO 29
<211> LENGTH: 1267
<212> TYPE: DNA
<213> ORGANISM: Artificial Sequence
<220> FEATURE:
<223> OTHER INFORMATION: Synthetic ARS/CEN

<400> SEQUENCE: 29

```
gagctccttt catttctgat aaaagtaaga ttactccatt tatcttttca ccaacatatt    60
catagttgaa agttatcctt ctaagtacgt atacaatatt aattaaacgt aaaaacaaaa   120
ctgactgtaa aaatgtgtaa aaaaaaaata tcaaattcat agcagtttca aggaatgaaa   180
actattatga tctggtcacg tgtatataaa ttattaattt taaacccata taatttatta   240
ttttttatt ctaaagttta aagtaatttt agtagtattt tatattttga ataaatatac    300
tttaaatttt tattttata ttttattact tttaaaaata atgttttat ttaaaacaaa     360
attataagtt aaaaagttgt tccgaaagta aaatatattt tatagttttt acaaaaataa   420
attattttta acgtattttt tttaattata tttttgtatg tgattatatc cacaggtatt   480
atgctgaatt tagctgtttc agtttaccag tgtgatagta tgattttttt tgcctctcaa   540
aagctatttt tttagaagct tcgtcttaga ataggtggt gtataaattg cggttgactt    600
ttaactatat atcattttcg atttatttat tacatagaga ggtgcttta attttttaat    660
ttttattttc aataatttta aaagtgggta cttttaaatt ggaacaaagt gaaaaatatc   720
tgttatacgt gcaactgaat tttactgacc ttaaaggact atctcaatcc tggttcagaa   780
atccttgaaa tgattgatat gttggtggat tttctctgat tttcaaacaa gaggtattt    840
atttcatatt tattatattt tttacattta ttttatattt ttttattgtt tggaagggaa   900
agcgacaatc aaattcaaaa tatattaatt aaactgtaat acttaataag agacaaataa   960
cagccaagaa tcaaatactg gttttttaat caaaagatct ctctacatgc acccaaattc  1020
attatttaaa tttactatac tacagacaga atatacgaac ccagattaag tagtcagacg  1080
cttttccgct ttattgagta tatagcctta catattttct gcccataatt tctggattta  1140
aaataaacaa aaatggttac tttgtagtta tgaaaaaagg cttttccaaa atgcgaaata  1200
cgtgttattt aaggttaatc aacaaaacgc atatccatat gggtagttgg acaaaacttc  1260
aatcgat                                                            1267
```

<210> SEQ ID NO 30
<211> LENGTH: 252
<212> TYPE: DNA
<213> ORGANISM: Artificial Sequence
<220> FEATURE:
<223> OTHER INFORMATION: Synthetic CYC1 terminator

<400> SEQUENCE: 30

```
tcatgtaatt agttatgtca cgcttacatt cacgccctcc ccccacatcc gctctaaccg    60
aaaaggaagg agttagacaa cctgaagtct aggtccctat ttatttttt atagttatgt    120
tagtattaag aacgttattt atatttcaaa tttttctttt ttttctgtac agacgcgtgt   180
acgcatgtaa cattatactg aaaaccttgc ttgagaaggt tttgggacgc tcgaaggctt   240
taatttgcgg cc                                                       252
```

<210> SEQ ID NO 31
<211> LENGTH: 289
<212> TYPE: DNA
<213> ORGANISM: Artificial Sequence
<220> FEATURE:

<223> OTHER INFORMATION: Synthetic CYC promoter

<400> SEQUENCE: 31

| | | |
|---|---|---|
| atttggcgag cgttggttgg tggatcaagc ccacgcgtag gcaatcctcg agcagatccg | 60 | |
| ccaggcgtgt atatatagcg tggatggcca ggcaacttta gtgctgacac atacaggcat | 120 | |
| atatatatgt gtgcgacgac acatgatcat atggcatgca tgtgctctgt atgtatataa | 180 | |
| aactcttgtt ttcttctttt ctctaaatat tctttcctta tacattagga cctttgcagc | 240 | |
| ataaattact atacttctat agacacgcaa acacaaatac acacactaa | 289 | |

<210> SEQ ID NO 32
<211> LENGTH: 655
<212> TYPE: DNA
<213> ORGANISM: Artificial Sequence
<220> FEATURE:
<223> OTHER INFORMATION: Synthetic GPD promoter

<400> SEQUENCE: 32

| | |
|---|---|
| agtttatcat tatcaatact cgccatttca agaatacgt aaataattaa tagtagtgat | 60 |
| tttcctaact ttatttagtc aaaaaattag ccttttaatt ctgctgtaac ccgtacatgc | 120 |
| ccaaaatagg gggcgggtta cacagaatat ataacatcg aggtgtctgg gtgaacagtt | 180 |
| tattcctggc atccactaaa tataatggag cccgcttttt aagctggcat ccagaaaaaa | 240 |
| aaagaatccc agcaccaaaa tattgttttc ttcaccaacc atcagttcat aggtccattc | 300 |
| tcttagcgca actacagaga acaggggcac aaacaggcaa aaacgggca caacctcaat | 360 |
| ggagtgatgc aacctgcctg gagtaaatga tgacacaagg caattgaccc acgcatgtat | 420 |
| ctatctcatt ttcttacacc ttctattacc ttctgctctc tctgatttgg aaaaagctga | 480 |
| aaaaaaaggt tgaaaccagt tccctgaaat tattccccta cttgactaat aagtatataa | 540 |
| agacggtagg tattgattgt aattctgtaa atctatttct taaacttctt aaattctact | 600 |
| tttatagtta gtctttttt tagttttaaa acaccagaac ttagtttcga cggat | 655 |

<210> SEQ ID NO 33
<211> LENGTH: 1468
<212> TYPE: DNA
<213> ORGANISM: Artificial Sequence
<220> FEATURE:
<223> OTHER INFORMATION: Synthetic ADH promoter

<400> SEQUENCE: 33

| | |
|---|---|
| gccgggatcg aagaaatgat ggtaaatgaa ataggaaatc aaggagcatg aaggcaaaag | 60 |
| acaaatataa gggtcgaacg aaaaataaag tgaaagtgt tgatatgatg tatttggctt | 120 |
| tgcggcgccg aaaaaacgag tttacgcaat tgcacaatca tgctgactct gtggcggacc | 180 |
| cgcgctcttg ccggcccggc gataacgctg ggcgtgaggc tgtgcccggc ggagtttttt | 240 |
| gcgcctgcat tttccaaggt ttaccctgcg ctaaggggcg agattggaga agcaataaga | 300 |
| atgccggttc ggggttgcgat gatgacgacc acgacaactg gtgtcattat ttaagttgcc | 360 |
| gaaagaacct gagtgcattt gcaacatgag tatactagaa gaatgagcca agacttgcga | 420 |
| gacgcgagtt tgccggtggt gcgaacaata gagcgaccat gaccttgaag gtgagacgcg | 480 |
| cataaccgct agagtacttt gaagaggaaa cagcaatagg gttgctacca gtataaatag | 540 |
| acaggtacat acaacactgg aaatggttgt ctgtttgagt acgctttcaa ttcatttggg | 600 |
| tgtgcacttt attatgttac aatatggaag ggaactttac acttctccta tgcacatata | 660 |
| ttaattaaag tccaatgcta gtagagaagg ggggtaacac ccctccgcgc tcttttccga | 720 |

```
tttttttcta aaccgtggaa tatttcggat atccttttgt tgtttccggg tgtacaatat      780
ggacttcctc ttttctggca accaaaccca tacatcggga ttcctataat accttcgttg      840
gtctccctaa catgtaggtg gcggaggga gatatacaat agaacagata ccagacaaga       900
```
(Note: "gcggaggga" should be "gcggagggga" based on spacing)
```
gtctccctaa catgtaggtg gcggagggga gatatacaat agaacagata ccagacaaga      900
cataatgggc taaacaagac tacaccaatt acactgcctc attgatggtg gtacataacg      960
aactaatact gtagccctag acttgatagc catcatcata tcgaagtttc actacccttt     1020
ttccatttgc catctattga agtaataata ggcgcatgca acttcttttc ttttttttc      1080 ttttctctct cccccgttgt tgtctcacca tatccgcaat gacaaaaaaa tgatggaaga     1140
cactaaagga aaaaattaac gacaaagaca gcaccaacag atgtcgttgt tccagagctg     1200
atgaggggta tctcgaagca cacgaaactt tttccttcct tcattcacgc acactactct     1260
ctaatgagca acggtatacg gccttccttc cagttacttg aatttgaaat aaaaaaaagt     1320
ttgctgtctt gctatcaagt ataaatagac ctgcaattat taatctttg tttcctcgtc     1380 attgttctcg ttccctttct tccttgtttc tttttctgca caatatttca agctatacca     1440
agcatacaat caactccaag ctggccgc                                        1468

<210> SEQ ID NO 34
<211> LENGTH: 4173
<212> TYPE: DNA
<213> ORGANISM: Artificial Sequence
<220> FEATURE:
<223> OTHER INFORMATION: Synthetic pUC57-ura3HA vector

<400> SEQUENCE: 34
gatgacggtg aaaacctctg acacatgcag ctcccggaga cggtcacagc ttgtctgtaa       60
gcggatgccg ggagcagaca gcccgtcag ggcgcgtcag cgggtgttgg cgggtgtcgg      120
ggctggctta actatgcggc atcagagcag attgtactga gagtgcacca tatgcggtgt      180
gaaataccgc acagatgcgt aaggagaaaa taccgcatca ggcgccattc gccattcagg      240
ctgcgcaact gttgggaagg gcgatcggtg cgggcctctt cgctattacg ccagctggcg      300
aaagggggat gtgctgcaag gcgattaagt tgggtaacgc cagggttttc ccagtcacga      360
cgttgtaaaa cgacggccag tgaattcgag ctcggtacct cgcgaatgca tctagatatc      420
ggatcccgac gagctgcacc gcggtggcgg ccgtatcttt acccatacg atgttcctga      480 ctatgcgggc tatccctatg acgtcccgga ctatgcagga tcctatccat atgacgttcc      540
agattacgct gctcagtgcg gccgcctgag agtgcaccat accacagctt tcaattcaa      600 ttcatcattt tttttttatt cttttttttg atttcggttt ctttgaaatt tttttgattc      660
ggtaatctcc gaacagaagg aagaacgaag gaaggagcac agacttagat tggtatatat      720
acgcatatgt agtgttgaag aaacatgaaa ttgcccagta ttcttaaccc aactgcacag      780
aacaaaaacc tgcaggaaac gaagataaat catgtcgaaa gctacatata aggaacgtgc      840
tgctactcat cctagtcctg ttgctgccaa gctatttaat atcatgcacg aaaagcaaac      900
aaacttgtgt gcttcattgg atgttcgtac caccaaggaa ttactggagt tagttgaagc      960
attaggtccc aaaatttgtt tactaaaaac acatgtggat atcttgactg attttttccat    1020 ggagggcaca gttaagccgc taaggcatt atccgccaag tacaatttttt tactcttcga     1080 agacagaaaa tttgctgaca ttggtaatac agtcaaattg cagtactctg cgggtgtata    1140
cagaatagca gaatgggcag acattacgaa tgcacggt gtggtgggcc caggtattgt      1200
tagcggtttg aagcaggcgg cagaagaagt aacaaaggaa cctagaggcc ttttgatgtt    1260
```

```
agcagaattg tcatgcaagg gctccctatc tactggagaa tatactaagg gtactgttga    1320
cattgcgaag agcgacaaag attttgttat cggctttatt gctcaaagag acatgggtgg    1380
aagagatgaa ggttacgatt ggttgattat gacacccggt gtgggtttag atgacaaggg    1440
agacgcattg ggtcaacagt atagaaccgt ggatgatgtg gtctctacag gatctgacat    1500
tattattgtt ggaagaggac tatttgcaaa gggaagggat gctaaggtag agggtgaacg    1560
ttacagaaaa gcaggctggg aagcatattt gagaagatgc ggccagcaaa actaaaaaac    1620
tgtattataa gtaaatgcat gtatactaaa ctcacaaatt agagcttcaa tttaattata    1680
tcagttatta ccctatgcgg tgtgaaatac cgcacagatg cgtaaggaga aaataccgca    1740
tcaggaaatt gtagcggccg cgaatttgag cttatctttt acccatacga tgttcctgac    1800
tatgcgggct atccctatga cgtcccggac tatgcaggat cctatccata tgacgttcca    1860
gattacgcta ctagcggggg gcccggtgac gggcccgtcg actgcagagg cctgcatgca    1920
agcttggcgt aatcatggtc atagctgttt cctgtgtgaa attgttatcc gctcacaatt    1980
ccacacaaca tacgagccgg aagcataaag tgtaaagcct ggggtgccta atgagtgagc    2040
taactcacat taattgcgtt gcgctcactg cccgctttcc agtcgggaaa cctgtcgtgc    2100
cagctgcatt aatgaatcgg ccaacgcgcg gggagaggcg gtttgcgtat gggcgctct    2160 tccgcttcct cgctcactga ctcgctgcgc tcggtcgttc ggctgcggcg agcggtatca    2220
gctcactcaa aggcggtaat acggttatcc acagaatcag gggataacgc aggaaagaac    2280
atgtgagcaa aaggccagca aaaggccagg aaccgtaaaa aggccgcgtt gctggcgttt    2340
ttccataggc tccgcccccc tgacgagcat cacaaaaatc gacgctcaag tcagaggtgg    2400
cgaaacccga caggactata aagataccag gcgtttcccc ctggaagctc cctcgtgcgc    2460
tctcctgttc cgaccctgcc gcttaccgga tacctgtccg cctttctccc ttcgggaagc    2520
gtggcgcttt ctcatagctc acgctgtagg tatctcagtt cggtgtaggt cgttcgctcc    2580
aagctgggct gtgtgcacga accccccgtt cagcccgacc gctgcgcctt atccggtaac    2640
tatcgtcttg agtccaaccc ggtaagacac gacttatcgc cactggcagc agccactggt    2700
aacaggatta gcagagcgag gtatgtaggc ggtgctacag agttcttgaa gtggtggcct    2760
aactacggct acactagaag aacagtattt ggtatctgcg ctctgctgaa gccagttacc    2820
ttcggaaaaa gagttggtag ctcttgatcc ggcaaacaaa ccaccgctgg tagcggtggt    2880
ttttttgttt gcaagcagca gattacgcgc agaaaaaaag gatctcaaga agatcctttg    2940
atcttttcta cggggtctga cgctcagtgg aacgaaaact cacgttaagg attttggtc    3000 atgagattat caaaaaggat cttcacctag atccttttaa attaaaaatg aagttttaaa    3060
tcaatctaaa gtatatatga gtaaacttgg tctgacagtt accaatgctt aatcagtgag    3120
gcacctatct cagcgatctg tctatttcgt tcatccatag ttgcctgact ccccgtcgtg    3180
tagataacta cgatacggga gggcttacca tctggcccca gtgctgcaat gataccgcga    3240
gacccacgct caccggctcc agatttatca gcaataaacc agccagccgg aagggccgag    3300
cgcagaagtg gtcctgcaac tttatccgcc tccatccagt ctattaattg ttgccgggaa    3360
gctagagtaa gtagttcgcc agttaatagt ttgcgcaacg ttgttgccat tgctacaggc    3420
atcgtggtgt cacgctcgtc gtttggtatg gcttcattca gctccggttc ccaacgatca    3480
aggcgagtta catgatcccc catgttgtgc aaaaaagcgg ttagctcctt cggtcctccg    3540
atcgttgtca gaagtaagtt ggccgcagtg ttatcactca tggttatggc agcactgcat    3600
aattctctta ctgtcatgcc atccgtaaga tgcttttctg tgactggtga gtactcaacc    3660
```

```
aagtcattct gagaatagtg tatgcggcga ccgagttgct cttgcccggc gtcaatacgg   3720
gataataccg cgccacatag cagaacttta aaagtgctca tcattggaaa acgttcttcg   3780
gggcgaaaac tctcaaggat cttaccgctg ttgagatcca gttcgatgta acccactcgt   3840
gcacccaact gatcttcagc atcttttact ttcaccagcg tttctgggtg agcaaaaaca   3900
ggaaggcaaa atgccgcaaa aaagggaata agggcgacac ggaaatgttg aatactcata   3960
ctcttccttt ttcaatatta ttgaagcatt tatcagggtt attgtctcat gagcggatac   4020
atatttgaat gtatttagaa aaataaacaa ataggggttc cgcgcacatt tccccgaaaa   4080
gtgccacctg acgtctaaga aaccattatt atcatgacat taacctataa aataggcgt   4140 atcacgaggc cctttcgtct cgcgcgtttc ggt                                4173
```

<210> SEQ ID NO 35
<211> LENGTH: 26
<212> TYPE: DNA
<213> ORGANISM: Artificial Sequence
<220> FEATURE:
<223> OTHER INFORMATION: Synthetic forward primer

<400> SEQUENCE: 35
gagctcaatt aaccctcact aaaggg                                        26

<210> SEQ ID NO 36
<211> LENGTH: 26
<212> TYPE: DNA
<213> ORGANISM: Artificial Sequence
<220> FEATURE:
<223> OTHER INFORMATION: Synthetic reverse primer

<400> SEQUENCE: 36
gagctccaaa ttaaagcctt cgagcg                                        26

<210> SEQ ID NO 37
<211> LENGTH: 60
<212> TYPE: DNA
<213> ORGANISM: Artificial Sequence
<220> FEATURE:
<223> OTHER INFORMATION: Synthetic forward primer

<400> SEQUENCE: 37
aagatctacg aagttgaagg tatgagatgg gctggtaacg ccagtcacga cgttgtaaaa   60

<210> SEQ ID NO 38
<211> LENGTH: 60
<212> TYPE: DNA
<213> ORGANISM: Artificial Sequence
<220> FEATURE:
<223> OTHER INFORMATION: Synthetic reverse primer

<400> SEQUENCE: 38
gcttccttaa cttctggctt ggacaaggta ccgacgtaaa aggtttcccg actggaaagc   60

<210> SEQ ID NO 39
<211> LENGTH: 70
<212> TYPE: DNA
<213> ORGANISM: Artificial Sequence
<220> FEATURE:
<223> OTHER INFORMATION: Synthetic forward primer

<400> SEQUENCE: 39
cgatgcgtat tttaagtggt tctctgaaca gcacaatgtc ctcgacacca ccagtcacga   60
cgttgtaaaa 70

<210> SEQ ID NO 40
<211> LENGTH: 72
<212> TYPE: DNA
<213> ORGANISM: Artificial Sequence
<220> FEATURE:
<223> OTHER INFORMATION: Synthetic reverse primer

<400> SEQUENCE: 40
ggatcacccc ccactcaagt cgttgcattg ctaacatgtg gcattctgcc caaggtttcc    60
cgactggaaa gc    72

<210> SEQ ID NO 41
<211> LENGTH: 70
<212> TYPE: DNA
<213> ORGANISM: Artificial Sequence
<220> FEATURE:
<223> OTHER INFORMATION: Synthetic forward primer

<400> SEQUENCE: 41
ccctatgtct ctggccgatc acgcgccatt gtccctcaga aacaaatcaa ccagtcacga    60
cgttgtaaaa    70

<210> SEQ ID NO 42
<211> LENGTH: 70
<212> TYPE: DNA
<213> ORGANISM: Artificial Sequence
<220> FEATURE:
<223> OTHER INFORMATION: Synthetic reverse primer

<400> SEQUENCE: 42
tagaagcaac tgtgccgaca gcctctgaat gagtggtgtt gtaaccaccc aggtttcccg    60
actggaaagc    70

<210> SEQ ID NO 43
<211> LENGTH: 22
<212> TYPE: DNA
<213> ORGANISM: Artificial Sequence
<220> FEATURE:
<223> OTHER INFORMATION: Synthetic forward primer

<400> SEQUENCE: 43
gctcttctct accctgtcat tc    22

<210> SEQ ID NO 44
<211> LENGTH: 22
<212> TYPE: DNA
<213> ORGANISM: Artificial Sequence
<220> FEATURE:
<223> OTHER INFORMATION: Synthetic reverse primer

<400> SEQUENCE: 44
tagtgtacag ggtgtcgtat ct    22

<210> SEQ ID NO 45
<211> LENGTH: 26
<212> TYPE: DNA
<213> ORGANISM: Artificial Sequence
<220> FEATURE:
<223> OTHER INFORMATION: Synthetic forward primer

<400> SEQUENCE: 45
ggagttgaag gcaaaattag aagtga    26

<210> SEQ ID NO 46
<211> LENGTH: 26
<212> TYPE: DNA
<213> ORGANISM: Artificial Sequence
<220> FEATURE:
<223> OTHER INFORMATION: Synthetic reverse primer

<400> SEQUENCE: 46
attccctttc ctgcacaaca cgagat                                          26

<210> SEQ ID NO 47
<211> LENGTH: 25
<212> TYPE: DNA
<213> ORGANISM: Artificial Sequence
<220> FEATURE:
<223> OTHER INFORMATION: Synthetic forward primer

<400> SEQUENCE: 47
tcaatgagac tgttgtcctc ctact                                           25

<210> SEQ ID NO 48
<211> LENGTH: 24
<212> TYPE: DNA
<213> ORGANISM: Artificial Sequence
<220> FEATURE:
<223> OTHER INFORMATION: Synthetic reverse primer

<400> SEQUENCE: 48
tacatccttg tcgagccttg ggca                                            24

<210> SEQ ID NO 49
<211> LENGTH: 3873
<212> TYPE: DNA
<213> ORGANISM: Artificial Sequence
<220> FEATURE:
<223> OTHER INFORMATION: Synthetic pUC19-HIS3 vector

<400> SEQUENCE: 49
agctcggtac ccggggatcc tctagagtcg acaattcccg ttttaagagc ttggtgagcg     60
ctaggagtca ctgccaggta tcgtttgaac acggcattag tcaggaagt cataacacag    120 tcctttcccg caattttctt tttctattac tcttggcctc ctctagtaca ctctatattt    180
ttttatgcct cggtaatgat tttcattttt tttttttcccc tagcggatga ctcttttttt    240
ttcttagcga ttggcattat cacataatga attatacatt atataaagta atgtgatttc    300
ttcgaagaat atactaaaaa atgagcaggc aagataaacg aaggcaaaga tgacagagca    360
gaaagcccta gtaaagcgta ttacaaatga aaccaagatt cagattgcga tctctttaaa    420
gggtggtccc ctagcgatag agcactcgat cttcccagaa aaagaggcag aagcagtagc    480
agaacaggcc acacaatcgc aagtgattaa cgtccacaca ggtatagggt tctggacca    540 tatgatacat gctctggcca agcattccgg ctggtcgcta atcgttgagt gcattggtga    600
cttacacata gacgaccatc acaccactga agactgcggg attgctctcg gtcaagcttt    660
taaagaggcc ctactggcgc gtggagtaaa aaggtttgga tcaggatttg cgcctttgga    720
tgaggcactt tccagagcgg tggtagatct ttcgaacagg ccgtacgcag ttgtcgaact    780
tggtttgcaa agggagaaag taggagatct ctcttgcgag atgatcccgc attttcttga    840
aagctttgca gaggctagca gaattaccct ccacgttgat tgtctgcgag caagaatga    900 tcatcaccgt agtgagagtg cgttcaaggc tcttgcggtt gccataagag aagccacctc    960

```
gcccaatggt accaacgatg ttccctccac caaaggtgtt cttatgtagt gacaccgatt    1020
atttaaagct gcagcatacg atatatatac atgtgtatat atgtatacct atgaatgtca    1080
gtaagtatgt atacgaacag tatgatactg aagatgacaa ggtaatgcat cattctatac    1140
gtgtcattct gaacgaggcg cgctttcctt ttttcttttt gctttttctt tttttttctc    1200
ttgaactcga cgggtcgacc tgcaggcatg caagcttggc gtaatcatgg tcatagctgt    1260
ttcctgtgtg aaattgttat ccgctcacaa ttccacacaa catacgagcc ggaagcataa    1320
agtgtaaagc ctggggtgcc taatgagtga gctaactcac attaattgcg ttgcgctcac    1380
tgcccgcttt ccagtcggga aacctgtcgt gccagctgca ttaatgaatc ggccaacgcg    1440
cggggagagg cggtttgcgt attgggcgct cttccgcttc ctcgctcact gactcgctgc    1500
gctcggtcgt tcggctgcgg cgagcggtat cagctcactc aaaggcggta atacggttat    1560
ccacagaatc aggggataac gcaggaaaga acatgtgagc aaaaggccag caaaaggcca    1620
ggaaccgtaa aaaggccgcg ttgctggcgt ttttccatag gctccgcccc cctgacgagc    1680
atcacaaaaa tcgacgctca agtcagaggt ggcgaaaccc gacaggacta taagataccc    1740
aggcgtttcc ccctggaagc tccctcgtgc gctctcctgt tccgaccctg ccgcttaccg    1800
gatacctgtc cgccттттctc ccttcgggaa gcgtggcgct ttctcatagc tcacgctgta    1860
ggtatctcag ttcggtgtag tcgttcgct ccaagctggg ctgtgtgcac gaaccccccg    1920

ttcagcccga ccgctgcgcc ttatccggta actatcgtct tgagtccaac ccggtaagac    1980
acgacttatc gccactggca gcagccactg gtaacaggat tagcagagcg aggtatgtag    2040
gcggtgctac agagttcttg aagtggtggc ctaactacgg ctacactaga agaacagtat    2100

ttggtatctg cgctctgctg aagccagtta ccttcggaaa agagttggt agctcttgat    2160 ccggcaaaca aaccaccgct ggtagcgtgt gttttttt gt ttgcaagcag cagattacgc    2220
gcagaaaaaa aggatctcaa gaagatcctt tgatctttt c tacggggtct gacgctcagt    2280
ggaacgaaaa ctcacgttaa gggattttgg tcatgagatt atcaaaaagg atcttcacct    2340 agatccttt aaattaaaaa tgaagttta aatcaatcta agtatatat gagtaaactt    2400 ggtctgacag ttaccaatgc ttaatcagtg aggcacctat ctcagcgatc tgtctatttc    2460
gttcatccat agttgcctga ctccccgtcg tgtagataac tacgatacgg gagggcttac    2520
catctggccc cagtgctgca atgatacccgc gagacccacg ctcaccggct ccagatttat    2580
cagcaataaa ccagccagcc ggaagggccg agcgcagaag tggtcctgca actttatccg    2640
cctccatcca gtctattaat tgttgccggg aagctagagt aagtagttcg ccagttaata    2700 gttgcgcaa cgttgttgcc attgctacag gcatcgtggt gtcacgctcg тcгттtggтa    2760 tggcttcatt cagctccggt tcccaacgat caaggcgagt tacatgatcc cccatgttgt    2820
gcaaaaaagc ggttagctcc ttcggtcctc cgatcgttgt cagaagtaag ttggccgcag    2880

тgттaтcactт caтggтттatg gcagcactgc ataattctct tactgtcatg ccatccgtaa    2940
gatgcttttc tgtgactggt gagtactcaa ccaagtcatt ctgagaatag tgtatgcggc    3000
gaccgagttg ctcttgcccg gcgtcaatac gggataatac cgcgccacat agcagaactt    3060
taaaagtgct catcattgga aaacgttctt cggggcgaaa actctcaagg atcttaccgc    3120
tgttgagatc cagttcgatg taacccactc gtgcacccaa ctgatcttca gcatcttta    3180 ctttcaccag cgtttctggg tgagcaaaaa caggaaggca aatgccgca aaaaagggaa    3240

taagggcgac acgaaatgt tgaatactca tactcttcct tttcaatat tattgaagca    3300

tttatcaggg ttattgtctc atgagcggat acatatttga atgtatttag aaaaataaac    3360
```

```
aaatagggt  tccgcgcaca  tttccccgaa  aagtgccacc  tgacgtctaa  gaaaccatta    3420
ttatcatgac  attaacctat  aaaaataggc  gtatcacgag  gcccttttcgt  ctcgcgcgtt    3480 tcggtgatga  cggtgaaaac  ctctgacaca  tgcagctccc  ggagacggtc  acagcttgtc    3540
tgtaagcgga  tgccgggagc  agacaagccc  gtcagggcgc  gtcagcgggt  gttggcgggt    3600 gtcgggctg   gcttaactat  gcggcatcag  agcagattgt  actgagagtg  caccatatgc    3660
ggtgtgaaat  accgcacaga  tgcgtaagga  gaaaataccg  catcaggcgc  cattcgccat    3720
tcaggctgcg  caactgttgg  gaagggcgat  cggtgcgggc  ctcttcgcta  ttacgccagc    3780
tggcgaaagg  gggatgtgct  gcaaggcgat  taagttgggt  aacgccaggg  ttttcccagt    3840
cacgacgttg  taaaacgacg  gccagtgaat  tcg                                    3873

<210> SEQ ID NO 50
<211> LENGTH: 31
<212> TYPE: DNA
<213> ORGANISM: Artificial Sequence
<220> FEATURE:
<223> OTHER INFORMATION: Synthetic primer

<400> SEQUENCE: 50
cctcctgagt cgacaattcc cgttttaaga g                                         31

<210> SEQ ID NO 51
<211> LENGTH: 30
<212> TYPE: DNA
<213> ORGANISM: Artificial Sequence
<220> FEATURE:
<223> OTHER INFORMATION: Synthetic primer

<400> SEQUENCE: 51
cgaccgtggt cgacccgtcg agttcaagag                                           30

<210> SEQ ID NO 52
<211> LENGTH: 69
<212> TYPE: DNA
<213> ORGANISM: Artificial Sequence
<220> FEATURE:
<223> OTHER INFORMATION: Synthetic forward primer

<400> SEQUENCE: 52
tgagcacgtg agtatacgtg attaagcaca caaaggcagc ttggagtatg gtgctgcaag         60
gcgattaag                                                                  69

<210> SEQ ID NO 53
<211> LENGTH: 67
<212> TYPE: DNA
<213> ORGANISM: Artificial Sequence
<220> FEATURE:
<223> OTHER INFORMATION: Synthetic reverse primer

<400> SEQUENCE: 53
aggcaagtgc acaaacaata cttaaataaa tactactcag taataacccg gctcgtatgt         60
tgtgtgg                                                                    67

<210> SEQ ID NO 54
<211> LENGTH: 21
<212> TYPE: DNA
<213> ORGANISM: Artificial Sequence
<220> FEATURE:
<223> OTHER INFORMATION: Synthetic forward primer
```

<400> SEQUENCE: 54
gccaaatgat ttagcattat c                                              21

<210> SEQ ID NO 55
<211> LENGTH: 21
<212> TYPE: DNA
<213> ORGANISM: Artificial Sequence
<220> FEATURE:
<223> OTHER INFORMATION: Synthetic reverse primer

<400> SEQUENCE: 55
aaaaggagag ggccaagagg g                                              21

<210> SEQ ID NO 56
<211> LENGTH: 60
<212> TYPE: DNA
<213> ORGANISM: Artificial Sequence
<220> FEATURE:
<223> OTHER INFORMATION: Synthetic forward primer

<400> SEQUENCE: 56
atgattagac aatcattaat gaaaacagtg tgggctaact ccagtcacga cgttgtaaaa    60

<210> SEQ ID NO 57
<211> LENGTH: 60
<212> TYPE: DNA
<213> ORGANISM: Artificial Sequence
<220> FEATURE:
<223> OTHER INFORMATION: Synthetic reverse primer

<400> SEQUENCE: 57
ctagatagat gaatctctac ccaagaaata aactttagcc aggtttcccg actggaaagc    60

<210> SEQ ID NO 58
<211> LENGTH: 22
<212> TYPE: DNA
<213> ORGANISM: Artificial Sequence
<220> FEATURE:
<223> OTHER INFORMATION: Synthetic forward primer

<400> SEQUENCE: 58
actgatcatc atttaaaaat gt                                             22

<210> SEQ ID NO 59
<211> LENGTH: 22
<212> TYPE: DNA
<213> ORGANISM: Artificial Sequence
<220> FEATURE:
<223> OTHER INFORMATION: Synthetic reverse primer

<400> SEQUENCE: 59
aaggaaaaaa attttcacac ta                                             22

<210> SEQ ID NO 60
<211> LENGTH: 70
<212> TYPE: DNA
<213> ORGANISM: Artificial Sequence
<220> FEATURE:
<223> OTHER INFORMATION: Synthetic forward primer

<400> SEQUENCE: 60
atgctgccca gacttggttt tgcgaggact gctaggtcca tacaccgttt ccagtcacga    60
cgttgtaaaa                                                           70

```
<210> SEQ ID NO 61
<211> LENGTH: 60
<212> TYPE: DNA
<213> ORGANISM: Artificial Sequence
<220> FEATURE:
<223> OTHER INFORMATION: Synthetic reverse primer

<400> SEQUENCE: 61
ctacacggag gaatcccttc caagaaagta aactttggtc aggtttcccg actggaaagc    60

<210> SEQ ID NO 62
<211> LENGTH: 62
<212> TYPE: DNA
<213> ORGANISM: Artificial Sequence
<220> FEATURE:
<223> OTHER INFORMATION: Synthetic primer

<400> SEQUENCE: 62
atgtcaggaa cattcaatga tataagaaga aggaagaagg aaccagtcac gacgttgtaa    60
aa                                                                  62

<210> SEQ ID NO 63
<211> LENGTH: 62
<212> TYPE: DNA
<213> ORGANISM: Artificial Sequence
<220> FEATURE:
<223> OTHER INFORMATION: Synthetic primer

<400> SEQUENCE: 63
ttacccaact atcttcaatt ctgcatccgg tacccatat ttaggtttcc cgactggaaa    60
gc                                                                  62

<210> SEQ ID NO 64
<211> LENGTH: 68
<212> TYPE: DNA
<213> ORGANISM: Artificial Sequence
<220> FEATURE:
<223> OTHER INFORMATION: Synthetic primer

<400> SEQUENCE: 64
atgggcacac tgtttcgaag aaatgtccag aaccaaaaga gtgattctcc agtcacgacg    60
ttgtaaaa                                                            68

<210> SEQ ID NO 65
<211> LENGTH: 68
<212> TYPE: DNA
<213> ORGANISM: Artificial Sequence
<220> FEATURE:
<223> OTHER INFORMATION: Synthetic primer

<400> SEQUENCE: 65
ttacattggg aagggcatct gagaaaccca ctggctcaaa ttagacaaag gtttcccgac    60
tggaaagc                                                            68

<210> SEQ ID NO 66
<211> LENGTH: 43
<212> TYPE: DNA
<213> ORGANISM: Artificial Sequence
<220> FEATURE:
<223> OTHER INFORMATION: Synthetic primer

<400> SEQUENCE: 66
tcatcaccac agccaggatc cgatggagta ccaaaatctc tta                     43
```

<210> SEQ ID NO 67
<211> LENGTH: 42
<212> TYPE: DNA
<213> ORGANISM: Artificial Sequence
<220> FEATURE:
<223> OTHER INFORMATION: Synthetic primer

<400> SEQUENCE: 67
gcattatgcg ccgcaagct tttatagtcc tttaaaaata gg         42

<210> SEQ ID NO 68
<211> LENGTH: 43
<212> TYPE: DNA
<213> ORGANISM: Artificial Sequence
<220> FEATURE:
<223> OTHER INFORMATION: Synthetic primer

<400> SEQUENCE: 68
tcatcaccac agccaggatc cgatgaagta taaaaattta att        43

<210> SEQ ID NO 69
<211> LENGTH: 42
<212> TYPE: DNA
<213> ORGANISM: Artificial Sequence
<220> FEATURE:
<223> OTHER INFORMATION: Synthetic primer

<400> SEQUENCE: 69
gcattatgcg ccgcaagct tttacttatc tttaaagact gc         42

<210> SEQ ID NO 70
<211> LENGTH: 43
<212> TYPE: DNA
<213> ORGANISM: Artificial Sequence
<220> FEATURE:
<223> OTHER INFORMATION: Synthetic primer

<400> SEQUENCE: 70
tcatcaccac agccaggatc cgatggagta cagtaatctc ttg        43

<210> SEQ ID NO 71
<211> LENGTH: 42
<212> TYPE: DNA
<213> ORGANISM: Artificial Sequence
<220> FEATURE:
<223> OTHER INFORMATION: Synthetic primer

<400> SEQUENCE: 71
gcattatgcg ccgcaagct tttacttgcc ggtaaatttg gc         42

<210> SEQ ID NO 72
<211> LENGTH: 36
<212> TYPE: DNA
<213> ORGANISM: Artificial Sequence
<220> FEATURE:
<223> OTHER INFORMATION: Synthetic primer

<400> SEQUENCE: 72
tagaactagt ggatcatggc aaaccctttt tcgaga              36

<210> SEQ ID NO 73
<211> LENGTH: 36
<212> TYPE: DNA
<213> ORGANISM: Artificial Sequence
<220> FEATURE:
<223> OTHER INFORMATION: Synthetic primer

```
<400> SEQUENCE: 73
aattacatga ctcgattaag ccctctttac acctag                                    36

<210> SEQ ID NO 74
<211> LENGTH: 43
<212> TYPE: DNA
<213> ORGANISM: Artificial Sequence
<220> FEATURE:
<223> OTHER INFORMATION: Synthetic primer

<400> SEQUENCE: 74
tcatcaccac agccaggatc cgatggcttt tgaaaatatt ttg                            43

<210> SEQ ID NO 75
<211> LENGTH: 42
<212> TYPE: DNA
<213> ORGANISM: Artificial Sequence
<220> FEATURE:
<223> OTHER INFORMATION: Synthetic primer

<400> SEQUENCE: 75
gcattatgcg gccgcaagct tttactttcc cttaaattct gc                             42

<210> SEQ ID NO 76
<211> LENGTH: 28
<212> TYPE: DNA
<213> ORGANISM: Artificial Sequence
<220> FEATURE:
<223> OTHER INFORMATION: Synthetic primer

<400> SEQUENCE: 76
gatatggtat gataaatttg gcggctgg                                             28

<210> SEQ ID NO 77
<211> LENGTH: 28
<212> TYPE: DNA
<213> ORGANISM: Artificial Sequence
<220> FEATURE:
<223> OTHER INFORMATION: Synthetic primer

<400> SEQUENCE: 77 caccettgga gtcagcatcg tcaacgta                                             28

<210> SEQ ID NO 78
<211> LENGTH: 43
<212> TYPE: DNA
<213> ORGANISM: Artificial Sequence
<220> FEATURE:
<223> OTHER INFORMATION: Synthetic primer

<400> SEQUENCE: 78
tcatcaccac agccaggatc cgatggaata taaaaacata gaa                            43

<210> SEQ ID NO 79
<211> LENGTH: 42
<212> TYPE: DNA
<213> ORGANISM: Artificial Sequence
<220> FEATURE:
<223> OTHER INFORMATION: Synthetic primer

<400> SEQUENCE: 79
gcattatgcg gccgcaagct tttatcttcc ttcaaattta gg                             42
```